United States Patent
Lang et al.

(10) Patent No.: US 8,337,507 B2
(45) Date of Patent: *Dec. 25, 2012

(54) METHODS AND COMPOSITIONS FOR ARTICULAR REPAIR

(75) Inventors: Philipp Lang, Lexington, MA (US); Daniel Steines, Lexington, MA (US); Konstantinos Tsourgarakis, Sunnyvale, CA (US)

(73) Assignee: ConforMIS, Inc., Burlington, MA (US)

( * ) Notice: Subject to any disclaimer, the term of this patent is extended or adjusted under 35 U.S.C. 154(b) by 128 days.

This patent is subject to a terminal disclaimer.

(21) Appl. No.: 12/317,472

(22) Filed: Dec. 22, 2008

(65) Prior Publication Data
US 2009/0306676 A1 Dec. 10, 2009

Related U.S. Application Data

(63) Continuation of application No. 10/305,652, filed on Nov. 27, 2002, now Pat. No. 7,468,075, which is a continuation-in-part of application No. 10/160,667, filed on May 28, 2002.

(60) Provisional application No. 60/293,488, filed on May 25, 2001, provisional application No. 60/363,527, filed on Mar. 12, 2002, provisional application No. 60/380,695, filed on May 14, 2002, provisional application No. 60/380,692, filed on May 14, 2002.

(51) Int. Cl.
*A61B 17/58* (2006.01)
*A61B 17/56* (2006.01)

(52) U.S. Cl. ...................... 606/102; 606/86 R

(58) Field of Classification Search ............... 623/23.61, 623/16.11, 20.14, 20.35, 914, 18.11; 600/410, 600/587, 427; 606/96, 80, 88, 86 R, 102; 128/898; 328/128
See application file for complete search history.

(56) References Cited

U.S. PATENT DOCUMENTS

| | | | |
|---|---|---|---|
| 3,314,420 A | 4/1967 | Smith et al. | 128/92 |
| 3,605,123 A | 9/1971 | Hahn | 3/1 |
| 3,694,820 A | 10/1972 | Scales et al. | 3/1 |
| 3,798,679 A | 3/1974 | Ewald | 3/1 |
| 3,808,606 A | 5/1974 | Tronzo | 3/1 |
| 3,816,855 A | 6/1974 | Saleh | 3/1 |
| 3,843,975 A | 10/1974 | Tronzo | 3/1 |
| 3,852,830 A | 12/1974 | Marmor | 3/1 |

(Continued)

FOREIGN PATENT DOCUMENTS
CN 86209787 11/1987
(Continued)

OTHER PUBLICATIONS

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989).

(Continued)

*Primary Examiner* — Pedro Philogene
(74) *Attorney, Agent, or Firm* — Sunstein Kann Murphy & Timbers LLP

(57) ABSTRACT

Disclosed herein are methods and compositions for producing articular repair materials and for repairing an articular surface. In particular, methods for providing articular repair systems. Also provided are articular surface repair systems designed to replace a selected area cartilage, for example, and surgical tools for repairing articular surfaces.

34 Claims, 18 Drawing Sheets
(3 of 18 Drawing Sheet(s) Filed in Color)

U.S. PATENT DOCUMENTS

| | | | |
|---|---|---|---|
| 3,855,638 A | 12/1974 | Pilliar | 3/1 |
| 3,938,198 A | 2/1976 | Kahn et al. | 3/1.912 |
| 3,987,499 A | 10/1976 | Scharbach et al. | 3/1.91 |
| 3,991,425 A | 11/1976 | Martin et al. | 3/1.91 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,098,626 A | 7/1978 | Graham et al. | 149/19.4 |
| 4,164,793 A | 8/1979 | Swanson | 3/1.91 |
| 4,178,641 A | 12/1979 | Grundei et al. | 3/1.911 |
| 4,203,444 A | 5/1980 | Bonnell | 128/276 |
| 4,207,627 A | 6/1980 | Cloutier | 3/1.91 |
| 4,213,816 A | 7/1980 | Morris | 156/245 |
| 4,219,893 A | 9/1980 | Noiles | 3/1.911 |
| 4,280,231 A | 7/1981 | Swanson | 3/1.91 |
| 4,309,778 A | 1/1982 | Buechel et al. | 3/1.911 |
| 4,340,978 A | 7/1982 | Buechel et al. | 3/1.911 |
| 4,344,193 A | 8/1982 | Kenny | 3/1.911 |
| 4,368,040 A | 1/1983 | Weissman | 433/36 |
| 4,436,684 A | 3/1984 | White | 264/138 |
| 4,459,985 A | 7/1984 | McKay et al. | 128/303 R |
| 4,502,161 A | 3/1985 | Wall | 3/1.91 |
| 4,575,805 A | 3/1986 | Moermann et al. | 364/474 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,655,227 A | 4/1987 | Gracovetsky | 128/781 |
| 4,699,156 A | 10/1987 | Gracovetsky | 128/781 |
| 4,714,472 A | 12/1987 | Averill et al. | 623/20 |
| 4,714,474 A | 12/1987 | Brooks, Jr. et al. | 623/20 |
| 4,769,040 A | 9/1988 | Wevers | 623/20 |
| 4,813,436 A | 3/1989 | Au | 128/779 |
| 4,822,365 A | 4/1989 | Walker et al. | 128/898 |
| 4,823,807 A | 4/1989 | Russell et al. | 128/773 |
| 4,846,835 A | 7/1989 | Grande | 623/11 |
| 4,865,607 A | 9/1989 | Witzel et al. | 623/20 |
| 4,872,452 A | 10/1989 | Alexson | 128/92 |
| 4,880,429 A | 11/1989 | Stone | 623/18 |
| 4,888,021 A | 12/1989 | Forte et al. | 623/20 |
| 4,936,862 A | 6/1990 | Walker et al. | 623/23 |
| 4,944,757 A | 7/1990 | Martinez et al. | 623/20 |
| 5,021,061 A | 6/1991 | Wevers et al. | 623/20 |
| 5,041,138 A | 8/1991 | Vacanti et al. | 623/16 |
| 5,059,216 A | 10/1991 | Winters | 623/20 |
| 5,067,964 A | 11/1991 | Richmond et al. | 623/18 |
| 5,099,859 A | 3/1992 | Bell | 128/781 |
| 5,108,452 A | 4/1992 | DeMane et al. | 623/23 |
| 5,123,927 A | 6/1992 | Duncan et al. | 623/20 |
| 5,129,908 A | 7/1992 | Petersen | 606/88 |
| 5,133,759 A | 7/1992 | Turner | 623/20 |
| 5,150,304 A | 9/1992 | Berchem et al. | 364/474.24 |
| 5,154,178 A | 10/1992 | Shah | 128/653.2 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,245,282 A | 9/1993 | Mugler, III et al. | 324/309 |
| 5,246,013 A | 9/1993 | Frank et al. | 128/774 |
| 5,246,530 A | 9/1993 | Bugle et al. | 156/643 |
| 5,270,300 A | 12/1993 | Hunziker | 514/12 |
| 5,274,565 A | 12/1993 | Reuben | 364/474.24 |
| 5,282,868 A | 2/1994 | Bahler | 623/20 |
| 5,288,797 A | 2/1994 | Khalil et al. | 524/872 |
| 5,303,148 A | 4/1994 | Mattson et al. | 364/413.01 |
| 5,306,307 A | 4/1994 | Senter et al. | 623/17 |
| 5,306,311 A | 4/1994 | Stone et al. | 623/18 |
| 5,314,478 A | 5/1994 | Oka et al. | 623/18 |
| 5,314,482 A | 5/1994 | Goodfellow et al. | 623/20 |
| 5,320,102 A | 6/1994 | Paul et al. | 128/653.2 |
| 5,326,365 A | 7/1994 | Alvine | 623/21 |
| 5,344,459 A | 9/1994 | Swartz | 623/18 |
| 5,360,446 A | 11/1994 | Kennedy | 623/16 |
| 5,365,996 A | 11/1994 | Crook | 164/45 |
| 5,368,858 A | 11/1994 | Hunziker | 424/423 |
| 5,413,116 A | 5/1995 | Radke et al. | 128/777 |
| 5,423,828 A | 6/1995 | Benson | 606/102 |
| 5,433,215 A | 7/1995 | Athanasiou et al. | 128/774 |
| 5,445,152 A | 8/1995 | Bell et al. | 128/653.5 |
| 5,448,489 A | 9/1995 | Reuben | 364/474.05 |
| 5,468,787 A | 11/1995 | Braden et al. | 523/113 |
| 5,478,739 A | 12/1995 | Slivka et al. | 435/240.23 |
| 5,489,309 A | 2/1996 | Lackey et al. | 623/19 |
| 5,501,687 A | 3/1996 | Willert et al. | 606/94 |
| 5,503,162 A | 4/1996 | Athanasiou et al. | 128/774 |
| 5,507,820 A | 4/1996 | Pappas | 623/20 |
| 5,510,121 A | 4/1996 | Rhee et al. | 424/520 |
| 5,522,900 A | 6/1996 | Hollister | 623/18 |
| 5,523,843 A | 6/1996 | Yamane et al. | 356/363 |
| 5,533,519 A | 7/1996 | Radke et al. | 128/777 |
| 5,541,515 A | 7/1996 | Tsujita | 324/318 |
| 5,549,690 A | 8/1996 | Hollister et al. | 623/21 |
| 5,554,190 A | 9/1996 | Draenert | 623/16 |
| 5,556,432 A | 9/1996 | Kubein-Meesenburg et al. | 623/20 |
| 5,560,096 A | 10/1996 | Stephens | 29/558 |
| 5,564,437 A | 10/1996 | Bainville et al. | 128/774 |
| 5,571,191 A | 11/1996 | Fitz | 623/17 |
| 5,571,205 A | 11/1996 | James | 623/24 |
| 5,609,640 A | 3/1997 | Johnson | 623/20.2 |
| 5,616,146 A | 4/1997 | Murray | 606/80 |
| 5,632,745 A | 5/1997 | Schwartz | 606/75 |
| 5,671,741 A | 9/1997 | Lang et al. | 128/653.2 |
| 5,681,354 A | 10/1997 | Eckhoff | 623/20 |
| 5,682,886 A * | 11/1997 | Delp et al. | 600/407 |
| 5,683,466 A | 11/1997 | Vitale | 623/20 |
| 5,683,468 A | 11/1997 | Pappas | 623/20 |
| 5,684,562 A | 11/1997 | Fujieda | 351/212 |
| 5,687,210 A | 11/1997 | Maitrejean et al. | 378/57 |
| 5,690,635 A | 11/1997 | Matsen, III et al. | 606/88 |
| 5,702,463 A | 12/1997 | Pothier et al. | 623/20 |
| 5,723,331 A | 3/1998 | Tubo et al. | 435/366 |
| 5,728,162 A | 3/1998 | Eckhoff | 623/20 |
| 5,735,277 A | 4/1998 | Schuster | 128/653.1 |
| 5,749,362 A | 5/1998 | Funda et al. | 128/653.1 |
| 5,749,874 A | 5/1998 | Schwartz | 606/75 |
| 5,749,876 A | 5/1998 | Duvillier et al. | 606/88 |
| 5,759,205 A | 6/1998 | Valentini | 623/16 |
| 5,768,134 A | 6/1998 | Swaelens et al. | 364/468.28 |
| 5,769,899 A | 6/1998 | Schwartz et al. | 623/18 |
| 5,772,595 A | 6/1998 | Votruba et al. | 600/415 |
| 5,779,651 A | 7/1998 | Buschmann et al. | 600/587 |
| 5,786,217 A | 7/1998 | Tubo et al. | 435/402 |
| 5,810,006 A | 9/1998 | Votruba et al. | 128/653.2 |
| 5,824,085 A * | 10/1998 | Sahay et al. | 128/898 |
| 5,824,102 A | 10/1998 | Buscayret | 623/20 |
| 5,827,289 A | 10/1998 | Reiley et al. | 606/86 |
| 5,832,422 A | 11/1998 | Wiedenhoefer | 702/154 |
| 5,835,619 A | 11/1998 | Morimoto et al. | 382/132 |
| 5,840,443 A | 11/1998 | Gregg et al. | 428/689 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,871,018 A * | 2/1999 | Delp et al. | 128/898 |
| 5,871,540 A | 2/1999 | Weissman et al. | 623/20 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia III et al. | 364/578 |
| 5,885,296 A | 3/1999 | Masini | 606/86 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,913,821 A | 6/1999 | Farese et al. | 600/425 |
| 5,916,220 A | 6/1999 | Masini | 606/88 |
| 5,928,945 A | 7/1999 | Seliktar et al. | 435/395 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |

| Patent No. | Kind | Date | Inventors | Class |
|---|---|---|---|---|
| 6,002,859 | A | 12/1999 | DiGioia, III et al. | 395/500.32 |
| 6,013,103 | A | 1/2000 | Kaufman et al. | 623/20 |
| 6,046,379 | A | 4/2000 | Stone et al. | 623/11 |
| 6,057,927 | A | 5/2000 | Lévesque et al. | 356/432 T |
| 6,078,680 | A | 6/2000 | Yoshida et al. | 382/128 |
| 6,081,577 | A | 6/2000 | Webber | 378/23 |
| 6,082,364 | A | 7/2000 | Balian et al. | 128/898 |
| 6,090,144 | A | 7/2000 | Letot et al. | 623/20 |
| 6,093,204 | A | 7/2000 | Stone | 623/14.12 |
| 6,102,916 | A | 8/2000 | Masini | 606/88 |
| 6,102,955 | A | 8/2000 | Mendes et al. | 623/20.32 |
| 6,110,209 | A | 8/2000 | Stone | 623/16.11 |
| 6,112,109 | A | 8/2000 | D'Urso | 600/407 |
| 6,120,541 | A | 9/2000 | Johnson | 623/14.11 |
| 6,126,690 | A | 10/2000 | Ateshian et al. | 623/18 |
| 6,139,578 | A | 10/2000 | Lee et al. | 623/16.11 |
| 6,146,422 | A | 11/2000 | Lawson | 623/17.16 |
| 6,151,521 | A | 11/2000 | Guo et al. | 600/407 |
| 6,156,069 | A | 12/2000 | Amstutz | 623/22.11 |
| 6,161,080 | A | 12/2000 | Aouni-Ateshian et al. | 703/11 |
| 6,162,208 | A | 12/2000 | Hipps | 606/1 |
| 6,165,221 | A | 12/2000 | Schmotzer | 623/20.11 |
| 6,171,340 | B1 | 1/2001 | McDowell | 623/18.11 |
| 6,175,655 | B1 | 1/2001 | George, III et al. | 382/257 |
| 6,178,225 | B1 | 1/2001 | Zur et al. | 378/98.2 |
| 6,187,010 | B1 | 2/2001 | Masini | 606/86 |
| 6,197,064 | B1 | 3/2001 | Haines et al. | 623/20.31 |
| 6,197,325 | B1 | 3/2001 | MacPhee et al. | 424/426 |
| 6,200,606 | B1 | 3/2001 | Peterson et al. | 424/574 |
| 6,203,576 | B1 | 3/2001 | Afriat et al. | 623/20.27 |
| 6,205,411 | B1 | 3/2001 | DiGioia, III et al. | 703/11 |
| 6,206,927 | B1 | 3/2001 | Fell et al. | 623/20.29 |
| 6,214,369 | B1 | 4/2001 | Grande et al. | 424/423 |
| 6,217,894 | B1 | 4/2001 | Sawhney et al. | 424/426 |
| 6,219,571 | B1 | 4/2001 | Hargreaves et al. | 600/410 |
| 6,224,632 | B1 | 5/2001 | Pappas et al. | 623/20.34 |
| 6,235,060 | B1 | 5/2001 | Kubein-Meesenburg et al. | 623/20.31 |
| 6,249,692 | B1 | 6/2001 | Cowin | 600/407 |
| 6,251,143 | B1 | 6/2001 | Schwartz et al. | 623/23.72 |
| 6,254,639 | B1 | 7/2001 | Peckitt | 623/11.11 |
| 6,261,296 | B1 | 7/2001 | Aebi et al. | 606/90 |
| 6,277,151 | B1 | 8/2001 | Lee et al. | 623/23.61 |
| 6,281,195 | B1 | 8/2001 | Rueger et al. | 514/21 |
| 6,283,980 | B1 | 9/2001 | Vibe-Hansen et al. | 606/151 |
| 6,289,115 | B1 | 9/2001 | Takeo | 382/130 |
| 6,289,753 | B1 | 9/2001 | Basser et al. | 73/866 |
| 6,299,905 | B1 | 10/2001 | Peterson et al. | 424/486 |
| 6,302,582 | B1 | 10/2001 | Nord et al. | 378/207 |
| 6,310,477 | B1 | 10/2001 | Schneider | 324/307 |
| 6,310,619 | B1 | 10/2001 | Rice | 345/420 |
| 6,316,153 | B1 | 11/2001 | Goodman et al. | 430/8 |
| 6,319,712 | B1 | 11/2001 | Meenen et al. | 435/395 |
| 6,322,588 | B1 | 11/2001 | Ogle et al. | 623/1.46 |
| 6,328,765 | B1 | 12/2001 | Hardwick et al. | 623/23.72 |
| 6,334,006 | B1 | 12/2001 | Tanabe | 385/12 |
| 6,334,066 | B1 | 12/2001 | Rupprecht et al. | 600/411 |
| 6,342,075 | B1 | 1/2002 | MacArthur | 623/20.14 |
| 6,344,059 | B1 | 2/2002 | Krakovits et al. | 623/20.31 |
| 6,352,558 | B1 | 3/2002 | Spector | 623/18.11 |
| 6,358,253 | B1 | 3/2002 | Torrie et al. | 606/96 |
| 6,365,405 | B1 | 4/2002 | Salzmann et al. | 435/366 |
| 6,371,958 | B1 | 4/2002 | Overaker | 606/72 |
| 6,373,250 | B1 | 4/2002 | Tsoref et al. | 324/309 |
| 6,375,658 | B1 | 4/2002 | Hangody et al. | 606/80 |
| 6,379,367 | B1 | 4/2002 | Vibe-Hansen et al. | 606/151 |
| 6,379,388 | B1 | 4/2002 | Ensign et al. | 623/20.34 |
| 6,382,028 | B1 | 5/2002 | Wooh et al. | 73/602 |
| 6,383,228 | B1 | 5/2002 | Schmotzer | 623/23.35 |
| 6,387,131 | B1 | 5/2002 | Miehlke et al. | 623/20.15 |
| 6,429,013 | B1 | 8/2002 | Halvorsen et al. | 435/377 |
| 6,443,988 | B2 | 9/2002 | Felt et al. | 623/17.12 |
| 6,443,991 | B1 | 9/2002 | Running | 623/20.27 |
| 6,444,222 | B1 | 9/2002 | Asculai et al. | 424/484 |
| 6,450,978 | B1 | 9/2002 | Brosseau et al. | 600/595 |
| 6,459,948 | B1 | 10/2002 | Ateshian et al. | 700/117 |
| 6,468,314 | B2 | 10/2002 | Schwartz et al. | 623/23.72 |
| 6,479,996 | B1 | 11/2002 | Hoogeveen et al. | 324/309 |
| 6,482,209 | B1 | 11/2002 | Engh et al. | 606/79 |
| 6,510,334 | B1 | 1/2003 | Schuster et al. | 600/407 |
| 6,514,514 | B1 | 2/2003 | Atkinson et al. | 424/423 |
| 6,520,964 | B2 | 2/2003 | Tallarida et al. | 396/567 |
| 6,533,737 | B1 | 3/2003 | Brosseau et al. | 600/595 |
| 6,556,855 | B2 | 4/2003 | Thesen | 600/419 |
| 6,558,421 | B1 | 5/2003 | Fell et al. | 623/14.12 |
| 6,560,476 | B1 * | 5/2003 | Pelletier et al. | 600/410 |
| 6,575,980 | B1 | 6/2003 | Robie et al. | 606/88 |
| 6,591,581 | B2 | 7/2003 | Schmieding | 53/396 |
| 6,592,624 | B1 | 7/2003 | Fraser et al. | 623/17.16 |
| 6,623,526 | B1 | 9/2003 | Lloyd | 623/20.28 |
| 6,626,945 | B2 | 9/2003 | Simon et al. | 623/17.19 |
| 6,632,235 | B2 | 10/2003 | Weikel et al. | 606/192 |
| 6,652,587 | B2 | 11/2003 | Felt et al. | 623/20.16 |
| 6,679,917 | B2 | 1/2004 | Ek | 623/20.14 |
| 6,690,816 | B2 | 2/2004 | Aylward et al. | 382/128 |
| 6,692,448 | B2 | 2/2004 | Tanaka et al. | 600/587 |
| 6,702,821 | B2 | 3/2004 | Bonutti | 606/88 |
| 6,712,856 | B1 * | 3/2004 | Carignan et al. | 623/20.35 |
| 6,719,794 | B2 | 4/2004 | Gerber et al. | 623/17.11 |
| 6,770,078 | B2 | 8/2004 | Bonutti | 606/88 |
| 6,772,026 | B2 | 8/2004 | Bradbury et al. | 700/98 |
| 6,799,066 | B2 | 9/2004 | Steines et al. | 600/407 |
| 6,816,607 | B2 | 11/2004 | O'Donnell et al. | 382/131 |
| 6,835,377 | B2 | 12/2004 | Goldberg et al. | 424/93.7 |
| 6,855,165 | B2 | 2/2005 | Fell et al. | 623/14.12 |
| 6,873,741 | B2 | 3/2005 | Li | 382/266 |
| 6,893,463 | B2 | 5/2005 | Fell et al. | 623/14.12 |
| 6,893,467 | B1 | 5/2005 | Bercovy | 623/20.14 |
| 6,905,514 | B2 | 6/2005 | Carignan et al. | 623/20.35 |
| 6,911,044 | B2 | 6/2005 | Fell et al. | 623/14.12 |
| 6,916,341 | B2 | 7/2005 | Rolston | 623/20.3 |
| 6,923,831 | B2 | 8/2005 | Fell et al. | 623/14.12 |
| 6,932,842 | B1 | 8/2005 | Litschko et al. | 623/16.11 |
| 6,964,687 | B1 | 11/2005 | Bernard et al. | 623/17.16 |
| 6,966,928 | B2 | 11/2005 | Fell et al. | 623/14.12 |
| 6,984,981 | B2 | 1/2006 | Tamez-Peña et al. | 324/309 |
| 6,998,841 | B1 | 2/2006 | Tamez-Peña et al. | 324/302 |
| 7,020,314 | B1 | 3/2006 | Suri et al. | 382/130 |
| 7,050,534 | B2 | 5/2006 | Lang | 378/54 |
| 7,058,159 | B2 | 6/2006 | Lang et al. | 378/54 |
| 7,058,209 | B2 | 6/2006 | Chen et al. | 382/117 |
| 7,105,026 | B2 | 9/2006 | Johnson et al. | 623/20.14 |
| 7,115,131 | B2 | 10/2006 | Engh et al. | 606/79 |
| 7,174,282 | B2 | 2/2007 | Hollister et al. | 703/2 |
| 7,184,814 | B2 | 2/2007 | Lang et al. | 600/416 |
| 7,204,807 | B2 | 4/2007 | Tsoref | 600/438 |
| 7,238,203 | B2 | 7/2007 | Bagga et al. | 623/17.11 |
| 7,239,908 | B1 | 7/2007 | Alexander et al. | 600/427 |
| 7,244,273 | B2 | 7/2007 | Pedersen et al. | 623/14.12 |
| 7,245,697 | B2 | 7/2007 | Lang | 378/54 |
| 7,292,674 | B2 | 11/2007 | Lang | 378/54 |
| 7,379,529 | B2 | 5/2008 | Lang | 378/54 |
| 7,438,685 | B2 | 10/2008 | Burdette et al. | 600/439 |
| 7,467,892 | B2 | 12/2008 | Lang et al. | 378/207 |
| 7,468,075 | B2 * | 12/2008 | Lang et al. | 623/16.11 |
| 7,520,901 | B2 | 4/2009 | Engh et al. | 623/20.21 |
| 7,534,263 | B2 | 5/2009 | Burdulis, Jr. et al. | 623/14.12 |
| 7,611,519 | B2 | 11/2009 | Lefevre et al. | 606/102 |
| 7,615,054 | B1 | 11/2009 | Bonutti | 606/88 |
| 7,634,119 | B2 | 12/2009 | Tsougarakis et al. | 382/128 |
| 7,636,459 | B2 * | 12/2009 | Dore et al. | 382/128 |
| 7,796,791 | B2 | 9/2010 | Tsougarakis et al. | 382/128 |
| 7,799,077 | B2 | 9/2010 | Lang et al. | 623/14.12 |
| 7,842,092 | B2 | 11/2010 | Otto et al. | 623/18.11 |
| 7,881,768 | B2 * | 2/2011 | Lang et al. | 600/407 |
| 7,914,582 | B2 | 3/2011 | Felt et al. | 623/20.16 |
| 7,983,777 | B2 | 7/2011 | Melton et al. | 700/98 |
| 8,036,729 | B2 | 10/2011 | Lang et al. | 600/407 |
| 8,077,950 | B2 | 12/2011 | Tsougarakis et al. | 382/128 |
| 8,094,900 | B2 | 1/2012 | Steines et al. | 382/128 |
| 8,112,142 | B2 | 2/2012 | Alexander et al. | 600/407 |
| RE43,282 | E | 3/2012 | Alexander et al. | 600/427 |
| 2001/0001120 | A1 | 5/2001 | Masini | 606/86 |
| 2001/0010023 | A1 | 7/2001 | Schwartz et al. | 623/23.72 |
| 2001/0039455 | A1 | 11/2001 | Simon et al. | 623/23.51 |
| 2002/0013626 | A1 | 1/2002 | Geistlich et al. | 623/23.57 |
| 2002/0016543 | A1 | 2/2002 | Tyler | 600/410 |
| 2002/0022884 | A1 | 2/2002 | Mansmann | 623/14.12 |

| | | | | | | |
|---|---|---|---|---|---|---|
| 2002/0045940 A1 | 4/2002 | Giannetti et al. | 623/11.11 | 2006/0210017 A1 | 9/2006 | Lang ... 378/54 |
| 2002/0059049 A1 | 5/2002 | Bradbury et al. | 703/11 | 2006/0210018 A1 | 9/2006 | Lang ... 378/54 |
| 2002/0067798 A1 | 6/2002 | Lang | 378/54 | 2007/0015995 A1 | 1/2007 | Lang et al. ... 600/407 |
| 2002/0068979 A1 | 6/2002 | Brown et al. | 623/20.3 | 2007/0047794 A1 | 3/2007 | Lang et al. ... 378/132 |
| 2002/0072821 A1 | 6/2002 | Baker | 700/98 | 2007/0067032 A1 | 3/2007 | Felt et al. ... 623/14.12 |
| 2002/0082703 A1 | 6/2002 | Repicci | 623/20.29 | 2007/0083266 A1 | 4/2007 | Lang ... 623/17.11 |
| 2002/0087274 A1 | 7/2002 | Alexander et al. | 702/19 | 2007/0100462 A1 | 5/2007 | Lang et al. ... 623/20.29 |
| 2002/0106625 A1 | 8/2002 | Hung et al. | 435/1.1 | 2007/0118055 A1 | 5/2007 | McCombs ... 600/587 |
| 2002/0111694 A1 | 8/2002 | Ellingsen et al. | 623/23.57 | 2007/0118222 A1 | 5/2007 | Lang ... 623/17.12 |
| 2002/0115647 A1 | 8/2002 | Halvorsen et al. | 514/171 | 2007/0118243 A1 | 5/2007 | Schroeder et al. ... 700/118 |
| 2002/0120274 A1 | 8/2002 | Overaker et al. | 606/72 | 2007/0156171 A1 | 7/2007 | Lang et al. ... 606/205 |
| 2002/0120281 A1 | 8/2002 | Overaker | 606/151 | 2007/0198022 A1 | 8/2007 | Lang et al. ... 606/88 |
| 2002/0127264 A1 | 9/2002 | Felt et al. | 424/423 | 2007/0203430 A1 | 8/2007 | Lang et al. ... 600/587 |
| 2002/0133230 A1 | 9/2002 | Repicci | 623/14.12 | 2007/0233269 A1 | 10/2007 | Steines et al. ... 623/20.21 |
| 2002/0147392 A1 | 10/2002 | Steines et al. | 600/407 | 2007/0250169 A1 | 10/2007 | Lang ... 623/17.12 |
| 2002/0151986 A1 | 10/2002 | Asculai et al. | 424/484 | 2007/0274444 A1 | 11/2007 | Lang ... 378/54 |
| 2002/0156150 A1 | 10/2002 | Williams et al. | 623/23.75 | 2007/0276224 A1 | 11/2007 | Lang et al. ... 600/410 |
| 2002/0173852 A1 | 11/2002 | Felt et al. | 623/20.32 | 2007/0276501 A1 | 11/2007 | Betz et al. ... 623/17.16 |
| 2002/0177770 A1 | 11/2002 | Lang et al. | 600/410 | 2008/0009950 A1 | 1/2008 | Richardson ... 623/20.29 |
| 2002/0183850 A1 | 12/2002 | Felt et al. | 623/20.16 | 2008/0015433 A1 | 1/2008 | Alexander et al. ... 600/427 |
| 2003/0015208 A1 | 1/2003 | Lang et al. | 128/922 | 2008/0025463 A1 | 1/2008 | Lang ... 378/54 |
| 2003/0031292 A1 | 2/2003 | Lang | 378/54 | 2008/0031412 A1 | 2/2008 | Lang et al. ... 378/54 |
| 2003/0045935 A1 | 3/2003 | Angelucci et al. | 623/17.11 | 2008/0058613 A1 | 3/2008 | Lang et al. ... 600/300 |
| 2003/0055500 A1 | 3/2003 | Fell et al. | 623/14.12 | 2008/0058945 A1 | 3/2008 | Hajaj et al. ... 623/20.14 |
| 2003/0055501 A1 | 3/2003 | Fell et al. | 623/14.12 | 2008/0119940 A1 | 5/2008 | Otto et al. ... 623/20.31 |
| 2003/0055502 A1 | 3/2003 | Lang et al. | 623/16.11 | 2008/0170659 A1 | 7/2008 | Lang et al. ... 378/56 |
| 2003/0060882 A1 | 3/2003 | Fell et al. | 623/14.12 | 2008/0172125 A1 | 7/2008 | Ek ... 623/14.12 |
| 2003/0060883 A1 | 3/2003 | Fell et al. | 623/14.12 | 2008/0195108 A1 | 8/2008 | Bhatnagar et al. ... 606/87 |
| 2003/0060884 A1 | 3/2003 | Fell et al. | 623/14.12 | 2008/0195216 A1 | 8/2008 | Philipp ... 623/18.11 |
| 2003/0060885 A1 | 3/2003 | Fell et al. | 623/14.12 | 2008/0215059 A1 | 9/2008 | Carignan et al. ... 606/96 |
| 2003/0063704 A1 | 4/2003 | Lang | 378/54 | 2008/0219412 A1 | 9/2008 | Lang ... 378/207 |
| 2003/0100953 A1 | 5/2003 | Rosa et al. | 623/20.3 | 2008/0243127 A1 | 10/2008 | Lang et al. ... 606/87 |
| 2003/0158606 A1 | 8/2003 | Coon et al. | 623/20.15 | 2008/0275452 A1 | 11/2008 | Lang et al. ... 606/88 |
| 2003/0216669 A1 | 11/2003 | Lang et al. | 600/587 | 2008/0281328 A1 | 11/2008 | Lang et al. ... 606/87 |
| 2003/0225457 A1 | 12/2003 | Justin et al. | 623/20.14 | 2008/0281329 A1 | 11/2008 | Fitz et al. ... 623/17.16 |
| 2003/0236473 A1 | 12/2003 | Dore et al. | 600/587 | 2008/0281426 A1 | 11/2008 | Fitz et al. ... 623/17.16 |
| 2004/0006393 A1 | 1/2004 | Burkinshaw | 623/20.3 | 2009/0076371 A1 | 3/2009 | Lang et al. ... 600/407 |
| 2004/0062358 A1 | 4/2004 | Lang et al. | 378/207 | 2009/0131941 A1 | 5/2009 | Park et al. ... 606/87 |
| 2004/0081287 A1 | 4/2004 | Lang et al. | 378/154 | 2009/0228111 A1 | 9/2009 | Otto ... 623/20.19 |
| 2004/0098132 A1 | 5/2004 | Andriacchi et al. | 623/20.35 | 2009/0276045 A1 | 11/2009 | Lang ... 623/14.12 |
| 2004/0102851 A1 | 5/2004 | Saladino | 623/20.15 | 2009/0306676 A1 | 12/2009 | Lang et al. ... 606/102 |
| 2004/0102852 A1 | 5/2004 | Johnson et al. | 623/20.15 | 2009/0312805 A1 | 12/2009 | Lang et al. ... 606/86 R |
| 2004/0117015 A1 | 6/2004 | Biscup | 623/16.11 | 2010/0054572 A1 | 3/2010 | Tsougarakis et al. ... 382/131 |
| 2004/0122521 A1 | 6/2004 | Lee et al. | 623/20.15 | 2010/0303313 A1 | 12/2010 | Lang et al. ... 382/128 |
| 2004/0133276 A1 | 7/2004 | Lang et al. | 623/14.12 | 2010/0303317 A1 | 12/2010 | Tsougarakis et al. ... 382/128 |
| 2004/0138754 A1 | 7/2004 | Lang et al. | 623/20.14 | 2010/0303324 A1 | 12/2010 | Lang et al. ... 382/131 |
| 2004/0138755 A1 | 7/2004 | O'Connor et al. | 623/20.32 | 2010/0305708 A1 | 12/2010 | Lang et al. ... 623/20.18 |
| 2004/0147927 A1 | 7/2004 | Tsougarakis et al. | 606/53 | 2010/0305907 A1 | 12/2010 | Fitz et al. ... 703/1 |
| 2004/0153079 A1 | 8/2004 | Tsougarakis et al. | 606/77 | 2010/0329530 A1 | 12/2010 | Lang et al. ... 382/131 |
| 2004/0153162 A1 | 8/2004 | Sanford et al. | 623/20.3 | 2010/0331991 A1 | 12/2010 | Wilkinson et al. ... 623/20.32 |
| 2004/0153164 A1 | 8/2004 | Sanford et al. | 623/20.29 | 2011/0029093 A1 | 2/2011 | Bojarski et al. ... 623/20.35 |
| 2004/0167390 A1 | 8/2004 | Alexander et al. | 600/410 | 2011/0066245 A1 | 3/2011 | Lang et al. ... 623/18.11 |
| 2004/0167630 A1 | 8/2004 | Rolston | 623/20.14 | 2011/0071645 A1 | 3/2011 | Bojarski et al. ... 623/20.35 |
| 2004/0193280 A1 | 9/2004 | Webster et al. | 623/20.33 | 2011/0071802 A1 | 3/2011 | Bojarski et al. ... 703/1 |
| 2004/0204644 A1 | 10/2004 | Tsougarakis et al. | 600/410 | 2011/0144760 A1 | 6/2011 | Wong et al. ... 623/20.14 |
| 2004/0204760 A1 | 10/2004 | Fitz et al. | 623/14.12 | 2011/0266265 A1 | 11/2011 | Lang ... 219/121.72 |
| 2004/0204766 A1 | 10/2004 | Siebel | 623/20.31 | 2012/0093377 A1 | 4/2012 | Tsougarakis et al. ... 382/128 |
| 2004/0236424 A1 | 11/2004 | Berez et al. | 623/14.12 | 2012/0191205 A1 | 7/2012 | Bojarski et al. ... 623/20.32 |
| 2005/0010106 A1 | 1/2005 | Lang et al. | 600/425 | 2012/0191420 A1 | 7/2012 | Bojarski et al. ... 703/1 |
| 2005/0015153 A1 | 1/2005 | Goble et al. | 623/23.46 | | | |
| 2005/0021042 A1 | 1/2005 | Marnay et al. | 606/99 | | | |
| 2005/0033424 A1 | 2/2005 | Fell | 623/14.24 | | | |
| 2005/0043807 A1 | 2/2005 | Wood | 623/20.14 | | | |
| 2005/0055028 A1 | 3/2005 | Haines | 606/79 | | | |
| 2005/0078802 A1 | 4/2005 | Lang et al. | 387/207 | | | |
| 2005/0107883 A1 | 5/2005 | Goodfried et al. | 623/20.15 | | | |
| 2005/0107884 A1 | 5/2005 | Johnson et al. | 623/20.15 | | | |
| 2005/0119664 A1 | 6/2005 | Carignan et al. | 606/96 | | | |
| 2005/0125029 A1 | 6/2005 | Bernard et al. | 606/205 | | | |
| 2005/0171612 A1 | 8/2005 | Rolston | 623/20.19 | | | |
| 2005/0203384 A1 | 9/2005 | Sati et al. | 600/426 | | | |
| 2005/0216305 A1 | 9/2005 | Funderud | 705/2 | | | |
| 2005/0226374 A1 | 10/2005 | Lang et al. | 378/54 | | | |
| 2005/0234461 A1 | 10/2005 | Burdulis, Jr. et al. | 606/79 | | | |
| 2005/0267584 A1 | 12/2005 | Burdulis, Jr. et al. | 623/20.19 | | | |
| 2006/0069318 A1 | 3/2006 | Keaveny et al. | 600/300 | | | |
| 2006/0111722 A1 | 5/2006 | Bouadi | 606/79 | | | |
| 2006/0111726 A1 | 5/2006 | Felt et al. | 606/86 | | | |
| 2006/0149374 A1 | 7/2006 | Winslow et al. | 623/17.11 | | | |

FOREIGN PATENT DOCUMENTS

| | | |
|---|---|---|
| CN | 2305966 | 2/1999 |
| DE | 2306552 | 8/1974 |
| DE | 3516743 | 11/1986 |
| DE | 44 34 539 | 4/1996 |
| DE | 19803673 | 8/1999 |
| DE | 19926083 | 12/2000 |
| DE | 10135771 | 2/2003 |
| EP | 0528080 | 2/1993 |
| EP | 0600806 | 6/1994 |
| EP | 0 704 193 | 4/1996 |
| EP | 0626156 | 7/1997 |
| EP | 0613380 | 12/1999 |
| EP | 1074229 | 2/2001 |
| EP | 1077253 | 2/2001 |
| EP | 1120087 | 8/2001 |
| EP | 1129675 | 9/2001 |
| EP | 0732091 | 12/2001 |
| EP | 0896825 | 7/2002 |

| | | |
|---|---|---|
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 1327423 | 7/2003 |
| EP | 0530804 | 6/2004 |
| EP | 1437101 | 7/2004 |
| EP | 1070487 | 9/2005 |
| FR | 2589720 | 5/1987 |
| FR | 2740326 | 4/1997 |
| GB | 1451283 | 9/1976 |
| GB | 2291355 | 1/1996 |
| GB | 2304051 | 3/1997 |
| GB | 2348373 | 10/2000 |
| JP | 56-083343 | 7/1981 |
| JP | 61-247448 | 11/1984 |
| JP | 61-247448 | 11/1986 |
| JP | 1-249049 | 10/1989 |
| JP | 05-184612 | 7/1993 |
| JP | 7-236648 | 9/1995 |
| JP | 8-173465 | 7/1996 |
| JP | 9-206322 | 8/1997 |
| JP | 11-19104 | 1/1999 |
| JP | 11-276510 | 10/1999 |
| WO | WO 87/02882 | 5/1987 |
| WO | WO 90/09769 | 9/1990 |
| WO | WO 93/04710 | 3/1993 |
| WO | WO 93/09819 | 5/1993 |
| WO | WO 93/25157 | 12/1993 |
| WO | WO 95/27450 | 10/1995 |
| WO | WO 95/28688 | 10/1995 |
| WO | WO 95/30390 | 11/1995 |
| WO | WO 95/32623 | 12/1995 |
| WO | WO 96/24302 | 8/1996 |
| WO | WO 97/25942 | 7/1997 |
| WO | WO 97/27885 | 8/1997 |
| WO | WO 97/38676 | 10/1997 |
| WO | WO 97/46665 | 12/1997 |
| WO | WO 98/08469 | 3/1998 |
| WO | WO 98/12994 | 4/1998 |
| WO | WO 98/20816 | 5/1998 |
| WO | WO 98/30617 | 7/1998 |
| WO | WO 98/52498 | 11/1998 |
| WO | WO 99/02654 | 1/1999 |
| WO | WO 99/08598 | 2/1999 |
| WO | WO 99/08728 | 2/1999 |
| WO | WO 99/42061 | 8/1999 |
| WO | WO 99/47186 | 9/1999 |
| WO | WO 99/51719 | 10/1999 |
| WO | WO 00/09179 | 2/2000 |
| WO | WO 00/15153 | 3/2000 |
| WO | WO 00/35346 | 6/2000 |
| WO | WO 00/35646 | 6/2000 |
| WO | WO 00/48550 | 8/2000 |
| WO | WO 00/59411 | 10/2000 |
| WO | WO 00/68749 | 11/2000 |
| WO | WO 00/74554 | 12/2000 |
| WO | WO 00/74741 | 12/2000 |
| WO | WO 01/10356 | 2/2001 |
| WO | WO 01/17463 | 3/2001 |
| WO | WO 01/19254 | 3/2001 |
| WO | WO 01/35968 | 5/2001 |
| WO | WO 01/45764 | 6/2001 |
| WO | WO 01/68800 | 9/2001 |
| WO | WO 01/70142 | 9/2001 |
| WO | WO 01/77988 | 10/2001 |
| WO | WO 01/82677 | 11/2001 |
| WO | WO 01/91672 | 12/2001 |
| WO | WO 02/22013 | 3/2002 |
| WO | WO 02/22014 | 3/2002 |
| WO | WO 02/23483 | 3/2002 |
| WO | WO 02/34310 | 5/2002 |
| WO | WO 02/36147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/061522 | 7/2003 |
| WO | WO 03/099106 | 12/2003 |
| WO | WO 2004/006811 | 1/2004 |
| WO | WO 2004/032806 | 4/2004 |
| WO | WO 2004/043305 | 5/2004 |
| WO | WO 2004/049981 | 6/2004 |
| WO | WO 2004/051301 | 6/2004 |
| WO | WO 2004/073550 | 9/2004 |
| WO | WO 2005/016175 | 2/2005 |
| WO | WO 2005/020850 | 3/2005 |
| WO | WO 2005/051239 | 6/2005 |
| WO | WO 2005/051240 | 6/2005 |
| WO | WO 2005/067521 | 7/2005 |
| WO | WO 2006/058057 | 6/2006 |
| WO | WO 2006/060795 | 6/2006 |
| WO | WO 2006/065774 | 6/2006 |
| WO | WO 2007/041375 | 4/2007 |
| WO | WO 2007/062079 | 5/2007 |
| WO | WO 2007/092841 | 8/2007 |
| WO | WO 2007/109641 | 9/2007 |
| WO | WO 2008/021494 | 2/2008 |
| WO | WO 2008/157412 | 12/2008 |
| WO | WO 2009/140294 | 11/2009 |
| WO | WO 2010/099231 | 9/2010 |
| WO | WO 2010/099353 | 9/2010 |
| WO | WO 2011/028624 | 3/2011 |
| WO | WO 2011/056995 | 5/2011 |
| WO | WO 2011/072235 | 6/2011 |

OTHER PUBLICATIONS

Adam et al., "MR Imaging of the Knee: Three-Dimensional Volume Imaging Combined with Fast Processing,"J. Compt. Asst. Tomogr., 13(6): 984-988 (1989).

Adams et al., "Quantitative Imaging of Osteoarthritis," Semin Arthritis Rheum, 20(6) Suppl. 2: 26-39 (Jun. 1991).

Ahmad et al., "Biomechanical and Topographic Considerations for Autologous Osteochondral Grafting in the Knee," Am J Sports Med, 29(2): 201-206 (Mar.-Apr. 2001).

Alexander, "Estimating the motion of bones from markers on the skin," University of Illinois at Chicago (Doctoral Dissertation) (1998).

Alexander et al., "Correcting for deformation in skin-based marker systems," Proceedings of the 3rd Annual Gait and Clinical Movement Analysis Meeting, San Diego, CA (1998).

Alexander et al., "Internal to external correspondence in the analysis of lower limb bone motion," Proceedings of the 1999 ASME Summer Bioengineering Conference, Big Sky, Montana (1999).

Alexander et al., "State estimation theory in human movement analysis," Proceedings of the ASME International Mechanical Engineering Congress (1998).

Alexander et al., "Optimization techniques for skin deformation," International Symposium on 3-D Human Movement Conference, Chattanooga, TN, (1998).

Alexander et al., "Dynamic Functional Imaging of the Musculoskeletal System," ASME Winter International Congress and Exposition, Nashville, TN (1999).

Allen et al., "Late degenerative changes after meniscectomy 5 factors affecting the knee after operations," J Bone Joint Surg 66B: 666-671 (1984).

Alley et al., "Ultrafast contrast-enhanced three dimensional MR Aagiography: State of the art," Radiographics 18: 273-285 (1998).

Andersson et al., "MacIntosh Arthroplasty in Rheumatoid Arthritis," Acta. Orthrop. Scand. 45(2):245-259 (1974).

Andriacchi, "Dynamics of knee Malalignment," Orthop Clin North Am 25: 395-403 (1994).

Andriacchi, et al., "A point cluster method for in vivo motion analysis: Applied to a study of knee kinematics," J. Biomech Eng 120(12): 743-749 (1998).

Andriacchi, et al., "Methods for evaluating the progression of Osterarthiritis," Journal of Rehabilitation Research and Development 37(2): 163-170 (2000).

Andriacchi et al., "Gait analysis as a tool to assess joint kinetics biomechanics of normal and pathological human articulating joints," Nijhoff, Series E 93: 83-102 (1985).

Andriacchi et al., "In vivo measurement of six-degrees-of-freedom knee movement during functional testing," Transactions of the Orthopedic Research Society 698 (1995).

Aragenson et al., "Is There a Place for Patellofemoral Arthroplasty?," Clinical Orthopaedics and Related Research No. 321, pp. 162-167 (1995).

Aro et al., "Clinical Use of Bone Allografts," Ann Med 25:403-412 (1993).

Bashir, "Validation of Gadolinium-Enhanced MRI of FAF Measurement in Human Cartilage," Intl. Soc. Mag. Resonance Med. (1998).

Beaulieu et al., "Glenohumeral relationships during physiological shoulder motion and stress testing: Initial experience with open MRI and active Scan-25 plane registration," Radiology (1999).

Beaulieu et al., "Dynamic imaging of glenohumeral instability with open MRI," Int. Society for Magnetic Resonance in Medicine Sydney, Australia (1998).

Beckmann et al., "Noninvasive 3D MR Microscopy as Tool in Pharmacological Research: Application to a Model of Rheumatoid Arthritis," Magn Reson Imaging 13(7): 1013-1017 (1995).

Blazina et al., "Patellofemoral replacement: Utilizing a customized femoral groove replacement," 5(1)53-55 (1990).

Blum et al., "Knee Arthroplasty in Patients with Rheumatoid Arthritis," Ann. Rheum. Dis. 33 (1): 1-11 (1974).

Bobic, "Arthoroscopic osteochondral autogaft transplantation in anterior cruciate ligament reconstruction: a preliminary clinical study," Knee Surg Sports Traumatol Arthrosc 3(4): 262-264 (1996).

Boe et al., "Arthroscopic partial meniscectomy in patients aged over 50," J. Bone Joint Surg 68B: 707 (1986).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Borthakur et al., "In Vivo Triple Quantum Filtered Sodium MRI of Human Articular Cartilage," Proc. Intl. Soc. Mag. Resonance Med., 7:549 (1999).

Bregler et al., "Recovering non-rigid 3D shape from image streams," Proc. IEEE Conference on Computer Vision and Pattern Recognition (Jun. 2000).

Brett et al., "Quantitative Analysis of Biomedical Images," Univ. of Manchester, Zeneca Pharmaceuticals, IBM UK, http://www.wiau.man.ac.uk/~ads/imv (1998).

Brittberg et al., "A critical analysis of cartilage repair," Acta Orthop Scand 68(2): 186-191 (1997).

Brittberg et al., "Treatment of deep cartilage defects in the knee with autologous chrondrocyte transplantation," N Engl J Med 331(14): 889-895 (1994).

Broderick et al., "Severity of articular cartilage abnormality in patients with osteoarthritis: evaluation with fast spin-echo MR vs. arthroscopy," AJR 162: 99-103 (1994).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Burgkart et al., "Magnetic Resonance Imaging-Based Assessment of Cartilage Loss in Severe Osteoarthritis," Arth Rheum; 44(9): 2072-2077 (Sep. 2001).

Butterworth et al., "A T1O2 Dielectric-Filled Toroidal Resonator," Proc. Intl. Soc. Mag. Resonance Med., 7:169 (1999).

Butts et al., "Real-Time MR imaging of joint motion on an open MR imaging scanner," Radiological Society of North America, 83rd Scientific Assembly and Annual Meeting, Chicago, IL (1997).

Cameron, et al., "Review of a Failed Knee Replacement and Some Observations on the Design of a Knee Resurfacing Prosthesis," Arch. Orthop Trauma Surg. 97(2):87-89 (1980).

Carano et al., "Estimation of Erosive Changes in Rheumatoid Arthritis by Temporal Multispectral Analysis," Proc. Intl. Soc. Mag. Resonance Med., 7:408 (1999).

Carr et al., "Surface Interpolation with Radial Basis Functions for Medical Imaging," IEEE Transactions on Medical Imaging, IEEE, Inc. New York, vol. 16, pp. 96-107 (Feb. 1997).

Castriota-Scanderbeg et al., "Precision of Sonographic Measurement of Articular Cartilage: Inter-and Intraobserver Analysis," Skeletal Radiol 25: 545-549 (1996).

Chan et al., "Osteoarthritis of the Knee: Comparison of Radiography, CT and MR Imaging to Asses Extent and Severity," AJR Am J Roentgenol 157(4): 799-806 (1991).

Clarke et al., "Human Hip Joint Geometry and Hemiarthroplasty Selection," The Hip. C.V. Mosby, St. Louis 63-89 (1975).

Clary et al., "Experience with the MacIntosh Knee Prosthesis," South Med. J. 65(3):265-272 (1972).

Cohen et al., "Knee cartilage topography, thickness, and contact areas from MRI: in-vitro calibration and in-vivo measurements," Osteoarthritis and Cartilage 7: 95-109 (1999).

Conaty, et al., "Surgery of the Hip and Knee in Patients with Rheumatoid Arthritis," J. Bone Joint Surg. Am. 55(2):301-314 (1973).

Creamer et al., "Quantitative Magnetic Resonance Imaging of the Knee: A Method of Measuring Response to Intra-Articular Treatments," Ann Rheum Dis. 378-381 (1997).

Daniel et al., "Breast cancer-gadolinium-enhanced MR imaging with a 0.5T open imager and three-point Dixon technique," Radiology 207(1): 183-190 (1998).

Dardzinski et al., "T1-T2 Comparison in Adult Articular Cartilage," ISMRM Seventh Scientific Meeting, Philadelphia, PA (May 22-28, 1999).

Dardzinski et al., "Entropy Mapping of Articular Cartilage," Proc. Intl. Soc. Mag. Resonance Med., 7:1018 (1999).

DeWinter et al., "The Richards Type II Patellofemoral Arthroplasty", Acta Orthop Scand 2001; 72 (5): 487-490.

Disler, "Fat-suppressed three-dimensional spoiled gradient-recalled MR imaging: assessment of articular and physeal hyaline cartilage," ARJ 169: 1117-1123 (1997).

Disler et al., "Fat-suppressed three-dimensional spoiled gradient-echo MR imaging of hyaline cartilage defects in the knee: comparison with standard MR imaging and arthroscopy," AJR 167: 127-132 (1996).

Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).

Doherty et al., Osteoarthritis, Oxford Textbook of Theumatology, Oxford University Press 959-983 (1993).

Dougados et al., "Longitudinal radiologic evaluation of osteoarthritis of the knee," J Theumatol 19: 378-394 (1992).

Du et al., "Vessel enhancement filtering in three-dimensional MR angiography," J. Magn Res Imaging 5: 151-157 (1995).

Du et al., "Reduction of partial-volume artifacts with zero filled interpolation in three-dimensional MR Angiography," J Magn Res Imaging 4: 733-741 (1994).

Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).

Dumoulin et al., "Real-time position monitoring of invasive devises using magnetic resonance," Magn Reson Med 29: 411-5 (1993).

Dupuy et al., "Quantification of Articular Cartilage in the Knee with Three-Dimensional MR Imaging," Acad Radiol 3: 919-924 (1996).

Eckstein et al., "In vivo reproducibility of three-dimensional cartilage volume and thickness measurements with MR imaging," AJR 170(3): 593-597 (1998).

Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).

Eckstein et al., "Effect of Gradient and Section Orientation on Quantitative Analyses of Knee Joint Cartilage," Journal of Magnetic Resonance Imaging 11: 161-167 (2000).

Eckstein et al., "Effect of Physical Exercise on Cartilage Volume and Thickness In Vivo: an MR Imaging Study," Radiology 207: 243-248 (1998).

Eckstein et al., "Functional Analysis of Articular Cartilage Deformation, Recovery, and Fluid Flow Following Dynamic Exercise In Vivo," Anatomy and Embryology 200: 419-424 (1999).

Eckstein et al., "New Quantitative Approaches With 3-D MRI: Cartilage Morphology, Function and Degeneration," Medical Imaging International (Nov.-Dec. 1998).

Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).

Eckstein F, et al., "Accuracy of Cartilage Volume and Thickness Measurements with Magnetic Resonance Imaging," Clin. Orthop. 352: 137-148 (1998).

Eckstein et al., "Magnetic Resonance Chondro-Crassometry (MR CCM): A Method for Accurate Determination of Articular Cartilage Thickness?" Magn. Reson. Med. 35: 89-96 (1996).

Eckstein et al., "The Influence of Geometry on the Stress Distribution in Joints—A Finite Element Analysis," Anat Embryol, 189: 545-552 (1994).

Eckstein et al., "The Morphology of Articular Cartilage Assessed by Magnetic Resonance Imaging: Reproducibility and Anatomical Correlation," Sur. Radiol Anat 16: 429-438 (1994).

Elting et al. "Unilateral frame distraction: proximal tibial valgus osteotomy for medial gonarthritis," Contemp Orthrop 27(6): 522-524 (1993).

Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).

Faber et al., "Quantitative Changes of Articular Cartilage Microstructure During Compression of an Intact Joint," Proc. Intl. Soc. Mag. Resonance Med., 7:547 (1999).

Falcao et al., "User-steered image segmentation paradigms: Live wire and live lane," Graphical Models and Image Processing 60: 233-260 (1998).

Felson et al., "Weight Loss Reduces the risk for symptomatic knee osteoarthritis in women: the Framingham study," Ann Intern Med 116: 535-539 (1992).

Gandy et al., "One-Year Longitudinal Study of Femoral Cartilage Lesions in Knee Arthritis," Proc. Intl. Soc. Mag. Resonance Med., 7:1032 (1999).

Garrett, "Osteochondral allografts for reconstruction of articular defects of the knee," Instr Course Lect 47: 517-522 (1998).

Gerscovich, "A Radiologist's Guide to the Imaging in the Diagnosis and Treatment of Developmental Dysplasia of the Hip," Skeletal Radiol 26: 447-456 (1997).

Ghelman, M.D., et al., "Kinematics of the Knee After Prosthetic Replacements", Clin. Orthop. 1975 May: (108): 149-157.

Ghosh et al., "Watershed Segmentation of High Resolution Articular Cartilage Images for Assessment of Osteoarthritis," International Society for Magnetic Resonance in Medicine, Philadelphia, (1999).

Glaser et al., "Optimization and Validation of a Rapid Highresolution T1-W 3-D Flash Waterexcitation MR Sequence For the Quantitative Assessment of Articular Cartilage Volume And Thickness," Magnetic Resonance Imaging 19: 177-185 (2001).

Goodwin et al., "MR Imaging of Articular Cartilage: Striations in the Radial Layer Reflect the Fibrous Structure of Cartilage," Proc. intl. Soc. Mag. Resonance Med., 7:546 (1999).

Gouraud, "Continuous shading of curved surfaces," IEEE Trans on Computers C-20(6) (1971).

Graichen et al., "Three-Dimensional Analysis of the Width of the Subacromial Space in Healthy Subjects and Patients With Impingement Syndrome," American Journal of Roentgenology 172: 1081-1086 (1999).

Hall et al., "Quantitative MRI for Clinical Drug Trials of Joint Diseases; Virtual Biopsy of Articular Cartilage" NIH-FDA Conf. On Biomarkers and Surrogate Endpoints: Advancing Clinical Research and Applications (1998).

Hardy et al., "Measuring the Thickness of Articular Cartilage From MR Images," J. Magnetic Resonance Imaging 13 (2001).

Hardy et al., "The Influence of the Resolution and Contrast on Measuring the Articular Cartilage Volume in Magnetic Resonance Images" Magn Reson Imaging. 18(8): 965-972 (Oct. 2000).

Hargreaves et al., "MR Imaging of Articular Cartilage Using Driven Equilibrium," Magnetic Resonance in Medicine 42(4): 695-703 (Oct. 1999).

Hargreaves et al., "Technical considerations for DEFT imaging," International Society for Magnetic Resonance in Medicine, Sydney, Australia (Apr. 17-24, 1998).

Hargreaves et al., "Imaging of articular cartilage using driven equilibrium," International Society for Magnetic Resonance in Medicine, Sydney, Australia (Apr. 17-24, 1998).

Hastings et al., "Double Hemiarthroplasty of the Knee in Rheumatoid Arthritis, A Survey of Fifty Consecutive Cases," J. Bone Joint Surg. Br. 55(1):112-118 (1973).

Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).

Haut et al., "A High Accuracy Three-Dimensional Coordinate Digitizing System for Reconstructing the Geometry of Diarthrodial Joints," J. Biomechanics 31: 571-577 (1998).

Hayes et al., "Evaluation of Articular Cartilage: Radiographic and Cross-Sectional Imaging Techniques," Radiographics 12: 409-428 (1992).

Henderson et al., "Experience with the Use of the Macintosh Prosthesis in Knees of Patients with Pheumatoid Arthritis," South. Med. J. 62(11):1311-1315 (1969).

Herberhold et al., "An MR-Based Technique for Quantifying the Deformation of Articular Cartilage During Mechanical Loading in an Intact Cadaver Joint," Magnetic Resonance in Medicine 39(5): 843-850 (1998).

Herberhold et al., "In Situ Measurement of Articular Cartilage Deformation in Intact Femorapatellar Joints Under Static Loading," Journal of biomechanics 32: 1287-1295 (1999).

Henkelman et al., "Anisotropy of NMR properties of tissues," Magn Res Med. 32: 592-601 (1994).

Herrmann et al., "High Resolution Imaging of Normal and Osteoarthritic Cartilage with Optical Coherence Tomography," J. Rheumatoil 26: 627-635 (1999).

High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).

Hohe et al., "Surface Size, Curvature Analysis, and Assessment of Knee Joint Incongruity With MR Imaging In Vivo," Magnetic Resonance in Medicine, 47: 554-561 (2002).

Holdsworth et al., "Benefits of Articular Cartilage Imaging at 4 Tesla: An In Vivo Study of Normal Volunteers," Proc. Intl. Soc. Mag. Resonance Med., 7:1028 (1999).

Hughes et al., "Technical Note: A Technique for Measuring the Surface Area of Articular Cartilage in Acetabular Fractures," Br. J. Radiol; 67: 584-588 (1994).

Husmann et al., "Three-Dimensional Morphology of the Proximal Femur," J. Arthroplasty; 12(4): 444-450 (Jun 1997).

Hyhlik-Durr et al., "Precision of Tibial Cartilage Morphometry with a coronal water-excitation MR sequence," European Radiology 10(2): 297-303 (2000).

Ihara H., "Double-Contrast CT Arthrography of the Cartilage of the Patellofemoral Joint," Clin. Orthop.; 198: 50-55 (Sep. 1985).

Iida et al., "Socket Location in Total Hip Replacement: Preoperative Computed Tomography and Computer Simulation" Acta Orthop Scand; 59(1): 1-5 (1998).

Irarrazabal et al., "Fast three-dimensional magnetic resonance imaging," Mag Res. Med. 33: 656-662 (1995).

Jessop et al., "Follow-up of the MacIntosh Arthroplasty of the Knee Joint," Rheumatol Phys. Med. 11(5):217-224 (1972).

Johnson et al., "The distribution of load across the knee. A comparison of static and dynamic measurements," J. Bone Joint Surg 62B: 346-349 (1980).

Johnson, "In vivo contact kinematics of the knee joint: Advancing the point cluster technique," Ph.D. Thesis, University of Minnesota (1999).

Johnson et al., "Development of a knee wear method based on prosthetic in vivo slip velocity," Transaction of the Orthopedic Research Society, 46th Annual Meeting (Mar. 2000).

Jonsson et al., "Precision of Hyaline Cartilage Thickness Measurements," Acta Radiol 1992; 33(3): 234-239 (1992).

Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).

Karvonen et al., "Articular Cartilage Defects of the Knee: Correlation Between Magnetic Resonance Imaging and Gross Pathology," Ann Rheum Dis. 49: 672-675 (1990).

Kass et al., "Snakes: Active contour models.," Int J Comput Vision 1: 321-331 (1988).

Kates, et al., "Experiences of Arthroplasty of the Rheumatoid Knee Using MacIntosh Prostheses," Ann. Rheum. Dis. 28(3):328 (1969).

Kay et al., The MacIntosh Tibial Plateau Hemiprosthesis for the Rheumatoid Knee, J. Bone Joint Surg. Br. 54(2):256-262 (1972).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Klosterman et al., "T2 Measurements in Adult Patellar Cartilage at 1.5 and 3.0 Tesla," ISMRM Seventh Scientific Meeting, Philadelphia, PA, (May 22-28, 1999).

Knauss et al., "Self-Diffusion of Water in Cartilage and Cartilage Components as Studied by Pulsed Field Gradient NMR," Magnetic Resonance in Medicine 41:285-292 (1999).

Koh et al., "Visualization by Magnetic Resonance Imaging of Focal Cartilage Lesions in the Excised Mini-Pig Knee," J. Orthop. Res; 14(4): 554-561 (Jul. 1996).

Korhonen et al., "Importance of the Superficial Tissue Layer for the Indentation Stiffness of Articular Cartilage," Med. Eng. Phys; 24(2): 99-108 (Mar. 2002).

Korkala et al., "Autogenous Osteoperiosteal Grafts in the Reconstruction of Full-Thickness Joint Surface Defects," Int. Orthop.; 15(3): 233-237 (1991).

Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).

Kwak et al., "Anatomy of Human Patellofemoral Joint Articular Cartilage: Surface Curvature Analysis," J. Orthop. Res.; 15: 468-472 (1997).

LaFortune et al., "Three dimensional kinematics of the human knee during walking," J. Biomechanics 25: 347-357 (1992).

Lam et al., "X-Ray Diagnosis: A Physician's Approach", Editor Lam, 1998, Springer-Verlag publishers, Title page and Table of Contents pgs. Only (ISBN 9813083247).

Lang et al., "Functional joint imaging: a new technique integrating MRI and biomotion studies," International Society for Magnetic Resonance in Medicine, Denver (Apr. 18-24, 2000).

Lang et al., Risk factors for progression of cartilage loss: a longitudinal MRI study. European Society of Musculoskeletal Radiology, 6th Annual Meeting, Edinburgh, Scotland (1999).

Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).

Ledingham et al., "Factors affecting radiographic progression of knee osteoarthritis," Ann Rheum Dis 54: 53-58 (1995).

Leenslag et al., "A Porous Composite for Reconstruction of Meniscus Lesions," Biological and Biomechanical Perform. of Biomaterials, Elsevier Science Publishers Amsterdam pp. 147-152 (1986).

Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).

Li et al., A Boundary Optimization Algorithm for Delineating Brain Objects from CT Scans: Nuclear Science Symposium and Medical Imaging Conference 1993 IEEE Conference Record, San Francisco, CA (1993).

Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).

Lorensen et al., "Marching cubes: a high resolution 3d surface construction algorithm," Comput Graph 21: 163-169 (1987).

Losch et al., "A non-invasive technique for 3-dimensional assessment of articular cartilage thickness based on MRI part 1: development of a computational method," Magn Res Imaging 15(7): 795-804 (1997).

Lu et al., "Bone position estimation from skin marker co-ordinates using globals optimization with joint constraints," J Biomechanics 32: 129-134 (1999).

Lucchetti et al., "Skin movement artifact assessment and compensation in the estimation of knee-joint kinematics," J Biomechanics 31: 977-984 (1998).

Lusse et al., "Measurement of Distribution of Water Content of Human Articular Cartilage Based on Transverse Relaxation Times: An In Vitro Study," Seventh Scientific Meeting of ISMRM, p. 1020 (1999).

Lynch et al., "Cartilage segmentation of 3D MRI scans of the osteoarthritic knee combining user knowledge and active contours," Proc. SPIE 3979 Medical Imaging, San Diego (Feb. 2000).

MacIntosh, "Arthroplasty of the Knee in Rheumatoid Arthritis," Proceedings and Reports of Councils and Assotions, J. Bone & Joint Surg., vol. 48B No. (1): 179 (Feb. 1996).

MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).

MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).

MacIntosh, "Hemiarthroplasty of the Knee Using a Space Occupying Prosthesis for Painful Varus and Valgus Deformities," J. Bone Joint Surg. Am. Dec. 1958:40-A:1431.

Maki et al., "SNR improvement in NMR microscopy using DEFT," J Mag Res (1988).

Marshall et al., "Quantitation of Articular Cartilage Using Magnetic Resonance Imaging and Three-Dimensional Reconstruction," J. Orthop. Res.; 13: 814-823 (1995).

Mattila et al., "Massive Osteoarticular Knee Allografts: Structural Changes Evaluated with CT," Radiology; 196: 657-660 (1995).

McCollum et al., "Tibial Plateau Prosthesis in Arthroplasty of the Knee," J. Bone Joint Surg. Am. 1970 52(4):827-8 (Feb. 1996).

McKeever, "The Classic Tibial Plateau Prosthesis," Clin. Orthop. Relat. Res. (192):3-12 (1985).

Merkle et al., "A Transceiver Coil Assembly for Hetero-Nuclear Investigations of Human Breast At 4T," Proc. Intl. Soc. Mag. Resonance Med., 7:170 (1999).

Meyer et al., "Simultaneous spatial and spectral selective excitation," Magn Res Med 15: 287-304 (1990).

Mills et al., "Magnetic Resonance Imaging of the Knee: Evaluation of Meniscal Disease," Curr. Opin. Radiol. 4(6): 77-82 (1992).

Milz et al., "The Thickness of the Subchondral Plate and Its Correlation with the thickness of the Uncalcified Articular Cartilage in the Human Patella," Anat. Embryol.; 192: 437-444 (1995).

Modest et al., "Optical Verification of a Technique for In Situ Ultrasonic Measurement of Articular Cartilage Thickness," J. Biomechanics 22(2): 171-176 (1989).

Mollica et al., "Surgical treatment of arthritic varus knee by tibial corticotomy and angular distraction with an external fixator," Ital J Orthrop Traumatol 18(1): 17-23 (1992).

Moussa, "Rotational Malalignment and Femoral Torsion in Osteoarthritic Knees with Patellofemoral Joint Imvolvement: A Ct Scan Study," Clin. Orthop.; 304: 176-183 (Jul. 1994).

Mundinger et al., "Magnetic Resonance Tomography in the Diagnosis of Peripheral Joints," Schweiz Med. Wochenschr. 121(15): 517-527 (1991).

Myers et al., "Experimental Assessment by High Frequency Ultrasound of Articular Cartilage Thickness and Osteoarthritic Changes," J. Rheumatol; 22: 109-116 (1995).

Nelson et al., "Arthroplasty and Arthrodesis of the Knee Joint," Orthop. Clin. North Am. 2 (1): 245-64 (1971).

Nieminen et al., "T2 Indicates Incompletely the Biomechanical Status of Enzymatically Degraded Articular Cartilage of 9.4T," Proc. Intl. Soc. Mag. Resonance Med., 7:551 (1999).

Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).

Nizard, "Role of tibial osteotomy in the treatment of medical femorotibial osteoarthritis," Rev Rhum Engl Ed 65(7-9): 443-446 (1998).

Noll et al., "Homodyne detection in magnetic resonance imaging," IEEE Trans Med Imag 10(2): 154-163 (1991).

Ogilvie-Harris et al., "Arthroscopic management of the degenerative knee," Arthroscopy 7: 151-157 (1991).

Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).

Pearle et al., "Use of an external MR-tracking coil for active scan plane registration during dynamic Musculoskeletal MR imaging in a vertically open MR unit," American Roentgen Ray Society, San Francisco, CA (1998).

Peterfy et al., "Quantification of the volume of articular cartilage in the carpophalangeal joints of the hand: accuracy and precision of three-dimensional MR imaging," AJR 165: 371-375 (1995).

Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).

Peterfy et al., "Quantification of articular cartilage in the knee with pulsed saturation transfer subtraction and fat-suppressed MR imaging: optimization and validation," Radiology 192(2): 485-491 (1994).

Peterfy et al., "Emerging Applications of Magnetic Resonance Imaging in the Evaluation of Articular Cartilage," Radiol Clin North Am.; 34(2): 195-213 (Mar. 1996).

Pilch et al., "Assessment of Cartilage Volume in the Femorotibial Joint With Magnetic Resonance Imaging and 3D Computer Reconstruction," J. Rheumatol. 21(12): 2307-2319 (1994).

Piplani et al., "Articular cartilage volume in the knee: semiautomated determination from three-dimensional reformations of MR images," Radiology 198: 855-859 (1996).

Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).

Porter et al., "MacIntosh Arthroplasty: A Long-Term Review," J. R. Coll. Surg. Edin. (192):199-201 (1988).

Potter, "Arthroplasty of the Knee With Tibial Metallic Implants of the McKeever and MacIntosh Design," Sug. Clin. North Am. 49(4):903-915 (1969).

Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).

Potter et al., "Magnetic resonance imaging of articular cartilage in the knee: an evaluation with use of fast-spin-echo imaging," J Bone Joint Surg 80-A(9): 1276-1284 (1998).

Potter et al., "Sensitivity of Quantitative NMR Imaging to Matrix Composition in Engineered Cartilage Tissue" Proc. Intl. Soc. Mag. Resonance Med., 7:552 (1999).

Probst et al., "Technique for Measuring the Area of Canine Articular Surfaces," Am. J. Vet. Res. 48(4): 608-609 (1987).

Prodromos et al., "A relationship between gait and clinical changes following high tibial osteotomy," J Bone Joint Surg 67A: 1188-1194 (1985).

Radin et al., "Mechanical Determination of Osteoarthrosis," Sem Arthr Rheum 21(3): 12-21 (1991).

Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).

Ranawat et al., "MacIntosh Hemiarthroplasty in Rheumatoid Knee," Acta Orthop Belg., 39 (1): 1-11 (1973).

Recht et al., "Accuracy of fat-suppressed three-dimensional spoiled gradient-echo FLASH MR imaging in the detection of patellofemoral articular cartilage abnormalities," Radiology 198: 209-212 (1996).

Recht et al., "MR imaging of articular cartilage: current status and future directions," AJR 163: 283-290 (1994).

Reiser et al. "Magnetic Resonance in Cartilaginous Lesions of the Knee Joint With Three-Dimensional Gradient-Echo Imaging," Skeletal Radiol. 17(7): 465-471, (1988).

Ritter et al., "Postoperative alignment of total knee replacement," Clin Orthop 299: 153-156 (1994).

Robarts Research Institute.

Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).

Rushfeldt et al., "Improved Techniques for Measuring in Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).

Saied et al., "Assessment of Articular Cartilage and Subchondral Bone: Subtle and Progressive Changes in Experimental Osteoarthritis Using 50 MHz Echography In Vitro," J. Bone Miner Res.; 12(9): 1378-1386 (1997).

Saito et al., "New algorithms for Euclidean distance transformation of an—dimensional digitized picture with applications," Pattern Recognition 27(11): 1551-1565 (1994).

Schipplein et al., "Interaction between active and passive knee stabilizers during level walking," J Orthop Res 9: 113-119(1991).

Schorn et al., "MacIntosh Arthroplasty in Rheumatoid Arthritis," Rheumatol Rehabil. Aug. 1978:17(3): 155-163.

Schouten et al., "A 12 year follow up study in the general population on prognostic factors of cartilage loss in osteoarthritis of the knee," Ann Rheum Dis 51: 932-937 (1992).

Shapiro et al., "In-Vivo Evaluation of Human Cartilage Compression and Recovery using 1H and 23Na MRI," Proc. Intl. Soc. Mag. Resonance Med., 7:548 (1999).

Sharif et al., "Serum hyaluronic acid level as a predictor of disease progression in osteoarthritis of the knee," Arthritis Rheum 38: 760-767 (1995).

Sharma et al., "Knee adduction moment, serum hyaluronic acid level, and disease severity in medial tibiofemoral osteoarthritis," Arthritis and Rheumatism 41(7): 1233-40 (1998).

Shoup et al., "The driven equilibrium Fourier transform NMR technique: an experimental study," J Mag Res p. 8 (1972).

Slemenda et al., "Lower extremity lean tissue mass strength predict increases in pain and in functional impairment in knee osteoarthritis," Arthritis Rheum 39(suppl): S212 (1996).

Slemenda et al., "Lower extremity strength, lean tissue mass and bone density in progression of knee osteoarthritis;" Arthritis Rheum 39(suppl): S169 (1996).

Slone et al., "Body CT: A Practical Approach", Editor Slone, 1999 McGraw-Hill publishers, Title page and Table of Contents pgs. Only (ISBN 007058219).

Solloway et al., "The use of active shape models for making thickness measurements of articular cartilage from MR images," Mag Res Med 37: 943-952 (1997).

Soslowsky et al., "Articular Geometry of the Glenohumeral Joint," Clin. Orthop.; 285: 181-190 (Dec. 1992).

Spoor et al., "Rigid body motion calculated from spatial coordinates of markers," J. Biomechanics 13: 391-393 (1980).

Stammberger et al., "A Method for Quantifying Time Dependent Changes in MR Signal Intensity of Articular Cartilage as a Function of Tissue Deformation in Intact Joints" Medical Engineering & Physics 20: 741-749 (1998).

Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).

Stammberger et al., "Elastic Registration of 3D Cartilage Surfaces From MR Image Data for Detecting Local Changes of the Cartilage Thickness," Magnetic Resonance in Medicine 44: 592-601 (2000).

Stammberger et al., "Determination of 3D cartilage thickness data from MR imaging: computational method and reproducibility in the living," Mag Res Med 41: 529-536 (1999).

Stammberger et al., "Interobserver to reproducibility of quantitative cartilage measurements: Comparison of B-spline snakes and manual segmentation," Mag Res Imaging 17: 1033-1042 (1999).

Stauffer et al., "The MacIntosh Prosthesis. Prospective Clinical and Gait Evaluation," Arch. Surg. 110(6):717-720 (1975).

Steines et al., Segmentation of osteoarthritic femoral cartilage using live wire, Proc. Intl. Soc. Mag. Resonance Med., 8:1022 (2000).

Steines et al., "Segmentation of osteoarthritis femoral cartilage from MR images," CARS—Computer-Assisted Radiology and Surgery, pp. 578-583, San Francisco (2000).

Steines et al., "Measuring volume of articular cartilage defects in osteoarthritis using MRI," ACR 64th Annual Scientific Meeting, Philadelphia, (Oct. 2000).

Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).

Stout et al., "X-Ray Structure Determination: A Practical Guide", 2nd Ed. Editors Stout and Jensen, 1989, John Wiley & Sons, Title page and Table of Contents pgs. Only (ISBN 0471607118).

Taha et al., "Modeling and Design of a Custom Made Cranium Implant for Large Skull Reconstruction Before a Tumor Removal", Phidias Newsletter No. 6, pp. 3, Jun. 6, 2001. Retrieved from the Internet: URL:http://www.materialise.com/medical/files/pdf.

Tebben et al., "Three-Dimensional Computerized Reconstruction. Illustration of Incremental Articula Cartilage Thinning," Invest. Radiol. 32(8): 475-484 (1997).

Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).

Tomasi et al., "Shape and motion from image streams under orthography—a factorization method," Proc. Nat. Acad. Sci. 90(21): 9795-9802 (1993).

Tsai et al., "Application of a flexible loop-gap resonator for MR imaging of articular cartilage at 3.TO," International Society for Magnetic Resonance in Medicine, Denver (Apr. 24-28, 2000).

Tyler et al., "Detection and Monitoring of Progressive Degeneration of Osteoarthritic Cartilage by MRI," Acta Orthop Scand 1995; 66 Suppl. 266: 130-138 (1995).

Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).

Vande Berg et al., "Assessment of Knee Cartilage in Cadavers With Dual-Detector Spiral CT Arthrography and MR Imaging," Radiology,: 222(2): 430-435 (Feb. 2002).

Van der Linden et al., "MR Imaging of Hyaline Cartilage at 0.5 T: A Quantitative and Qualitative in vitro Evaluation of Three Types of Sequences" (Jun. 1998).

Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).

Wang et al., "The influence of walking mechanics and time on the results of proximal tibial osteotomy," J. Bone Joint Surg 72A: 905-909 (1990).

Warfield et al., "Automatic Segmentation of MRI of the Knee," ISMRM Sixth Scientific Meeting and Exhibition p. 563, Sydney, Australia (Apr. 17-24, 1998).

Warfield et al., "Adaptive Template Moderated Spatially Varying Statistical Classification," Proc. First International Conference on Medical Image Computing and Computer Assisted, MICCAI, pp. 231-238 (1998).

Warfield et al., "Adaptive, Template Moderated Spatially Varying Statistical Classification," Medical Image Analysis 4(1): 43-55 (2000).

Waterton et al., "Diurnal variation in the femoral articular cartilage of the knee in young adult humans," Mag Res Med 43: 126-132 (2000).

Waterton et al., "Magnetic Resonance Methods for Measurement of Disease Progression in Rheumatoid Arthritis," Mag. Res. Imaging; 11: 1033-1038 (1993).

Watson et al., "MR Protocols for Imaging the Guinea Pig Knee," Mag. Res. Imaging 15(8): 957-970 (1997).

Wayne et al., "Measurement of Articular Cartilage Thickness in the Articulated Knee," Ann Biomed Eng.; 26(1): 96-102 (1998).

Wayne et al., "Finite Element Analyses of Repaired Articular Surfaces," Proc. Instn. Mech. Eng.; 205(3): 155-162 (1991).

Wolff et al., "Magnetization transfer contrast: MR imaging of the knee," Radiology 179: 623-628 (1991).

Wordsworth et al., "MacIntosh Arthroplasty for the Rheumatoid Knee: A 10-year Follow Up," Ann. Rheum. Dis. 44(11):738-741 (1985).

Worring et al., "Digital curvature estimation. CVGIP," Image Understanding 58(3): 366-382 (1993).

Yan, "Measuring changes in local volumetric bone density," new approaches to quantitative computed tomography, Ph.D. thesis, Dept. of Electrical Engineering, Stanford University (1998).

Yao et al., "Incidental magnetization transfer contrast in fast spin-echo imaging of cartilage," J. Magn Reson Imaging 6(1): 180-184 (1996).

Yao et al., "MR imaging of joints: analytic optimization of GRE techniques at 1.5T," AJR 158(2): 339-345 (1992).

Yasuda et al., "A 10 to 15 year follow up observation of high tibial osteotomy in medial compartment osteoarthritis," Clin Orthop 282: 186-195 (1992).

International Searching Authority, International Search Report—International Application No. PCT/US02/16945, dated Mar. 26, 2003, 6 pages.

International Searching Authority, Invitation to Pay Additional Fees/Partial Search Report—International Application No. PCT/US03/38158, dated Nov. 22, 2004, 8 pages.

International Searching Authority, International Search Report—International Application No. PCT/US03/38158, dated Feb. 23, 2005, 7 pages.

International Searching Authority, European Search Report—Application No. EP 03790194, dated Jul. 13, 2006, 7 pages.

Billet, Philippe, French Version—"Gliding Knee Prostheses—Analysis of Mechanical Failures", Thesis, Medical School of Marseilles, 1982, 64 pages.

Billet, Philippe, Translated Version—"Gliding Knee Prostheses—Analysis of Mechanical Failures", Thesis, Medical School of Marseilles, 1982, 93 pages.

Kaufman et al., "Articular Cartilage Sodium content as a function of compression" Seventh Scientific Meeting of ISMRM, p. 1022, 1999 T. 105, V. III.

Lu et al., "In vitro degradation of porous poly(L-lactic acid) foams", Biomaterials, 21(15):1595-1605, Aug. 2000.

Marler et al., "Soft-Tissue Augmentation with Injectable Alginate and Syngeneic Fibroblasts", Plastic & Reconstructive Surgery, 105(6):2049-2058, May 2000.

Matsen, III et al., "Robotic Assistance in Orthopaedic Surgery: A Proof of Principle Using Distal Femoral Arthroplasty", Clinical Ortho. and Related Research, 296:178-186 (1993).

Minas, "Chondrocyte Implantation in the Repair of Chondral Lesions of the Knee: Economics and Quality of Life", Am. J. Orthop. Nov. 1998; 27: 739-744.

Portheine et al., "CT-Based Planning and Individual Template Navigation in TKA", Navigation and Robotics in Total Joint and Spine Surgery, Springer, 48:336-342 (2004).

Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.

Radermacher, English Translation: Helmholtz Institute of Biomedical Technology, "Computer-Assisted Planning and Execution of Orthopedic Surgery Using Individual Surgical Templates", May 18, 1999.

Radermacher, German Version: Helmholtz Institute of Biomedical Technology, "Computer-Assisted Planning and Execution of Orthopedic Surgery Using Individual Surgical Templates", May 18, 1999.

Radermacher, "Computer Assisted Orthopaedic Surgery With Image Based Individual Templates" Clinical Orthopaedics, Sep. 1998, vol. 354, pp. 28-38.

Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.

Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
Robarts Research Institute, Abstract #1028, T. 163, V.V, 1999.
Sittek et al., "Assessment of Normal Patellar Cartilage Volume and Thickness Using MRI: an Analysis of Currently Available Pulse Sequences", Skeletal Radiol 1996; 25: 55-61.
Tamez-Pena, MRI Isotropic Resolution Reconstruction from two Orthogonal Scans:, Proceedings of the SPIE—The International Society for Optical Engineering SOIE-OMT. vol. 4322, ppl. 87-97, 2001.
Wiese et al., "Biomaterial properties and biocompatibility in cell culture of a novel self-inflating hydrogel tissue expander", J. Biomedical Materials Research Part A, 54(2):179-188, Nov. 2000.
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US2003/32123, dated Mar. 2004, 9 pages.
International Searching Authority, International Search Report—International Application No. PCT/US03/36079, dated Apr. 15, 2004, 7 pages.
International Searching Authority, International Search Report—International Application No. PCT/US04/39616, dated Mar. 28, 2005, 7 pages.
International Searching Authority, Invitation to Pay Additional Fees—International Application No. PCT/US2007/064349 dated Aug. 7, 2007, 8 pages.
International Searching Authority, International Search Report—International Application No. PCT/US04/39714, dated May 13, 2005, together with the Written Opinion of the International Searching Authority, 7 pages.
International Searching Authority, International Search Report—International Application No. PCT/US2005/042421, dated May 18, 2006, together with the Written Opinion of the International Searching Authority, 7 pages.
European Patent Office, European Search Report—Application No. EP 04812273.3-2310, dated Oct. 8, 2007, 5 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/38212, dated Apr. 22, 2008, together with the Written Opinion of the International Searching Authority, 7 pages.
International Searching Authority, International Search Report—International Application No. PCT/US2009/043656, dated Jul. 9, 2009, together with the Written Opinion of the International Searching Authority, 8 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.
Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 3 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office Office, Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.

International Searching Authority, International Preliminary Report on Patentability dated Jun. 5, 2008, International Application No. PCT/US2006/045131, together with the Written Opinion of the International Searching Authority, 6 pages.
United States Patent and Trademark Office, Office Action dated Aug. 5, 2010, pertaining to U.S. Appl. No. 10/997,407, 12 pages.
International Searching Authority, International Search Report—International Application No. PCT/US06/45131, dated Jul. 11, 2007, together with the Written Opinion of the International Searching Authority, 6 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,31, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy and Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.

Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
CAOS, "MIS meets CAOS Spring 2005 Symposium Schedule", *CAOS Spring 2005 Symposium*, pp. 1-9, May 19, 2005.
Chelule et al., "Patient-Specific Template to Preserve Bone Stock in Total Knee Replacement: Preliminary Results", *15th Annual ISTA Symposium*, Sep. 2002, 1 page.
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I—III, MRCAS '94, Pittsburgh, PA, pp. 42-48 (Sep. 22-24, 1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
United States Patent and Trademark Office, Office Action dated Feb. 10, 2011, pertaining to U.S. Appl. No. 12/317,416, 10 pages.

International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 22, 2011, pertaining to U.S. Appl. No. 11/602,713, 10 pages.
United States Patent and Trademark Office, Office Action dated Mar. 2, 2011, pertaining to U.S. Appl. No. 10/752,438, 8 pages.
European Patent Office, Extended European Search Report—European Application No. 10012404.9-2310, dated Apr. 1, 2011, 7 pages.
United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
Sunstein Kann Murphy & Timbers LLP, Preliminary Amendment dated Aug. 12, 2011, pertaining to U.S. Appl. No. 13/017,886, 13 pages.
International Searching Authority, International Search Report—International Application No. PCT/US2010/055483, dated Jul. 28, 2011, together with the Written Opinion of the International Searching Authority, 9 pages.

* cited by examiner

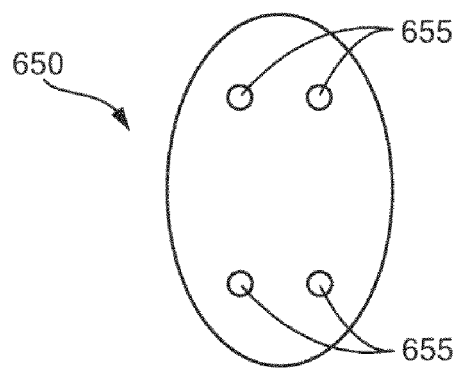 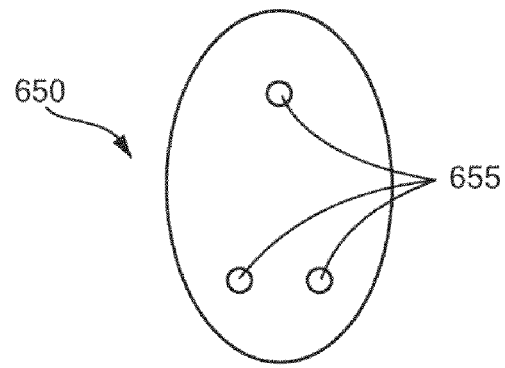
*FIG. 18A*  *FIG. 18B*
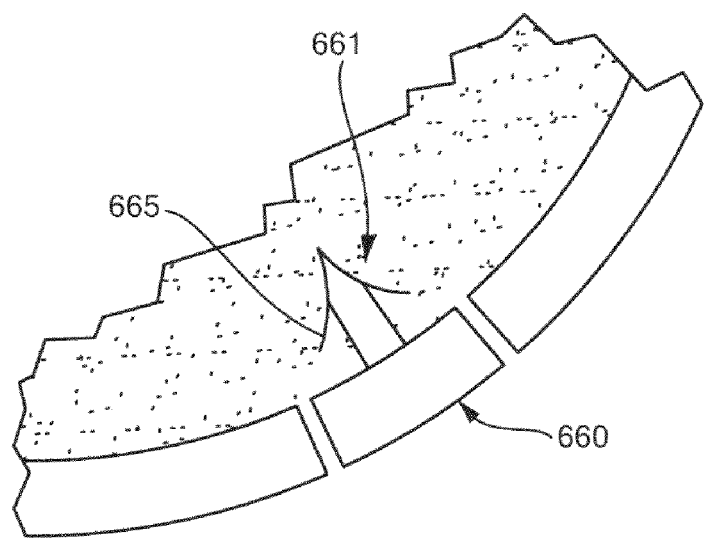
*FIG. 19A*

METHODS AND COMPOSITIONS FOR ARTICULAR REPAIR

CROSS-REFERENCE TO RELATED APPLICATIONS

This application is a continuation of U.S. Ser. No. 10/305,652, filed Nov. 27, 2002, which in turn is a continuation-in-part of U.S. Ser. No. 10/160,667, filed May 28, 2002, which in turn claims the benefit of U.S. Ser. No. 60/293,488 entitled "METHODS To IMPROVE CARTILAGE REPAIR SYSTEMS", filed May 25, 2001, U.S. Ser. No. 60/363,527, entitled "NOVEL DEVICES FOR CARTILAGE REPAIR, filed Mar. 12, 2002 and U.S. Ser. Nos. 60/380,695 and 60/380,692, entitled "METHODS AND COMPOSITIONS FOR CARTILAGE REPAIR," and "METHODS FOR JOINT REPAIR," filed May 14, 2002, all of which applications are hereby incorporated by reference in their entireties.

TECHNICAL FIELD

The present invention relates to orthopedic methods, systems and prosthetic devices and more particularly relates to methods, systems and devices for articular resurfacing.

BACKGROUND

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on joint and site within the joint. In addition, articular cartilage is aneural, avascular, and alymphatic. In adult humans, this cartilage derives its nutrition by a double diffusion system through the synovial membrane and through the dense matrix of the cartilage to reach the chondrocyte, the cells that are found in the connective tissue of cartilage.

Adult cartilage has a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Usually, severe damage or loss of cartilage is treated by replacement of the joint with a prosthetic material, for example, silicone, e.g. for cosmetic repairs, or metal alloys. See, e.g., U.S. Pat. No. 6,383,228, issued May 7, 2002; U.S. Pat. No. 6,203,576, issued Mar. 20, 2001; U.S. Pat. No. 6,126,690, issued Oct. 3, 2000. Implantation of these prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

Further, joint arthroplasties are highly invasive and require surgical resection of the entire or the majority of the articular surface of one or more bones. With these procedures, the marrow space is reamed in order to fit the stem of the prosthesis. The reaming results in a loss of the patient's bone stock.

Osteolysis will frequently lead to loosening of the prosthesis. The prosthesis will subsequently have to be replaced. Since the patient's bone stock is limited, the number of possible replacement surgeries is also limited for joint arthroplasty. In short, over the course of 15 to 20 years, and in some cases shorter time periods, the patients may run out of therapeutic options resulting in a very painful, non-functional joint.

The use of matrices, tissue scaffolds or other carriers implanted with cells (e.g., chrondrocytes, chondrocyte progenitors, stromal cells, mesenchymal stem cells, etc.) has also been described as a potential treatment for cartilage repair. See, also, International Publications WO; 99/51719; WO 01/91672 and WO 01/17463; U.S. Pat. No. 5,283,980 B1, issued Sep. 4, 2001; U.S. Pat. No. 5,842,477, issued Dec. 1, 1998; U.S. Pat. No. 5,769,899, issued Jun. 23, 1998; U.S. Pat. No. 4,609,551, issued Sep. 2, 1986; U.S. Pat. No. 5,041,138, issued Aug. 20, 199; U.S. Pat. No. 5,197,985, issued Mar. 30, 1993; U.S. Pat. No. 5,226,914, issued Jul. 13, 1993; U.S. Pat. No. 6,328,765, issued Dec. 11, 2001; U.S. Pat. No. 6,281,195, issued Aug. 28, 2001; and U.S. Pat. No. 4,846,835, issued Jul. 11, 1989. However, clinical outcomes with biologic replacement materials such as allograft and autograft systems and tissue scaffolds have been uncertain since most of these materials cannot achieve a morphologic arrangement or structure similar to or identical to that of normal, disease-free human tissue. Moreover, the mechanical durability of these biologic replacement materials is not certain.

Despite the large number of studies in the area of cartilage repair, the integration of the cartilage replacement material with the surrounding cartilage of the patient has proven difficult. In particular, integration can be extremely difficult due to differences in thickness and curvature between the surrounding cartilage and/or the underlying subchondral bone and the cartilage replacement material.

Thus, there remains a need for methods and compositions for joint repair, including methods and compositions that facilitate the integration between the cartilage replacement system and the surrounding cartilage.

SUMMARY

The present invention provides novel devices and methods for replacing a portion (e.g., diseased area and/or area slightly larger than the diseased area) of a joint (e.g., cartilage and/or bone) with a non-pliable, non-liquid (e.g., hard) implant material, where the implant—achieves a near anatomic fit with the surrounding structures and tissues. In cases where the devices and/or methods include an element associated with the underlying articular bone, the invention also provides that the bone-associated element achieves a near anatomic alignment with the subchondral bone. The invention also provides for the preparation of an implantation site with a single cut.

In one aspect, the invention includes a method for providing articular replacement material, the method comprising the step of producing articular replacement (e.g., cartilage replacement material) of selected dimensions (e.g., size, thickness and/or curvature).

In another aspect, the invention includes a method of making cartilage repair material, the method comprising the steps of (a) measuring the dimensions (e.g., thickness, curvature and/or size) of the intended implantation site or the dimensions of the area surrounding the intended implantation site; and (b) providing cartilage replacement material that conforms to the measurements obtained in step (a). In certain aspects, step (a) comprises measuring the thickness of the cartilage surrounding the intended implantation site and measuring the curvature of the cartilage surrounding the intended implantation site. In other embodiments, step (a) comprises measuring the size of the intended implantation site and measuring the curvature of the cartilage surrounding the intended implantation site. In other embodiments, step (a) comprises measuring the thickness of the cartilage surrounding the intended implantation site, measuring the size of the intended implantation site, and measuring the curvature of the cartilage surrounding the intended implantation site. In other embodiments, step (a) comprises reconstructing the shape of healthy cartilage surface at the intended implantation site.

In any of the methods described herein, one or more components of the articular replacement material (e.g., the cartilage replacement material) are non-pliable, non-liquid, solid or hard. The dimensions of the replacement material may be selected following intraoperative measurements, for example measurements made using imaging techniques such as ultrasound, MRI, CT scan, x-ray imaging obtained with x-ray dye and fluoroscopic imaging. A mechanical probe (with or without imaging capabilities) may also be used to selected dimensions, for example an ultrasound probe, a laser, an optical probe and a deformable material.

In any of the methods described herein, the replacement material may be selected (for example, from a pre-existing library of repair systems), grown from cells and/or hardened from various materials. Thus, the material can be produced pre- or post-operatively. Furthermore, in any of the methods described herein the repair material may also be shaped (e.g., manually, automatically or by machine), for example using mechanical abrasion, laser ablation, radiofrequency ablation, cryoablation and/or enzymatic digestion.

In any of the methods described herein, the articular replacement material may comprise synthetic materials (e.g., metals, polymers, alloys or combinations thereof) or biological materials such as stem cells, fetal cells or chondrocyte cells.

In another aspect, the invention includes a method of repairing a cartilage in a subject, the method of comprising the step of implanting cartilage repair material prepared according to any of the methods described herein.

In yet another aspect, the invention provides a method of determining the curvature of an articular surface, the method comprising the step of intraoperatively measuring the curvature of the articular surface using a mechanical probe. The articular surface may comprise cartilage and/or subchondral bone. The mechanical probe (with or without imaging capabilities) may include, for example an ultrasound probe, a laser, an optical probe and/or a deformable material.

In a still further aspect, the invention provides a method of producing an articular replacement material comprising the step of providing an articular replacement material that conforms to the measurements obtained by any of the methods of described herein.

In a still further aspect, the invention includes a partial or full articular prosthesis comprising a first component comprising a cartilage replacement material; and a second component comprising one or more metals, wherein said second component has a curvature similar to subchondral bone, wherein said prosthesis comprises less than about 80% of the articular surface. In certain embodiments, the first and/or second component comprises a non-pliable material (e.g., a metal, a polymer, a metal allow, a solid biological material). Other materials that may be included in the first and/or second components include polymers, biological materials, metals, metal alloys or combinations thereof. Furthermore, one or both components may be smooth or porous (or porous coated). In certain embodiments, the first component exhibits biomechanical properties (e.g., elasticity, resistance to axial loading or shear forces) similar to articular cartilage. The first and/or second component can be bioresorbable and, in addition, the first or second components may be adapted to receive injections.

In another aspect, an articular prosthesis comprising an external surface located in the load bearing area of an articular surface, wherein the dimensions of said external surface achieve a near anatomic fit with the adjacent cartilage is provided. The prosthesis of may comprise one or more metals or metal alloys.

In yet another aspect, an articular repair system comprising (a) cartilage replacement material, wherein said cartilage replacement material has a curvature similar to surrounding or adjacent cartilage; and (b) at least one non-biologic material, wherein said articular surface repair system comprises a portion of the articular surface equal to, smaller than, or greater than, the weight-bearing surface is provided. In certain embodiments, the cartilage replacement material is non-pliable (e.g., hard hydroxyapatite, etc.). In certain embodiments, the system exhibits biomechanical (e.g., elasticity, resistance to axial loading or shear forces) and/or biochemical properties similar to articular cartilage. The first and/or second component can be bioresorbable and, in addition, the first or second components may be adapted to receive injections.

In a still further aspect of the invention, an articular surface repair system comprising a first component comprising a cartilage replacement material, wherein said first component has dimensions similar to that of adjacent or surrounding cartilage; and a second component, wherein said second component has a curvature similar to subchondral bone, wherein said articular surface repair system comprises less than about 80% of the articular surface (e.g., a single femoral condyle, tibia, etc.) is provided. In certain embodiments, the first component is non-pliable (e.g., hard hydroxyapatite, etc.). In certain embodiments, the system exhibits biomechanical (e.g., elasticity, resistance to axial loading or shear forces) and/or biochemical properties similar to articular cartilage. The first and/or second component can be bioresorbable and, in addition, the first or second components may be adapted to receive injections. In certain embodiments, the first component has a curvature and thickness similar to that of adjacent or surrounding cartilage. The thickness and/or curvature may vary across the implant material.

In a still further embodiment, a partial articular prosthesis comprising (a) a metal or metal alloy; and (b) an external surface located in the load bearing area of an articular surface, wherein the external surface designed to achieve a near anatomic fit with the adjacent cartilage is provided.

Any of the repair systems or prostheses described herein (e.g., the external surface) may comprise a polymeric material, for example attached to said metal or metal alloy. Further, any of the systems or prostheses described herein can be adapted to receive injections, for example, through an opening in the external surface of said cartilage replacement material (e.g., an opening in the external surface terminates in a plurality of openings on the bone surface). Bone cement, therapeutics, and/or other bioactive substances may be injected through the opening(s). In certain embodiments, bone cement is injected under pressure in order to achieve permeation of portions of the marrow space with bone cement. In addition, any of the repair systems or prostheses described herein may be anchored in bone marrow or in the subchondral bone itself. One or more anchoring extensions (e.g., pegs, etc.) may extend through the bone and/or bone marrow.

In any of the embodiments and aspects described herein, the joint can be a knee, shoulder, hip, vertebrae, elbow, ankle, etc.

In another aspect, a method of designing an articular implant comprising the steps of obtaining an image of a joint, wherein the image includes both normal cartilage and diseased cartilage; reconstructing dimensions of the diseased cartilage surface to correspond to normal cartilage; and designing the articular implant to match the dimensions of the reconstructed diseased cartilage surface or to match an area slightly greater than the diseased cartilage surface is provided. The image can be, for example, MRI, CT, ultrasound, digital tomosynthesis and/or optical coherence tomography images. In certain embodiments, reconstruction is performed by obtaining a parametric surface that follows the contour of the normal cartilage. The parametric surface can include control points that extend the contour of the normal cartilage to the diseased cartilage and/or a B-spline surface. In other embodiments, the reconstruction is performed by obtaining a binary image of cartilage by extracting cartilage from the image, wherein diseased cartilage appears as indentations in the binary image; and performing a morphological closing operation (e.g., performed in two or three-dimensions using a structuring element and/or a dilation operation followed by an erosion operation) to determine the shape of an implant to fill the areas of diseased cartilage.

In yet another aspect, described herein are systems for evaluating the fit of an articular repair system into a joint, the systems comprising one or more computing means capable of superimposing a three-dimensional (e.g., three-dimensional representations of at least one articular structure and of the articular repair system) or a two-dimensional cross-sectional image (e.g., cross-sectional images reconstructed in multiple planes) of a joint and an image of an articular repair system to determine the fit of the articular repair system. The computing means may be: capable of merging the images of the joint and the articular repair system into common coordinate system; capable of selecting an articular repair system having the best fit; capable of rotating or moving the images with respect to each other; and/or capable highlighting areas of poor alignment between the articular repair system and the surrounding articular surfaces. The three-dimensional representations may be generated using a parametric surface representation.

In yet another aspect, surgical tool for preparing a joint to receive an implant are described, for example a tool comprising one or more surfaces or members that conform to the shape of the articular surfaces of the joint (e.g., a femoral condyle and/or tibial plateau of a knee joint). In certain embodiments, the tool comprises lucite and/or silastic. The tool can be re-useable or single-use. In certain embodiments, the tool comprises an array of adjustable, closely spaced pins. In any embodiments described herein, the surgical tool may further comprising an aperture therein, for example one or more apertures having dimensions (e.g., diameter, depth, etc.) smaller or equal to one or more dimensions of the implant and/or one or more apertures adapted to receive one or more injectables. Any of the tools described herein may further include one or more curable (hardening) materials or compositions, for example that are injected through one or more apertures in the tool and which solidify to form an impression of the articular surface.

In still another aspect, method of evaluating the fit of an articular repair system into a joint is described herein, the method comprising obtaining one or more three-dimensional images (e.g., three-dimensional representations of at least one articular structure and of the articular repair system) or two-dimensional cross-sectional images (e.g., cross-sectional images reconstructed in multiple planes) of a joint, wherein the joint includes at least one defect or diseased area; obtaining one or more images of one or more articular repair systems designed to repair the defect or diseased area; and evaluating the images to determine the articular repair system that best fits the defect (e.g., by superimposing the images to determine the fit of the articular repair system into the joint). In certain embodiments, the images of the joint and the articular repair system are merged into common coordinate system. The three-dimensional representations may be generated using a parametric surface representation. In any of these methods, the evaluation may be performed by manual visual inspection and/or by computer (e.g., automated). The images may be obtained, for example, using a C-arm system and/or radiographic contrast.

In yet another aspect, described herein is a method of placing an implant into an articular surface having a defect or diseased area, the method comprising the step of imaging the joint using a C-arm system during placement of the implant, thereby accurately placing the implant into a defect or diseased area.

These and other embodiments of the subject invention will readily occur to those of skill in the art in light of the disclosure herein.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 8A shows an example of normal thickness cartilage in the anterior, central and posterior portion of a femoral condyle 800 and a cartilage defect 805 in the posterior portion of the femoral condyle. FIG. 8B shows an imaging technique or a mechanical, optical, laser or ultrasound device measuring the thickness and detecting a sudden change in thickness indicating the margins of a cartilage defect 810. FIG. 8C shows a weight-bearing surface 815 mapped onto the articular cartilage. Cartilage defect 805 is located within the weight-bearing surface 815. FIG. 8D shows an intended implantation site (stippled line) 820 and cartilage defect 805. The implantation site 820 is slightly larger than the area of diseased cartilage 805. FIG. 8E depicts placement of an exemplary single component articular surface repair system 825. The external surface of the articular surface repair system 826 has a curvature similar to that of the surrounding cartilage 800 resulting in good postoperative alignment between the surrounding normal cartilage 800 and the articular surface repair system 825. FIG. 8F shows an exemplary multi-component articular surface repair system 830. The distal surface of the deep component 832 has a curvature similar to that of the adjacent subchondral bone 835. The external surface of the superficial component 837 has a thickness and curvature similar to that of the surrounding normal cartilage 800. FIG. 8G shows an exemplary single component articular surface repair system 840 with a peripheral margin 845 substantially non-perpendicular to the surrounding or adjacent normal cartilage 800. FIG. 8H shows an exemplary multi-component articular surface repair system 850 with a peripheral margin 845 substantially non-perpendicular to the surrounding or adjacent normal cartilage 800.

FIG. 9, A through E, are schematics depicting exemplary knee imaging and resurfacing.

FIG. 10A is a schematic depicting normal thickness cartilage in the anterior and central and posterior portion of a femoral condyle 1000 and a large area of diseased cartilage 1005 in the posterior portion of the femoral condyle. FIG. 10B depicts placement of a single component articular surface repair system 1010. The implantation site has been prepared with a single cut. The articular surface repair system is not perpendicular to the adjacent normal cartilage 1000. FIG. 10C depicts a multi-component articular surface repair system 1020. The implantation site has been prepared with a single cut. The deep component 1030 has a curvature similar to that of the adjacent subchondral bone 1035. The superficial component 1040 has a curvature similar to that of the adjacent cartilage 1000.

FIG. 11A shows an exemplary a single component articular surface repair system 1100 with varying curvature and radii. In this case, the articular surface repair system is chosen to include convex and concave portions. Such devices can be preferable in a lateral femoral condyle or small joints such as the elbow joint.

FIGS. 17B-D show various cross-sectional representations of the pegs: FIG. 17B shows a peg having a groove; FIG. 17C shows a peg with radially-extending arms that help anchor the device in the underlying bone; and FIG. 17D shows a peg with multiple grooves or flanges.

FIGS. 18A and B depict an overhead view of an exemplary implant 650 with multiple anchoring pegs 655 and depict how the pegs are not necessarily linearly aligned along the longitudinal axis of the device.

FIG. 19A-E depict an exemplary implant 660 having radially extending arms 665. FIG. 19B-E are overhead views of the implant showing that the shape of the peg need not be conical.

DETAILED DESCRIPTION OF THE INVENTION

Figure 1:
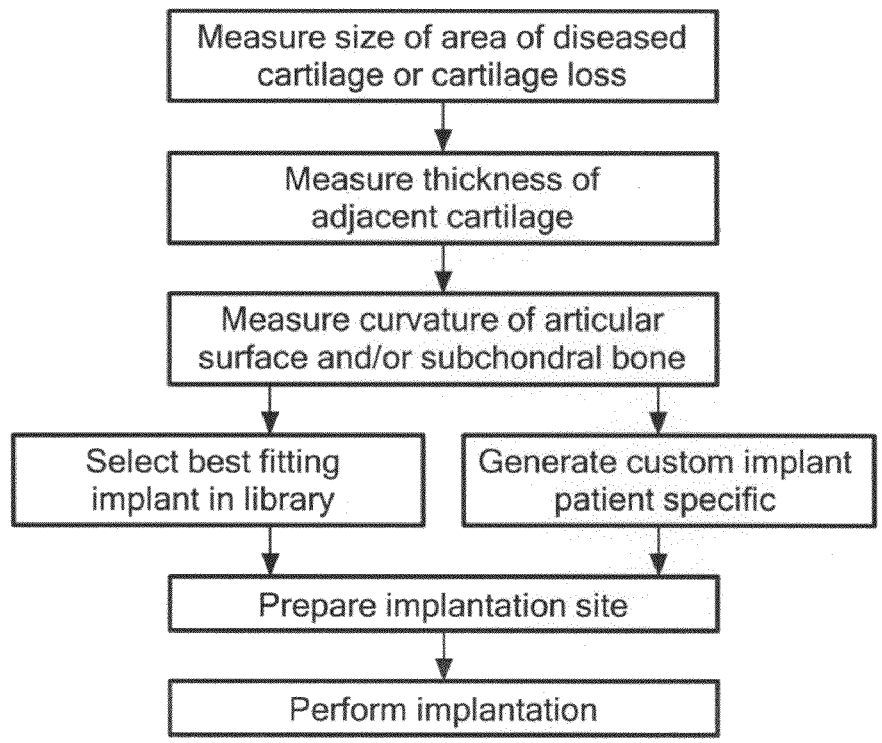
FIG. 1 is a flowchart depicting various methods of the present invention including, measuring the size of an area of diseased cartilage or cartilage loss, measuring the thickness of the adjacent cartilage, and measuring the curvature of the articular surface and/or subchondral bone. Based on this information, a best fitting implant can be selected from a library of implants or a patient specific custom implant can be generated. The implantation site is subsequently prepared and the implantation is performed.
Figure 2:
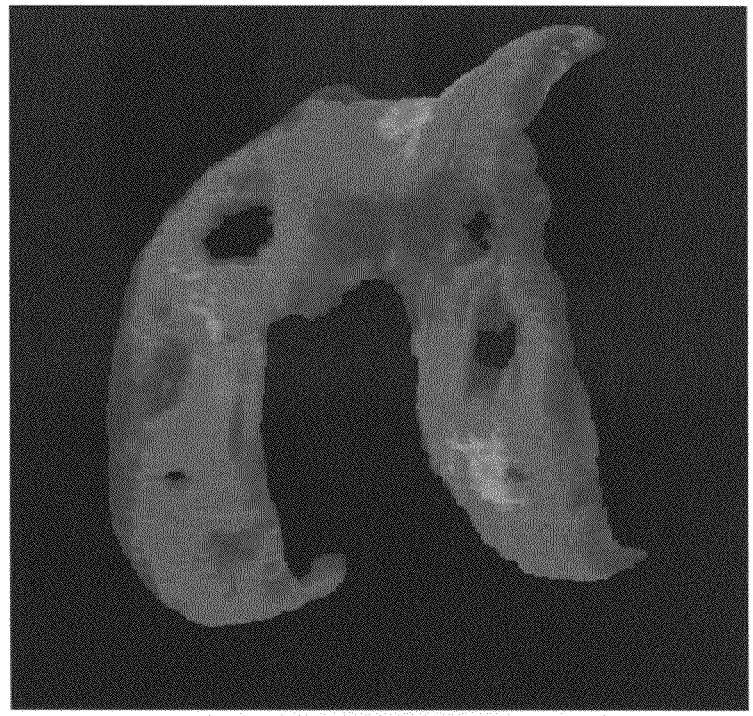
FIG. 2 is a color reproduction of a three-dimensional thickness map of the articular cartilage of the distal femur. Three-dimensional thickness maps can be generated, for example, from ultrasound, CT or MRI data. Dark holes within the substances of the cartilage indicate areas of full thickness cartilage loss.
Figure 3:
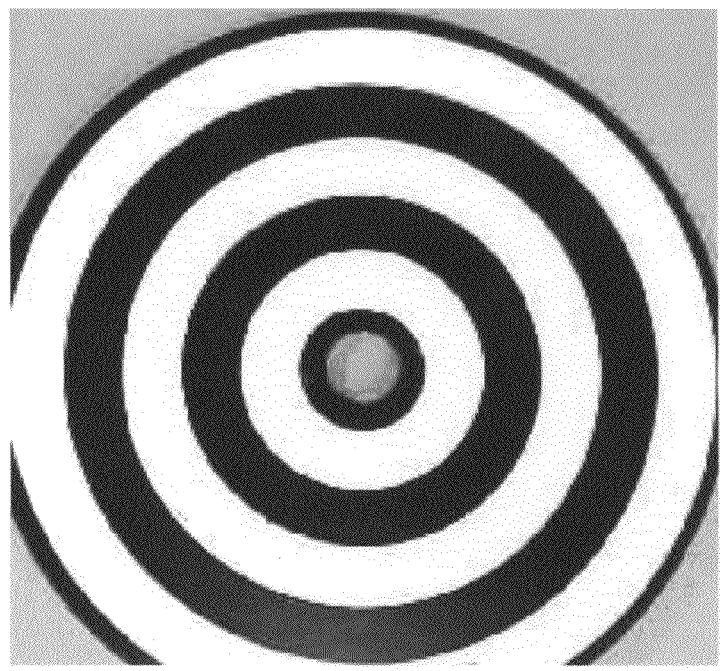
FIG. 3 shows an example of a Placido disc of concentrically arranged circles of light.
Figure 4:
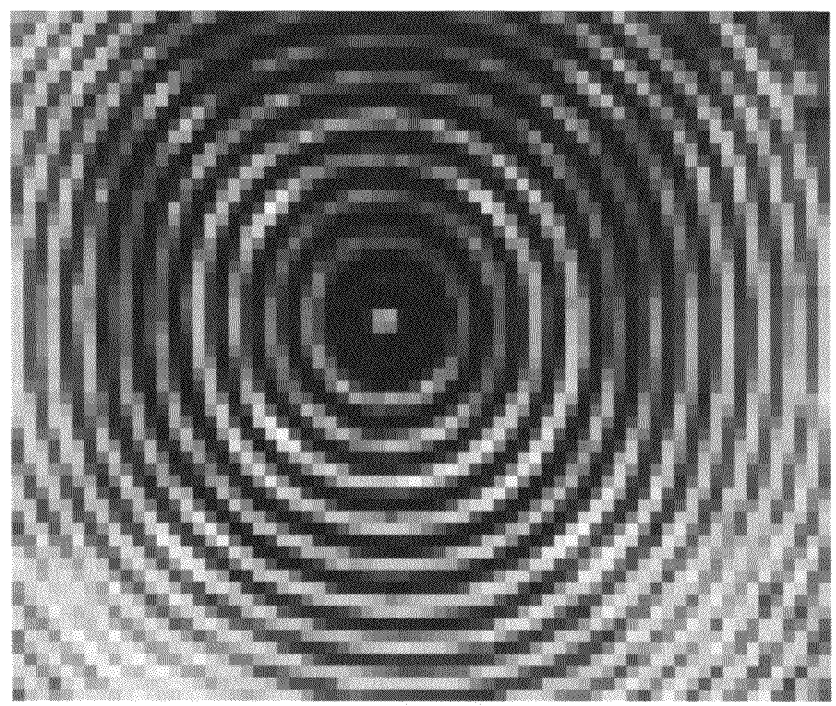
FIG. 4 shows an example of a projected Placido disc on a surface of fixed curvature.
Figure 5:
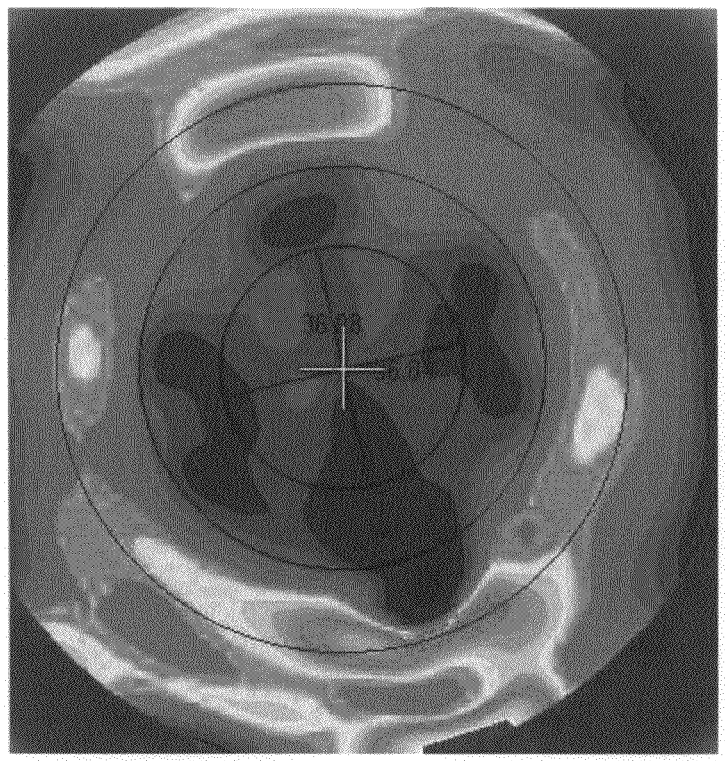
FIG. 5 shows an example of a 2D color-coded topographical map of an irregularly curved surface.
Figure 6:
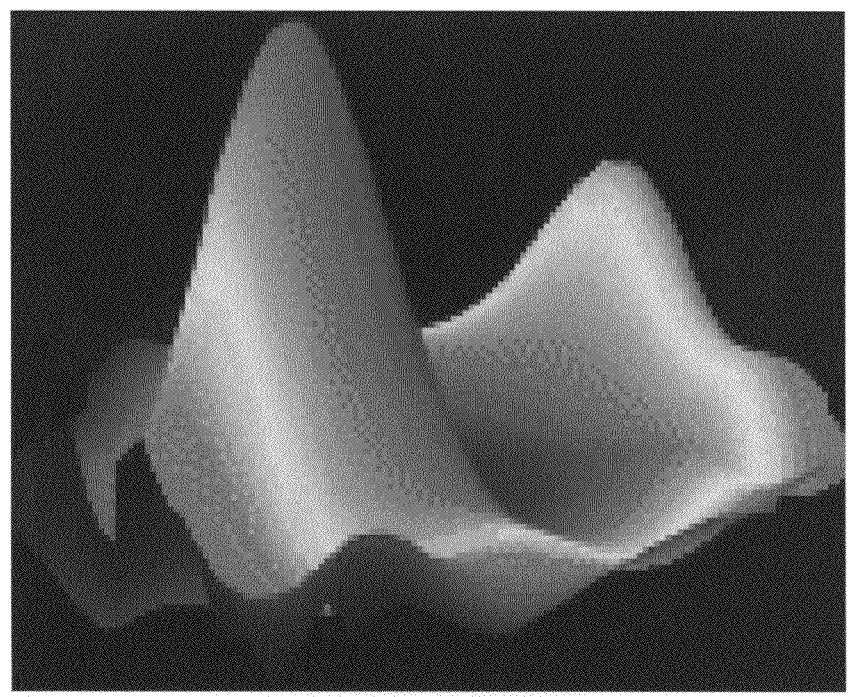
FIG. 6 shows an example of a 3D color-coded topographical map of an irregularly curved surface.
Figure 7:
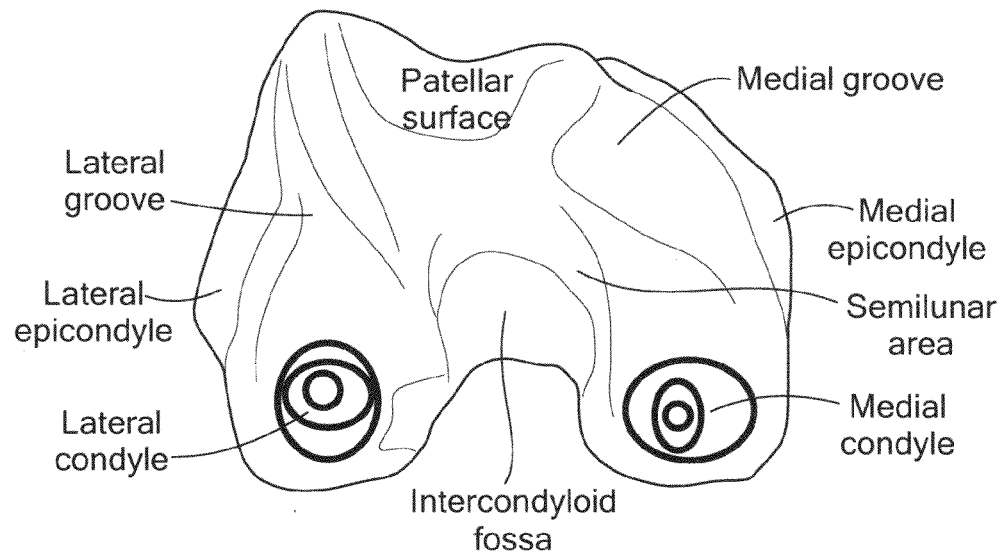
FIG. 7 shows a reflection resulting from a projection of concentric circles of light (Placido Disk) on each femoral condyle, demonstrating the effect of variation in surface contour on the reflected circles.
Figure 8A:
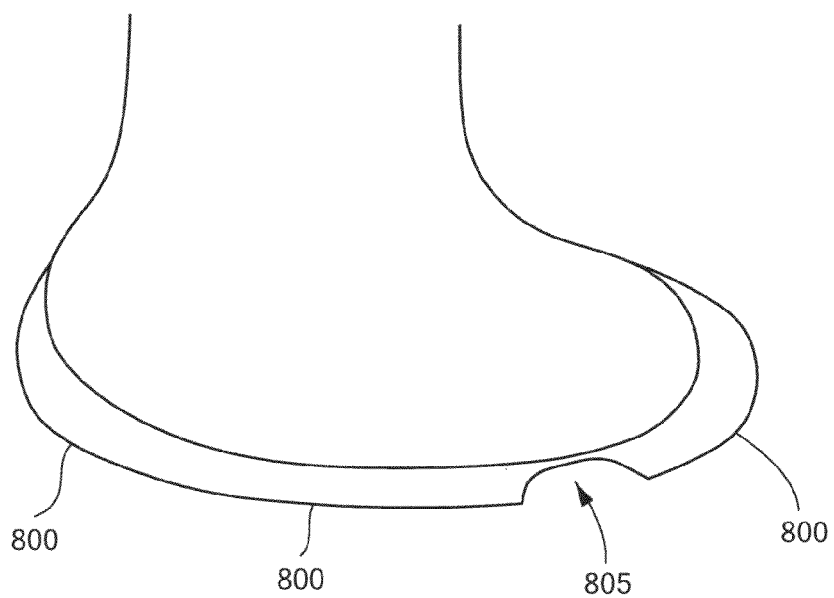
FIG. 8A-H are schematics of various stages of knee resurfacing.
Figure 8B:
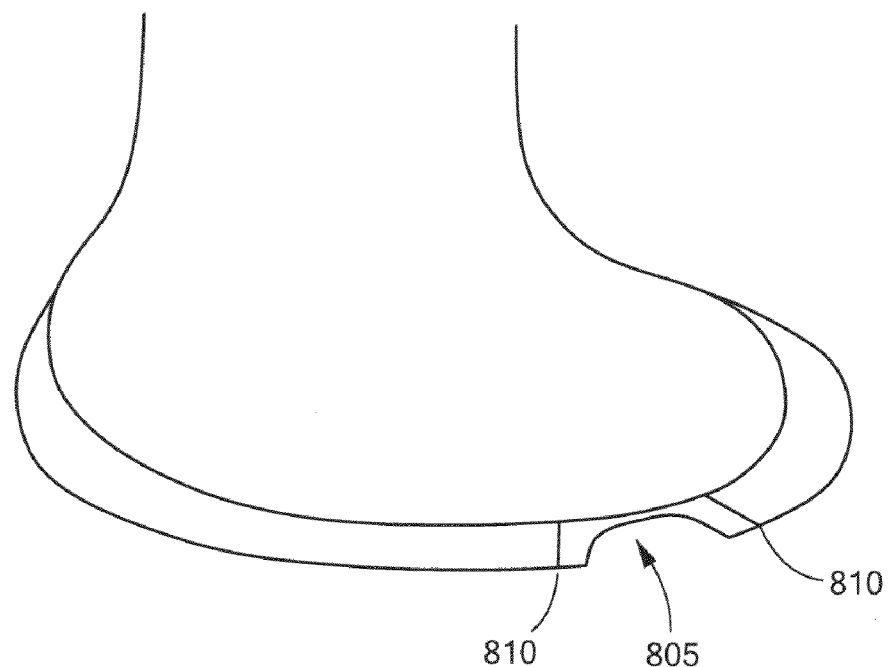
Figure 8C:
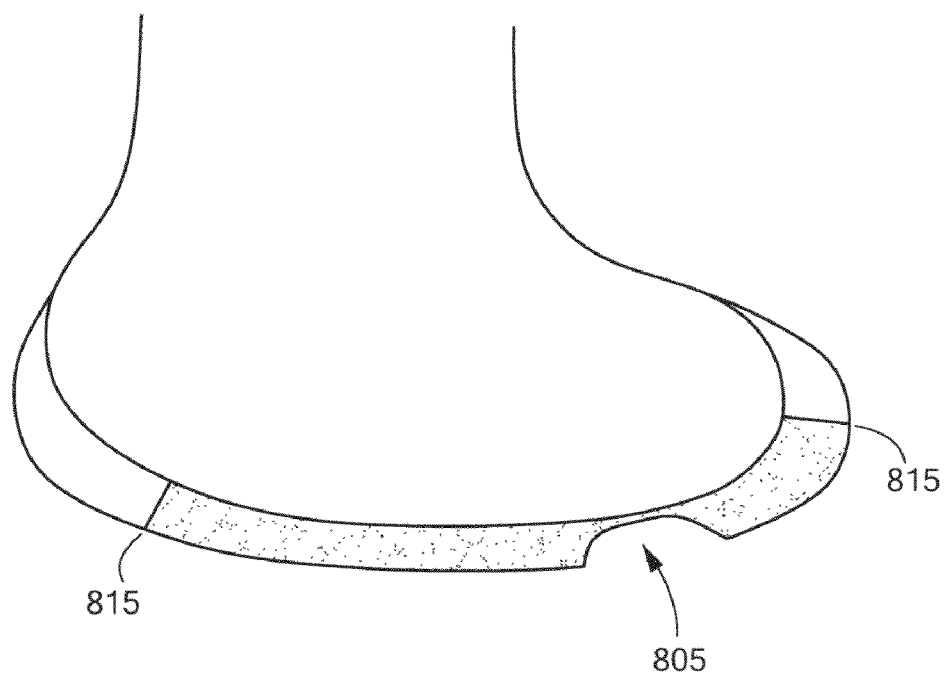
Figure 8D:
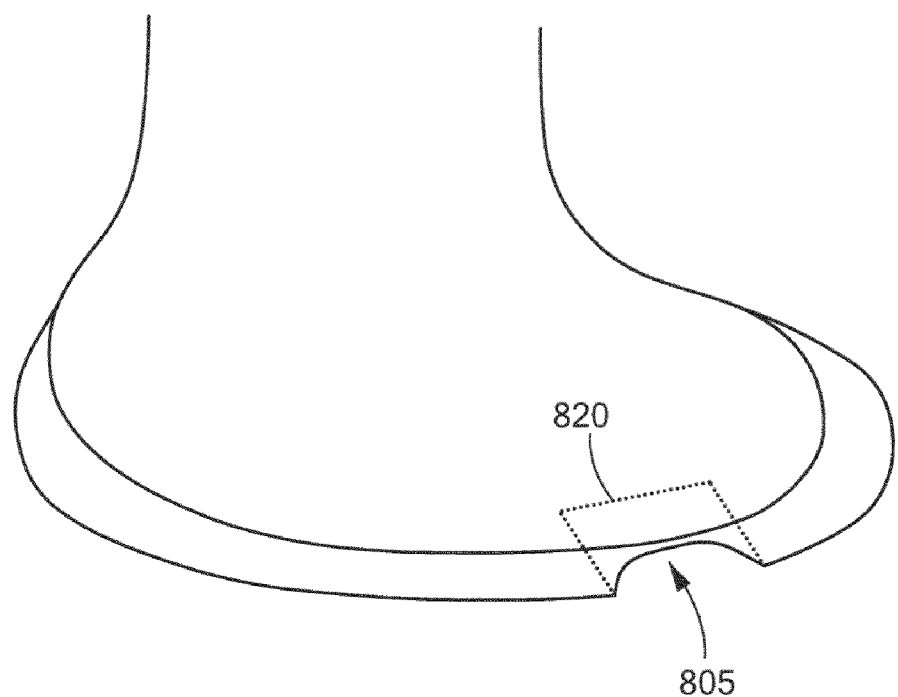
Figure 8E:
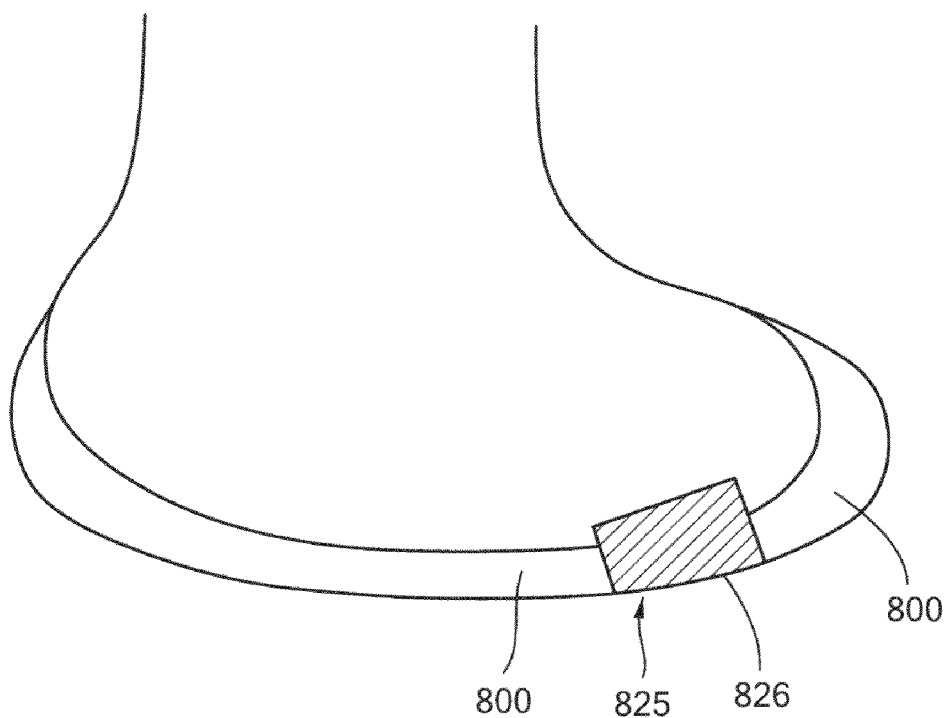
Figure 8F:
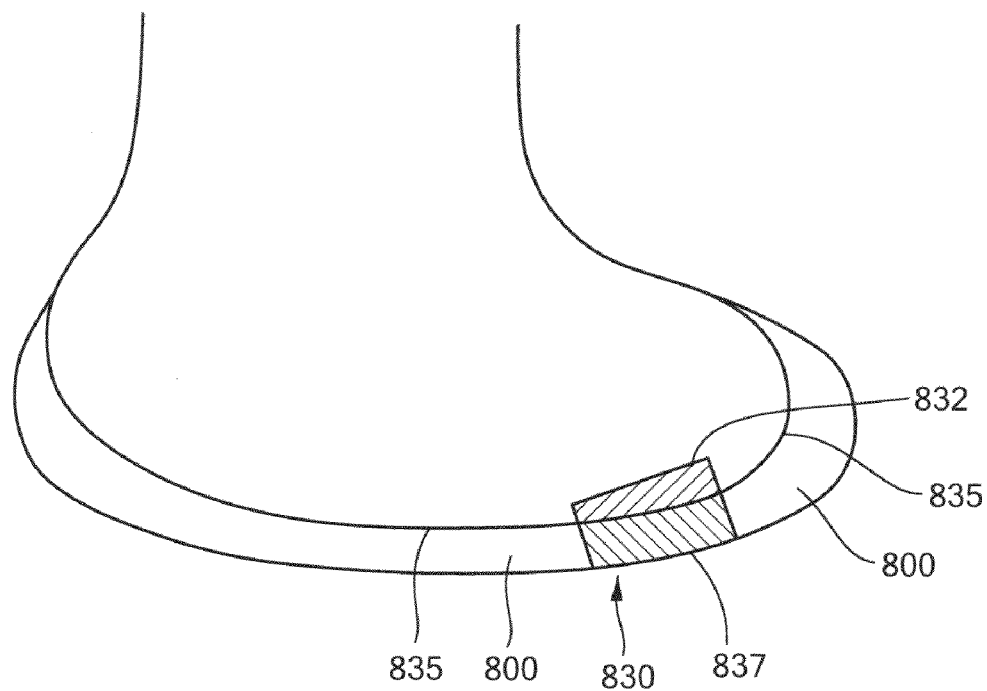
Figure 8G:
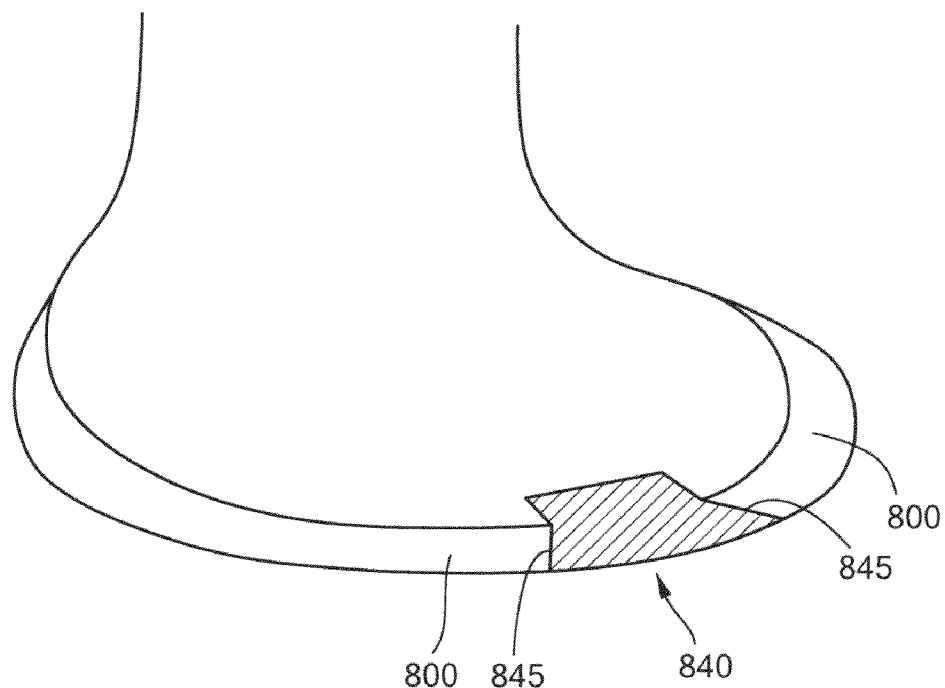
Figure 8H:
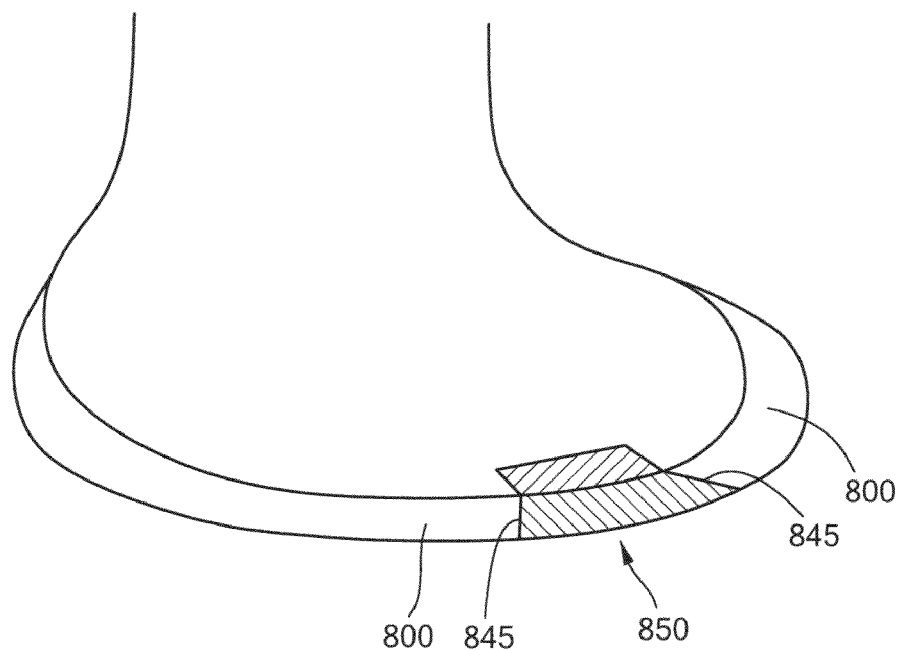
Figure 9A:
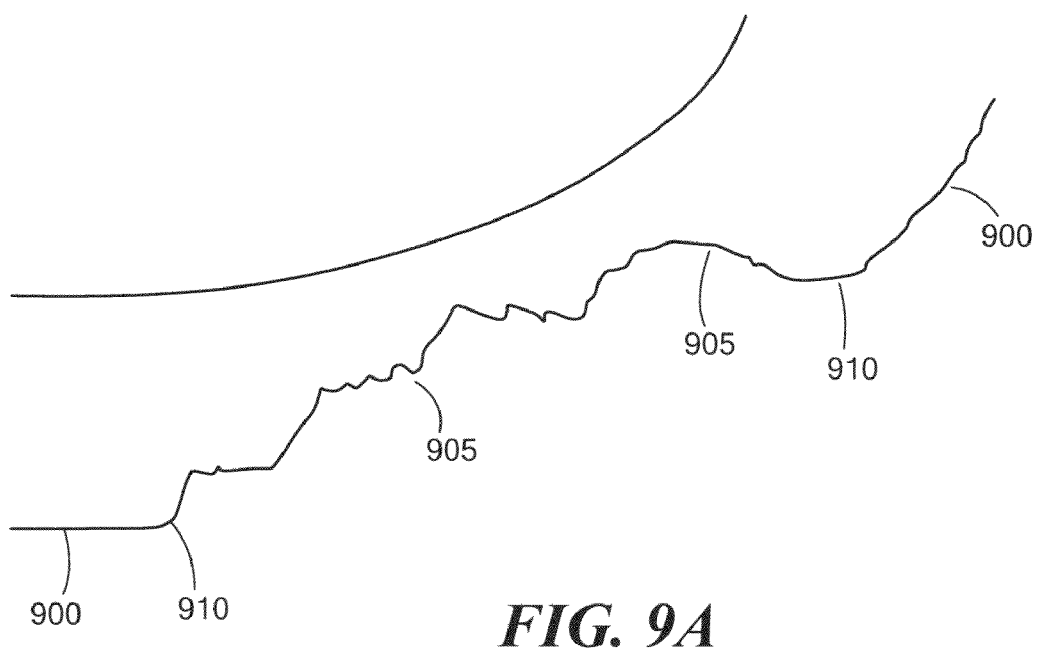
FIG. 9A is a schematic depicting a magnified view of an area of diseased cartilage 905 demonstrating decreased cartilage thickness when compared to the surrounding normal cartilage 900. The margins 910 of the defect have been determined.
Figure 9B:
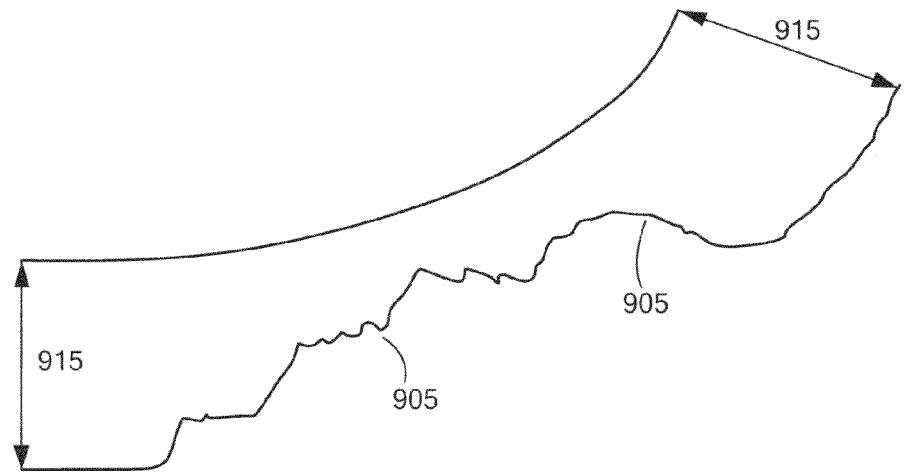
FIG. 9B is a schematic depicting measurement of cartilage thickness 915 adjacent to the defect 905.
Figure 9C:
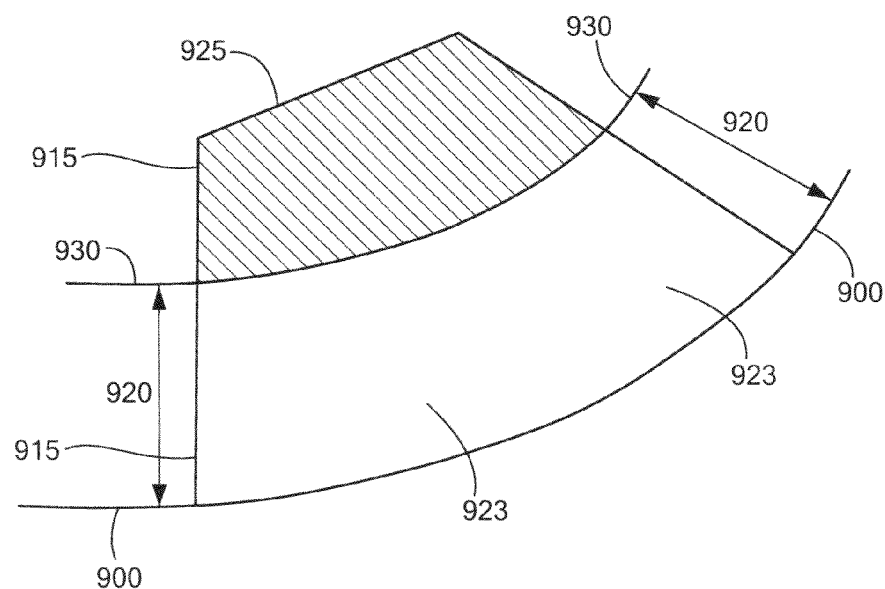
FIG. 9C is a schematic depicting placement of a multi-component mini-prosthesis 915 for articular resurfacing. The thickness 920 of the superficial component 923 closely approximates that of the adjacent normal cartilage 900 and varies in different regions of the prosthesis. The curvature of the distal portion of the deep component 925 is similar to that of the adjacent subchondral bone 930.
Figure 9D:
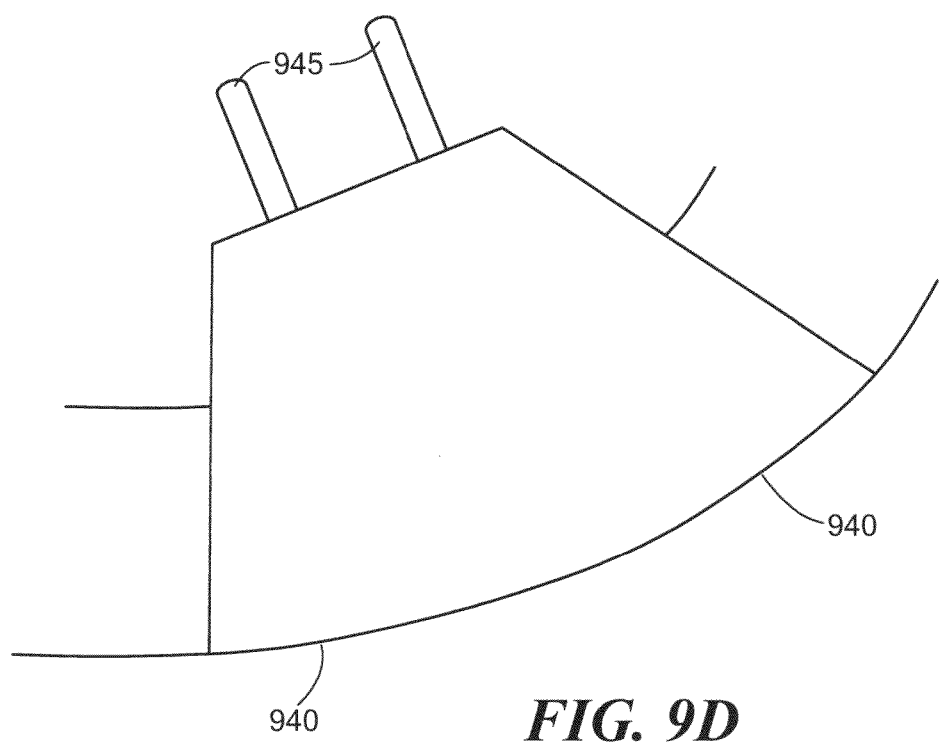
FIG. 9D is a schematic depicting placement of a single component mini-prosthesis 940 utilizing fixturing stems 945.
Figure 9E:
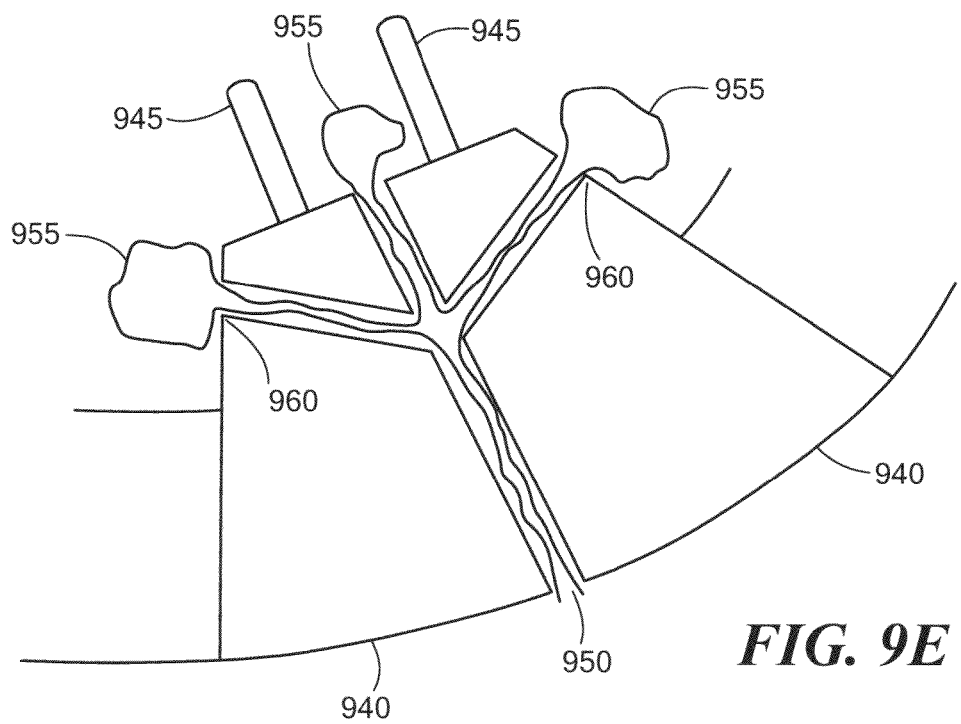
FIG. 9E depicts placement of a single component mini-prosthesis 940 utilizing fixturing stems 945 and an opening 950 for injection of bone cement 955. The mini-prosthesis has an opening at the external surface 950 for injecting bone cement 955 or other liquids. The bone cement 955 can freely extravasate into the adjacent bone and marrow space from several openings at the undersurface of the mini-prosthesis 960 thereby anchoring the mini-prosthesis.

The current invention provides for methods and devices for integration of cartilage replacement or regenerating materials.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher.

All publications, patents and patent applications cited herein, whether above or below, are hereby incorporated by reference in their entirety.

It must be noted that, as used in this specification and the appended claims, the singular forms "a", "an", and "the" include plural references unless the content clearly dictates otherwise. Thus, for example, reference to "an implantation site" includes a one or more such sites.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

The term "arthritis" refers to a group of conditions characterized by progressive deterioration of joints. Thus, the term encompasses a group of different diseases including, but not limited to, osteoarthritis (OA), rheumatoid arthritis, seronegative spondyloarthropathies and posttraumatic joint deformity.

The term "articular" refers to any joint. Thus, "articular cartilage" refers to cartilage in a joint such as a knee, ankle, hip, etc. The term "articular surface" refers to a surface of an articulating bone that is covered by cartilage. For example, in a knee joint several different articular surfaces are present, e.g. in the patella, the medial femoral condyle, the lateral femoral condyle, the medial tibial plateau and the lateral tibial plateau.

The term "weight-bearing surface" refers to the contact area between two opposing articular surfaces during activities of normal daily living, e.g., normal gait. The weight-bearing surface can be determined by any suitable means, for example based on data published in the literature, e.g. anatomic studies. The weight-bearing surface can be determined by superimposing predetermined angles of flexion, extension, translation, tilting and rotation on anatomic models, e.g. of the femur and the tibia. Anatomic models can be generated with use of an imaging test. Biomotion analysis, for example using optoelectronic registration means (see also International Publication WO 02/22014) can also be used to define the weight-bearing surface. Moreover, kinematic imaging tests such as fluoroscopy or MRI of joint motion can be used to estimate the weight-bearing surface for different physical activities. Different modalities for determining the weight-bearing area such as 2D x-ray fluoroscopy and MRI can be merged in order to estimate the weight-bearing area. The weight-bearing area can be determined using any current and future optical, electronic, imaging, or other means of assessing joint motion.

The term "cartilage" or "cartilage tissue" as used herein is generally recognized in the art, and refers to a specialized type of dense connective tissue comprising cells embedded in an extracellular matrix (ECM) (see, for example, Cormack, 1987, Ham's Histology, 9th Ed., J. B. Lippincott Co., pp. 266-272). The biochemical composition of cartilage differs according to type. Several types of cartilage are recognized in the art, including, for example, hyaline cartilage such as that found within the joints, fibrous cartilage such as that found within the meniscus and costal regions, and elastic cartilage. Hyaline cartilage, for example, comprises chondrocytes surrounded by a dense ECM consisting of collagen, proteoglycans and water. Fibrocartilage can form in areas of hyaline cartilage, for example after an injury or, more typically, after certain types of surgery. The production of any type of cartilage is intended to fall within the scope of the invention.

Furthermore, although described primarily in relation to methods for use in humans, the invention may also be practiced so as repair cartilage tissue in any mammal in need thereof, including horses, dogs, cats, sheep, pigs, among others. The treatment of such animals is intended to fall within the scope of the invention.

The terms "articular repair system" and "articular surface repair system" include any system (including, for example, compositions, devices and techniques) to repair, to replace or to regenerate a portion of a joint or an entire joint. The term encompasses systems that repair articular cartilage, articular bone or both bone and cartilage. Articular surface repair systems may also include a meniscal repair system (e.g., meniscal repair system can be composed of a biologic or non-biologic material), for example a meniscal repair system having biomechanical and/or biochemical properties similar to that of healthy menisci. See, for example, U.S. Pat. Publication No. b 2002/0,022,884A1. The meniscal repair system can be surgically or arthroscopically attached to the joint capsule or one or more ligaments. Non-limiting examples of repair systems include metal or plastic implants, polymer implants, combinations thereof, injectable repair materials, for example materials that are self-hardening, autologous chondrocyte transplantation, osteochondral allografting, osteochondral autografting, tibial corticotomy, femoral and/or tibial osteotomy. Repair systems also include treatment with cartilage or bone tissue grown ex vivo as well as in vivo, stem cells, cartilage material grown with use of stem cells, fetal cells or immature or mature cartilage cells, an artificial non-human material, an agent that stimulates repair of diseased cartilage tissue, an agent that stimulates growth of cells, an agent that protects diseased cartilage tissue and that protects adjacent normal cartilage tissue. Articular repair systems include also treatment with a cartilage tissue transplant, a cartilage tissue graft, a cartilage tissue implant, a cartilage tissue scaffold, or any other cartilage tissue replacement or regenerating material. Articular repair systems may include also treatment with a bone tissue transplant, a bone tissue graft, a bone tissue implant, a bone tissue scaffold, or any other bone tissue replacement or regenerating material. Articular repair systems may also include treatment with a meniscus tissue transplant, a meniscus tissue graft, a meniscus tissue implant, a meniscus tissue scaffold, or any other meniscus tissue replacement or regenerating material. Articular repair systems include also surgical tools that facilitate the surgical procedure required for articular repair, for example tools that prepare the area of diseased cartilage tissue and/or subchondral bone for receiving, for example, a cartilage tissue replacement or regenerating material. The term "non-pliable" refers to material that cannot be significantly bent but may retain elasticity.

The terms "replacement material" or "regenerating material" include a broad range of natural and/or synthetic materials including metals, metal alloys, polymers, injectables, combinations thereof used in the methods described herein, for example, cartilage or bone tissue grown ex vivo or in vivo, stem cells, cartilage material grown from stem cells, stem cells, fetal cell, immature or mature cartilage cells, an agent that stimulates growth of cells, an artificial non-human material, a tissue transplant, a tissue graft, a tissue implant, a tissue scaffold, or a tissue regenerating material. The term includes biological materials isolated from various sources (e.g., cells) as well as modified (e.g., genetically modified) materials and/or combinations of isolated and modified materials.

The term "imaging test" includes, but is not limited to, x-ray based techniques (such as conventional film based x-ray films, digital x-ray images, single and dual x-ray absorptiometry, radiographic absorptiometry); fluoroscopic imaging, for example with C-arm devices including C-arm devices with tomographic or cross-sectional imaging capability, digital x-ray tomosynthesis, x-ray imaging including digital x-ray tomosynthesis with use of x-ray contrast agents, for example after intra-articular injection, ultrasound including broadband ultrasound attenuation measurement and speed of sound measurements, A-scan, B-scan and C-scan; computed tomography; nuclear scintigraphy; SPECT; positron emission tomography, optical coherence tomography and MRI. One or more of these imaging tests may be used in the methods described herein, for example in order to obtain certain morphological information about one or several tissues such as bone including bone mineral density and curvature of the subchondral bone, cartilage including biochemical composition of cartilage, cartilage thickness, cartilage volume, cartilage curvature, size of an area of diseased cartilage, severity of cartilage disease or cartilage loss, marrow including marrow composition, synovium including synovial inflammation, lean and fatty tissue, and thickness, dimensions and volume of soft and hard tissues. The imaging test can be performed with use of a contrast agent, such as Gd-DTPA in the case of MRI.

The term "A-scan" refers to an ultrasonic technique where an ultrasonic source transmits an ultrasonic wave into an object, such as patient's body, and the amplitude of the returning echoes (signals) are recorded as a function of time. Only structures that lie along the direction of propagation are interrogated. As echoes return from interfaces within the object or tissue, the transducer crystal produces a voltage that is proportional to the echo intensity. The sequence of signal acquisition and processing of the A-scan data in a modern ultrasonic instrument usually occurs in six major steps:

(1) Detection of the echo (signal) occurs via mechanical deformation of the piezoelectric crystal and is converted to an electric signal having a small voltage.

(2) Preamplification of the electronic signal from the crystal, into a more useful range of voltages is usually necessary to ensure appropriate signal processing.

(3) Time Gain Compensation compensates for the attenuation of the ultrasonic signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultrasonic pulse has been emitted. Thus, reflective boundaries having equal abilities to reflect ultrasonic waves will have equal ultrasonic signals, regardless of the depth of the boundary.

(4) Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

(5) Rectification, demodulation and envelope detection of the high frequency electronic signal permits the sampling and digitization of the echo amplitude free of variations induced by the sinusoidal nature of the waveform.

(6) Rejection level adjustment sets the threshold of signal amplitudes that are permitted to enter a data storage, processing or display system. Rejection of lower signal amplitudes reduces noise levels from scattered ultrasonic signals.

The term "B-scan" refers to an ultrasonic technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a superoinferior or mediolateral direction or a combination of both. The display of multiple adjacent scan lines creates a composite two-dimensional image that portrays the general contour of internal organs.

The term "C-scan" refers to an ultrasonic technique where additional gating electronics are incorporated into a B-scan to eliminate interference from underlying or overlying structures by scanning at a constant-depth. An interface reflects part of the ultrasonic beam energy. All interfaces along the scan line may contribute to the measurement. The gating electronics of the C-mode rejects all returning echoes except those received during a specified time interval. Thus, only scan data obtained from a specific depth range are recorded. Induced signals outside the allowed period are not amplified and, thus, are not processed and displayed. C-mode-like methods are also described herein for A-scan techniques and devices in order to reduce the probe/skin interface reflection.

The term "repair" is used in a broad sense to refer to one or more repairs to damaged joints (e.g., cartilage or bone) or to replacement of one or more components or regions of the joint. Thus, the term encompasses both repair (e.g., one or more portions of a cartilage and/or layers of cartilage or bone) and replacement (e.g., of an entire cartilage).

The term "C-arm" refers to a fluoroscopic x-ray system mounted on a C-shaped arch that allows it to rotate and/or tilt passively or actively around the object to be imaged. The x-ray beam that is transmitted by the x-ray source through the object and received by the detector is displayed on a screen. C-arm typically includes systems that have cross-sectional imaging capability, for example by using rotation of the x-ray tube and detector to reconstruct a cross-sectional image similar to a CT rather than a conventional projectional x-ray only.

The terms "hardening," "solidifying," and "curable" refers to any liquid or sufficiently flowable material that forms a solid or gel, either over time, upon contact with another substance and/or upon application of energy.

General Overview

The present invention provides methods and compositions for repairing joints, particularly for repairing articular cartilage and for facilitating the integration of a wide variety of cartilage repair materials into a subject. Among other things, the techniques described herein allow for the customization of cartilage repair material to suit a particular subject, for example in terms of size, cartilage thickness and/or curvature. When the shape (e.g., size, thickness and/or curvature) of the articular cartilage surface is an exact or near anatomic fit with the non-damaged cartilage or with the subject's original cartilage, the success of repair is enhanced. The repair material may be shaped prior to implantation and such shaping can be based, for example, on electronic images that provide information regarding curvature or thickness of any "normal" cartilage surrounding the defect and/or on curvature of the bone underlying the defect. Thus, the current invention provides, among other things, for minimally invasive methods for partial joint replacement. The methods will require only minimal or, in some instances, no loss in bone stock. Additionally, unlike with current techniques, the methods described herein will help to restore the integrity of the articular surface by achieving an exact or near anatomic match between the implant and the surrounding or adjacent cartilage and/or subchondral bone.

Advantages of the present invention can include, but are not limited to, (i) customization of joint repair, thereby enhancing the efficacy and comfort level for the patient following the repair procedure; (ii) eliminating the need for a surgeon to measure the defect to be repaired intraoperatively in some embodiments; (iii) eliminating the need for a surgeon to shape the material during the implantation procedure; (iv) providing methods of evaluating curvature of the repair material based on bone or tissue images or based on intraoperative probing techniques; (v) providing methods of repairing joints with only minimal or, in some instances, no loss in bone stock; and (vi) improving postoperative joint congruity.

Thus, the methods described herein allow for the design and use of joint repair material that more precisely fits the defect (e.g., site of implantation) and, accordingly, provides improved repair of the joint.

1.0. Assessment of Defects

The methods and compositions described herein may be used to treat defects resulting from disease of the cartilage (e.g., osteoarthritis), bone damage, cartilage damage, trauma, and/or degeneration due to overuse or age. The invention allows, among other things, a health practitioner to evaluate and treat such defects. The size, volume and shape of the area of interest may include only the region of cartilage that has the defect, but preferably will also include contiguous parts of the cartilage surrounding the cartilage defect.

Size, curvature and/or thickness measurements can be obtained using any suitable techniques, for example in one direction, two directions, and/or in three dimensions for example, using suitable mechanical means, laser devices, molds, materials applied to the articular surface that harden and "memorize the surface contour," and/or one or more imaging techniques. Measurements may be obtained non-invasively and/or intraoperatively (e.g., using a probe or other surgical device).

1.1. Imaging Techniques

Non-limiting examples of imaging techniques suitable for measuring thickness and/or curvature (e.g., of cartilage and/or bone) or size of areas of diseased cartilage or cartilage loss include the use of x-rays, magnetic resonance imaging (MRI), computed tomography scanning (CT, also known as computerized axial tomography or CAT), optical coherence tomography, SPECT, PET, ultrasound imaging techniques, and optical imaging techniques. (See, also, International Patent Publication WO 02/22014; U.S. Pat. No. 6,373,250 and Vandeberg et al. (2002) Radiology 222:430-436).

In certain embodiments, CT or MRI is used to assess tissue, bone, cartilage and any defects therein, for example cartilage lesions or areas of diseased cartilage, to obtain information on subchondral bone or cartilage degeneration and to provide morphologic or biochemical or biomechanical information about the area of damage. Specifically, changes such as fissuring, partial or full thickness cartilage loss, and signal changes within residual cartilage can be detected using one or more of these methods. For discussions of the basic NMR principles and techniques, see MRI Basic Principles and Applications, Second Edition, Mark A. Brown and Richard C. Semelka, Wiley-Liss, Inc. (1999). For a discussion of MRI including conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement, (RARE) imaging, gradient echo acquisition in the steady state, (GRASS), and driven equilibrium Fourier transform (DEFT) imaging, to obtain information on cartilage, see WO 02/22014. Thus, in preferred embodiments, the measurements are three-dimensional images obtained as described in WO 02/22014. Three-dimensional internal images, or maps, of the cartilage alone or in combination with a movement pattern of the joint can be obtained. Three-dimensional internal images can include information on biochemical composition of the articular cartilage. In addition, imaging techniques can be compared over time, for example to provide up to date information on the shape and type of repair material needed.

Any of the imaging devices described herein may also be used intra-operatively (see, also below), for example using a hand-held ultrasound and/or optical probe to image the articular surface intra-operatively.

1.2. Intra-Operative Measurements

Alternatively, or in addition to, non-invasive imaging techniques, measurements of the size of an area of diseased cartilage or an area of cartilage loss, measurements of cartilage thickness and/or curvature of cartilage or bone can be obtained intraoperatively during arthroscopy or open arthrotomy. Intraoperative measurements may or may not involve actual contact with one or more areas of the articular surfaces.

Devices to obtain intraoperative measurements of cartilage, and to generate a topographical map of the surface include but are not limited to, Placido disks and laser interferometers, and/or deformable materials. (See, for example, U.S. Pat. Nos. 6,382,028; 6,057,927; 5,523,843; 5,847,804; and 5,684,562). For example, a Placido disk (a concentric array that projects well-defined circles of light of varying radii, generated either with laser or white light transported via optical fiber) can be attached to the end of an endoscopic device (or to any probe, for example a hand-held probe) so that the circles of light are projected onto the cartilage surface. One or more imaging cameras can be used (e.g., attached to the device) to capture the reflection of the circles. Mathematical analysis is used to determine the surface curvature. The curvature can then be visualized on a monitor as a color-coded, topographical map of the cartilage surface. Additionally, a mathematical model of the topographical map can be used to determine the ideal surface topography to replace any cartilage defects in the area analyzed. This computed, ideal surface can then also be visualized on the monitor, and is used to select the curvature of the replacement material or regenerating material.

Similarly a laser interferometer can also be attached to the end of an endoscopic device. In addition, a small sensor may be attached to the device in order to determine the cartilage surface curvature using phase shift interferometry, producing a fringe pattern analysis phase map (wave front) visualization of the cartilage surface. The curvature can then be visualized on a monitor as a color coded, topographical map of the cartilage surface. Additionally, a mathematical model of the topographical map can be used to determine the ideal surface topography to replace any cartilage defects in the area analyzed. This computed, ideal surface can then also be visualized on the monitor, and can be used to select the curvature of the replacement cartilage.

One skilled in the art will readily recognize other techniques for optical measurements of the cartilage surface curvature.

Mechanical devices (e.g., probes) may also be used for intraoperative measurements, for example, deformable materials such as gels, molds, any hardening materials (e.g., materials that remain deformable until they are heated, cooled, or otherwise manipulated). See, e.g., WO 02/34310. For example, a deformable gel can be applied to a femoral condyle. The side of the gel pointing towards the condyle will yield a negative impression of the surface contour of the condyle. Said negative impression can be used to determine the size of a defect, the depth of a defect and the curvature of the articular surface in and adjacent to a defect. This information can be used to select a therapy, e.g. an articular surface repair system. In another example, a hardening material can be applied to an articular surface, e.g. a femoral condyle or a tibial plateau. Said hardening material will remain on the articular surface until hardening has occurred. The hardening material will then be removed from the articular surface. The side of the hardening material pointing towards the articular surface will yield a negative impression of the articular surface. The negative impression can be used to determine the size of a defect, the depth of a defect and the curvature of the articular surface in and adjacent to a defect. This information can be used to select a therapy, e.g. an articular surface repair system.

In certain embodiments, the deformable material comprises a plurality of individually moveable mechanical elements. When pressed against the surface of interest, each element may be pushed in the opposing direction and the extent to which it is pushed (deformed) will correspond to the curvature of the surface of interest. The device may include a brake mechanism so that the elements are maintained in the position that mirrors the surface of the cartilage and/or bone. The device can then be removed from the patient and analyzed for curvature. Alternatively, each individual moveable element may include markers indicating the amount and/or degree they are deformed at a given spot. A camera can be used to intra-operatively image the device and the image can be saved and analyzed for curvature information. Suitable markers include, but are not limited to, actual linear measurements (metric or imperial), different colors corresponding to different amounts of deformation and/or different shades or hues of the same color(s).

Other devices to measure cartilage and subchondral bone intraoperatively include, for example, ultrasound probes. An ultrasound probe, preferably handheld, can be applied to the cartilage and the curvature of the cartilage and/or the subchondral bone can be measured. Moreover, the size of a cartilage defect can be assessed and the thickness of the articular cartilage can be determined. Such ultrasound measurements can be obtained in A-mode, B-mode, or C-mode. If A-mode measurements are obtained, an operator will typically repeat the measurements with several different probe orientations, e.g. mediolateral and anteroposterior, in order to derive a three-dimensional assessment of size, curvature and thickness.

One skilled in the art will easily recognize that different probe designs are possible using said optical, laser interferometry, mechanical and ultrasound probes. The probes are preferably handheld. In certain embodiments, the probes or at least a portion of the probe, typically the portion that is in contact with the tissue, will be sterile. Sterility can be achieved with use of sterile covers, for example similar to those disclosed in WO9908598A1.

Analysis on the curvature of the articular cartilage or subchondral bone using imaging tests and/or intraoperative measurements can be used to determine the size of an area of diseased cartilage or cartilage loss. For example, the curvature can change abruptly in areas of cartilage loss. Such abrupt or sudden changes in curvature can be used to detect the boundaries of diseased cartilage or cartilage defects.

1.3. Models

Using information on thickness and curvature of the cartilage, a physical model of the surfaces of the articular cartilage and of the underlying bone can be created. This physical model can be representative of a limited area within the joint or it can encompass the entire joint. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint. The location of a diseased area of cartilage can be determined, for example using a 3D coordinate system or a 3D Euclidian distance as described in WO 02/22014.

In this way, the size of the defect to be repaired can be determined. As will be apparent, some, but not all, defects will include less than the entire cartilage. Thus, in one embodiment of the invention, the thickness of the normal or only mildly diseased cartilage surrounding one or more cartilage defects is measured. This thickness measurement can be obtained at a single point or, preferably, at multiple points, for example 2 point, 4-6 points, 7-10 points, more than 10 points or over the length of the entire remaining cartilage. Furthermore, once the size of the defect is determined, an appropriate therapy (e.g., articular repair system) can be selected such that as much as possible of the healthy, surrounding tissue is preserved.

In other embodiments, the curvature of the articular surface can be measured to design and/or shape the repair material. Further, both the thickness of the remaining cartilage and the curvature of the articular surface can be measured to design and/or shape the repair material. Alternatively, the curvature of the subchondral bone can be measured and the resultant measurement(s) can be used to either select or shape a cartilage replacement material.

2.0. Repair Materials

A wide variety of materials find use in the practice of the present invention, including, but not limited to, plastics, metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and the articular surface and/or the subchondral bone, a repair material can be formed or selected. Further, using one or more of these techniques described herein, a cartilage replacement or regenerating material having a curvature that will fit into a particular cartilage defect, will follow the contour and shape of the articular surface, and will match the thickness of the surrounding cartilage. The repair material may include any combination of materials, and preferably includes at least one non-pliable (hard) material.

2.1. Metal and Polymeric Repair Materials

Currently, joint repair systems often employ metal and/or polymeric materials including, for example, prosthesis which are anchored into the underlying bone (e.g., a femur in the case of a knee prosthesis). See, e.g., U.S. Pat. Nos. 6,203,576 and 6,322,588 and references cited therein. A wide-variety of metals may find use in the practice of the present invention, and may be selected based on any criteria, for example, based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl-)methacrylamide], poly(hydroxy acids), poly(epsilon-caprolactone), polylactic acid, polyglycolic acid, poly(dimethyl glycolic acid), poly (hydroxy butyrate), and similar copolymers may also be used.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating.

More than one metal and/or polymer may be used in combination with each other. For example, one or more metal-containing substrates may be coated with polymers in one or more regions or, alternatively, one or more polymer-containing substrate may be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof) or combinations thereof. See, e.g., Hahn U.S. Pat. No. 3,605,123. Tronzo U.S. Pat. No. 3,808,606 and Tronzo U.S. Pat. No. 3,843,975; Smith U.S. Pat. No. 3,314,420; Scharbach U.S. Pat. No. 3,987,499; and German Offenlegungsschrift 2,306,552. There may be more than one coating layer and the layers may have the same or different porosities. See, e.g., U.S. Pat. No. 3,938,198.

The coating may be applied by surrounding a core with powdered polymer and heating until cured to form a coating with an internal network of interconnected pores. The tortuosity of the pores (e.g., a measure of length to diameter of the paths through the pores) may be important in evaluating the probable success of such a coating in use on a prosthetic device. See, also, Morris U.S. Pat. No. 4,213,816. The porous coating may be applied in the form of a powder and the article as a whole subjected to an elevated temperature that bonds the powder to the substrate. Selection of suitable polymers and/or powder coatings may be determined in view of the teachings and references cited herein, for example based on the melt index of each.

2.2. Biological Repair Materials

Repair materials may also include one or more biological material either alone or in combination with non-biological materials. For example, any base material can be designed or shaped and suitable cartilage replacement or regenerating material(s) such as fetal cartilage cells can be applied to be the base. The cells can be then be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. Nos. 5,478,739; 5,842,477; 6,283,980 and 6,365,405. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers may be bioresorbable.

Biological materials used in the methods described herein can be autografts (from the same subject); allografts (from another individual of the same species) and/or xenografts (from another species). See, also, International Patent Publications WO 02/22014 and WO 97/27885. In certain embodiments autologous materials are preferred, as they may carry a reduced risk of immunological complications to the host, including re-absorption of the materials, inflammation and/or scarring of the tissues surrounding the implant site.

In one embodiment of the invention, a probe is used to harvest tissue from a donor site and to prepare a recipient site. The donor site can be located in a xenograft, an allograft or an autograft. The probe is used to achieve a good anatomic match between the donor tissue sample and the recipient site. The probe is specifically designed to achieve a seamless or near seamless match between the donor tissue sample and the recipient site. The probe can, for example, be cylindrical. The distal end of the probe is typically sharp in order to facilitate tissue penetration. Additionally, the distal end of the probe is typically hollow in order to accept the tissue. The probe can have an edge at a defined distance from its distal end, e.g. at 1 cm distance from the distal end and the edge can be used to achieve a defined depth of tissue penetration for harvesting. The edge can be external or can be inside the hollow portion of the probe. For example, an orthopedic surgeon can take the probe and advance it with physical pressure into the cartilage, the subchondral bone and the underlying marrow in the case of a joint such as a knee joint. The surgeon can advance the probe until the external or internal edge reaches the cartilage surface. At that point, the edge will prevent further tissue penetration thereby achieving a constant and reproducible tissue penetration. The distal end of the probe can include a blade or saw-like structure or tissue cutting mechanism. For example, the distal end of the probe can include an iris-like mechanism consisting of several small blades. The at least one or more blades can be moved using a manual, motorized or electrical mechanism thereby cutting through the tissue and separating the tissue sample from the underlying tissue. Typically, this will be repeated in the donor and the recipient. In the case of an iris-shaped blade mechanism, the individual blades can be moved so as to close the iris thereby separating the tissue sample from the donor site.

In another embodiment of the invention, a laser device or a radiofrequency device can be integrated inside the distal end of the probe. The laser device or the radiofrequency device can be used to cut through the tissue and to separate the tissue sample from the underlying tissue.

In one embodiment of the invention, the same probe can be used in the donor and in the recipient. In another embodiment, similarly shaped probes of slightly different physical dimensions can be used. For example, the probe used in the recipient can be slightly smaller than that used in the donor thereby achieving a tight fit between the tissue sample or tissue transplant and the recipient site. The probe used in the recipient can also be slightly shorter than that used in the donor thereby correcting for any tissue lost during the separation or cutting of the tissue sample from the underlying tissue in the donor material.

Any biological repair material may be sterilized to inactivate biological contaminants such as bacteria, viruses, yeasts, molds, mycoplasmas and parasites. Sterilization may be performed using any suitable technique, for example radiation, such as gamma radiation.

Any of the biological material described herein may be harvested with use of a robotic device. The robotic device can use information from an electronic image for tissue harvesting.

In certain embodiments, the cartilage replacement material has a particular biochemical composition. For instance, the biochemical composition of the cartilage surrounding a defect can be assessed by taking tissue samples and chemical analysis or by imaging techniques. For example, WO 02/22014 describes the use of gadolinium for imaging of articular cartilage to monitor glycosaminoglycan content within the cartilage. The cartilage replacement or regenerating material can then be made or cultured in a manner, to achieve a biochemical composition similar to that of the cartilage surrounding the implantation site. The culture conditions used to achieve the desired biochemical compositions can include, for example, varying concentrations biochemical composition of said cartilage replacement or regenerating material can, for example, be influenced by controlling concentrations and exposure times of certain nutrients and growth factors.

2.3. Multiple-Component Repair Materials

Figure 12A:
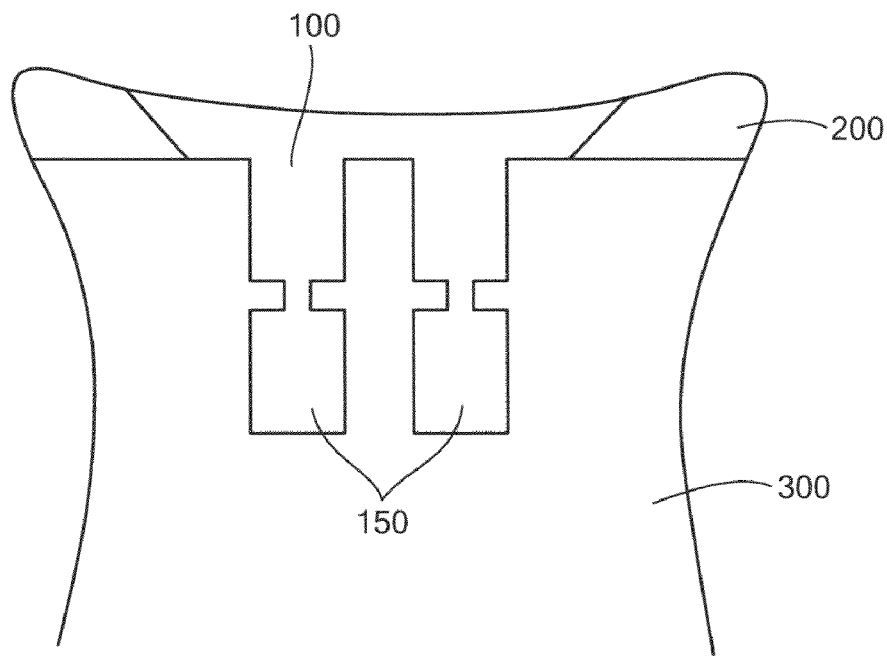
FIGS. 12A and B show exemplary articular repair systems 100 having an outer contour matching the surrounding normal cartilage 200. The systems are implanted into the underlying bone 300 using one or more pegs 150, 175. The pegs may be porous-coated and may have flanges 125 as shown in FIG. 12B.
Figure 12B:
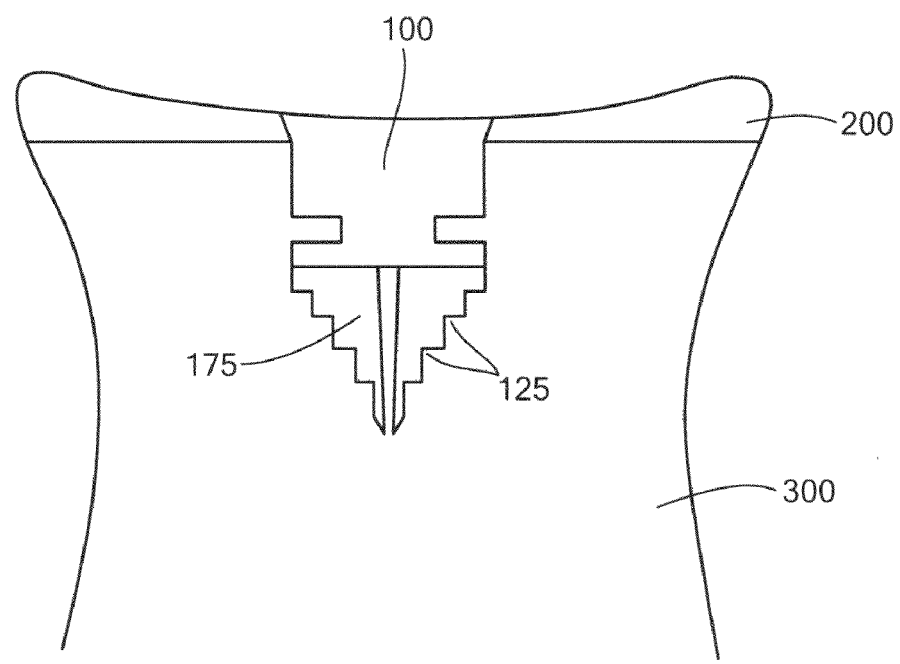

The articular repair system may include one or more components. Non-limiting examples of one-component systems include a plastic, a polymer, a metal, a metal alloy, a biologic material or combinations thereof. In certain embodiments, the surface of the repair system facing the underlying bone is smooth. In other embodiments, the surface of the repair system facing the underlying bone is porous or porous-coated. In another aspect, the surface of the repair system facing the underlying bone is designed with one or more grooves, for example to facilitate the in-growth of the surrounding tissue. The external surface of the device can have a step-like design, which can be advantageous for altering biomechanical stresses. Optionally, flanges can also be added at one or more positions on the device (e.g., to prevent the repair system from rotating, to control toggle and/or prevent settling into the marrow cavity). The flanges can be part of a conical or a cylindrical design. A portion or all of the repair system facing the underlying bone can also be flat which may help to control depth of the implant and to prevent toggle. (See, also FIGS. 12, 13 and 14).

Non-limiting examples of multiple-component systems include combinations of metal, plastic, metal alloys and one or more biological materials. One or more components of the articular surface repair system can be composed of a biologic material (e.g. a tissue scaffold with cells such as cartilage cells or stem cells alone or seeded within a substrate such as a bioresorable material or a tissue scaffold, allograft, autograft or combinations thereof) and/or a non-biological material (e.g., polyethylene or a chromium alloy such as chromium cobalt).

Thus, the repair system can include one or more areas of a single material or a combination of materials, for example, the articular surface repair system can have a superficial and a deep component. The superficial component is typically designed to have size, thickness and curvature similar to that of the cartilage tissue lost while the deep component is typically designed to have a curvature similar to the subchondral bone. In addition, the superficial component can have biomechanical properties similar to articular cartilage, including but not limited to similar elasticity and resistance to axial loading or shear forces. The superficial and the deep component can consist of two different metals or metal alloys. One or more components of the system (e.g., the deep portion) can be composed of a biologic material including, but not limited to bone, or a non-biologic material including, but not limited to hydroxyapatite, tantalum, a chromium alloy, chromium cobalt or other metal alloys.

One or more regions of the articular surface repair system (e.g., the outer margin of the superficial portion and/or the deep portion) can be bioresorbable, for example to allow the interface between the articular surface repair system and the patient's normal cartilage, over time, to be filled in with hyaline or fibrocartilage. Similarly, one or more regions (e.g., the outer margin of the superficial portion of the articular surface repair system and/or the deep portion) can be porous. The degree of porosity can change throughout the porous region, linearly or non-linearly, for where the degree of porosity will typically decrease towards the center of the articular surface repair system. The pores can be designed for in-growth of cartilage cells, cartilage matrix, and connective tissue thereby achieving a smooth interface between the articular surface repair system and the surrounding cartilage.

The repair system (e.g., the deep component in multiple component systems) can be attached to the patient's bone with use of a cement-like material such as methylmethacrylate, injectable hydroxy- or calcium-apatite materials and the like.

In certain embodiments, one or more portions of the articular surface repair system can be pliable or liquid or deformable at the time of implantation and can harden later. Hardening can occur within 1 second to 2 hours (or any time period therebetween), preferably with in 1 second to 30 minutes (or any time period therebetween), more preferably between 1 second and 10 minutes (or any time period therebetween).

One or more components of the articular surface repair system can be adapted to receive injections. For example, the external surface of the articular surface repair system can have one or more openings therein. The openings can be sized so as to receive screws, tubing, needles or other devices which can be inserted and advanced to the desired depth, for example through the articular surface repair system into the marrow space. Injectables such as methylmethacrylate and injectable hydroxy- or calcium-apatite materials can then be introduced through the opening (or tubing inserted therethrough) into the marrow space thereby bonding the articular surface repair system with the marrow space. Similarly, screws or pins can be inserted into the openings and advanced to the underlying subchondral bone and the bone marrow or epiphysis to achieve fixation of the articular surface repair system to the bone. Portions or all components of the screw or pin can be bioresorbable, for example, the distal portion of a screw that protrudes into the marrow space can be bioresorbable. During the initial period after the surgery, the screw can provide the primary fixation of the articular surface repair system. Subsequently, ingrowth of bone into a porous coated area along the undersurface of the articular cartilage repair system can take over as the primary stabilizer of the articular surface repair system against the bone.

The articular surface repair system can be anchored to the patient's bone with use of a pin or screw or other attachment mechanism. The attachment mechanism can be bioresorbable. The screw or pin or attachment mechanism can be inserted and advanced towards the articular surface repair system from a non-cartilage covered portion of the bone or from a non-weight-bearing surface of the joint.

The interface between the articular surface repair system and the surrounding normal cartilage can be at an angle, for example oriented at an angle of 90 degrees relative to the underlying subchondral bone. Suitable angles can be determined in view of the teachings herein, and in certain cases, non-90 degree angles may have advantages with regard to load distribution along the interface between the articular surface repair system and the surrounding normal cartilage.

The interface between the articular surface repair system and the surrounding normal cartilage and/or bone may be covered with a pharmaceutical or bioactive agent, for example a material that stimulates the biological integration of the repair system into the normal cartilage and/or bone. The surface area of the interface can be irregular, for example, to increase exposure of the interface to pharmaceutical or bioactive agents.

2.4. Customized Containers

In another embodiment of the invention, a container or well can be formed to the selected specifications, for example to match the material needed for a particular subject or to create a stock of repair materials in a variety of sizes. The size and shape of the container may be designed using the thickness and curvature information obtained from the joint and from the cartilage defect. More specifically, the inside of the container can be shaped to follow any selected measurements, for example as obtained from the cartilage defect(s) of a particular subject. The container can be filled with a cartilage replacement or regenerating material, for example, collagen-containing materials, plastics, bioresorbable materials and/or any suitable tissue scaffold. The cartilage regenerating or replacement material can also consist of a suspension of stem cells or fetal or immature or mature cartilage cells that subsequently develop to more mature cartilage inside the container. Further, development and/or differentiation can be enhanced with use of certain tissue nutrients and growth factors.

The material is allowed to harden and/or grow inside the container until the material has the desired traits, for example, thickness, elasticity, hardness, biochemical composition, etc. Molds can be generated using any suitable technique, for example computer devices and automation, e.g. computer assisted design (CAD) and, for example, computer assisted modeling (CAM). Because the resulting material generally follows the contour of the inside of the container it will better fit the defect itself and facilitate integration.

2.5. Shaping

In certain instances shaping of the repair material will be required before or after formation (e.g., growth to desired thickness), for example where the thickness of the required cartilage material is not uniform (e.g., where different sections of the cartilage replacement or regenerating material require different thicknesses).

The replacement material can be shaped by any suitable technique including, but not limited to, mechanical abrasion, laser abrasion or ablation, radiofrequency treatment, cryoablation, variations in exposure time and concentration of nutrients, enzymes or growth factors and any other means suitable for influencing or changing cartilage thickness. See, e.g., WO 00/15153; If enzymatic digestion is used, certain sections of the cartilage replacement or regenerating material can be exposed to higher doses of the enzyme or can be exposed longer as a means of achieving different thicknesses and curvatures of the cartilage replacement or regenerating material in different sections of said material.

The material can be shaped manually and/or automatically, for example using a device into which a pre-selected thickness and/or curvature has been inputted and programming the device to achieve the desired shape.

In addition to, or instead of, shaping the cartilage repair material, the site of implantation (e.g., bone surface, any cartilage material remaining, etc.) can also be shaped by any suitable technique in order to enhanced integration of the repair material.

2.6. Pre-Existing Repair Systems

As described herein, repair systems of various sizes, curvatures and thicknesses can be obtained. These repair systems can be catalogued and stored to create a library of systems from which an appropriate system can then be selected. In other words, a defect is assessed in a particular subject and a pre-existing repair system having the closest shape and size is selected from the library for further manipulation (e.g., shaping) and implantation.

2.7. Mini-Prosthesis

As noted above, the methods and compositions described herein can be used to replace only a portion of the articular surface, for example, an area of diseased cartilage or lost cartilage on the articular surface. In these systems, the articular surface repair system may be designed to replace only the area of diseased or lost cartilage or it can extend beyond the area of diseased or lost cartilage, e.g., 3 or 5 mm into normal adjacent cartilage. In certain embodiments, the prosthesis replaces less than about 70% to 80% (or any value therebetween) of the articular surface (e.g., any given articular surface such as a single femoral condyle, etc.), preferably, less than about 50% to 70% (or any value therebetween), more preferably, less than about 30% to 50% (or any value therebetween), more preferably less than about 20% to 30% (or any value therebetween), even more preferably less than about 20% of the articular surface.

As noted above, the prosthesis may include multiple components, for example a component that is implanted into the bone (e.g., a metallic device) attached to a component that is shaped to cover the defect of the cartilage overlaying the bone. Additional components, for example intermediate plates, meniscus repairs systems and the like may also be included. It is contemplated that each component replaces less than all of the corresponding articular surface. However, each component need not replace the same portion of the articular surface. In other words, the prosthesis may have a bone-implanted component that replaces less than 30% of the bone and a cartilage component that replaces 60% of the cartilage. The prosthesis may include any combination, so long as each component replaces less than the entire articular surface.

The articular surface repair system may be formed or selected so that it will achieve a near anatomic fit or match with the surrounding or adjacent cartilage. Typically, the articular surface repair system is formed and/or selected so that its outer margin located at the external surface will be aligned with the surrounding or adjacent cartilage.

Thus, the articular repair system can be designed to replace the weight-bearing portion (or more or less than the weight bearing portion) of an articular surface, for example in a femoral condyle. The weight-bearing surface refers to the contact area between two opposing articular surfaces during activities of normal daily living (e.g., normal gait). At least one or more weight-bearing portions can be replaced in this manner, e.g., on a femoral condyle and on a tibia.

In other embodiments, an area of diseased cartilage or cartilage loss can be identified in a weight-bearing area and only a portion of said weight-bearing area, specifically the portion containing said diseased cartilage or area of cartilage loss, can be replaced with an articular surface repair system.

In another embodiment, for example in patients with diffuse cartilage loss, the articular repair system can be designed to replace an area slightly larger than the weight-bearing surface.

In certain aspects, the defect to be repaired is located only on one articular surface, typically the most diseased surface. For example, in a patient with severe cartilage loss in the medial femoral condyle but less severe disease in the tibia, the articular surface repair system can only be applied to the medial femoral condyle. Preferably, in any methods described herein, the articular surface repair system is designed to achieve an exact or a near anatomic fit with the adjacent normal cartilage.

In other embodiments, more than one articular surface can be repaired.

The area(s) of repair will be typically limited to areas of diseased cartilage or cartilage loss or areas slightly greater than the area of diseased cartilage or cartilage loss within the weight-bearing surface(s).

The implant and/or the implant site can be sculpted to achieve a near anatomic alignment between the implant and the implant site. In another embodiment of the invention, an electronic image is used to measure the thickness, curvature, or shape of the articular cartilage or the subchondral bone, and/or the size of a defect, and an articular surface repair system is selected using this information. The articular surface repair system can be inserted arthroscopically. The articular surface repair system can have a single radius. More typically, however, the articular surface repair system 1100 can have varying curvatures and radii within the same plane, e.g. anteroposterior or mediolateral or superoinferior or oblique planes, or within multiple planes. In this manner, the articular surface repair system can be shaped to achieve a near anatomic alignment between the implant and the implant site. This design allows not only allows for different degrees of convexity or concavity, but also for concave portions within a predominantly convex shape or vice versa 1100.

If a multiple component repair material has been selected, for example with a superficial component 1105 consisting of a polymeric material and a deep component 1110 consisting of a metal alloy, the superficial component can be designed so that its thickness and curvature will closely match that of the surrounding cartilage 1115. Thus, the superficial component can have more than one thickness in different portions of the articular repair system. Moreover, the superficial component can have varying curvatures and radii within the same plane, e.g. anteroposterior or mediolateral or superoinferior or oblique planes, or within multiple planes. Similarly, the deep component can have varying curvatures and radii within the same plane, e.g. anteroposterior or mediolateral or superoinferior or oblique planes, or within multiple planes. Typically, the curvature of the deep component will be designed to follow that of the subchondral bone.

In another embodiment the articular surface repair system has a fixturing stem, for example, as described in the Background of U.S. Pat. No. 6,224,632. The fixturing stem can have different shapes including conical, rectangular, fin among others. The mating bone cavity is typically similarly shaped as the corresponding stem.

As shown in FIG. 12, the articular surface repair system 100 can be affixed to the subchondral bone 300, with one or more fixturing stems (pegs) 150 extending through the subchondral plate into the marrow space. In certain instances, this design may reduce the likelihood that the implant will settle deeper into the joint over time by resting portions of the implant against the subchondral bone. The fixturing stems or pegs can be of any shape, for example, cylindrical or conical. Optionally, the fixturing stems or pegs can have notches or openings to allow bone ingrowth. In addition, the fixturing stems or pegs can be porous coated for bone ingrowth. The fixturing stems or pegs can be affixed to the bone using bone cement. An anchoring device can be affixed to the fixturing stem or peg. The anchoring device can have an umbrella shape (e.g., radially expanding elements) with the wider portion pointing towards the subchondral bone and away from the peg. The anchoring device can be advantageous for providing immediate fixation of the implant. The undersurface of the articular repair system facing the subchondral bone can be textured or rough thereby increasing the contact surface between the articular repair system and the subchondral bone. Alternatively, the undersurface of the articular repair system can be porous coated thereby allowing ingrowth. The surgeon can support the ingrowth of bone by treating the subchondral bone with a rasp, typically to create a larger surface area and/or until bleeding from the subchondral bone occurs.

In another embodiment, the articular surface repair system can be attached to the underlying bone or bone marrow using bone cement. Bone cement is typically made from an acrylic polymeric material. Typically, the bone cement is comprised of two components: a dry power component and a liquid component, which are subsequently mixed together. The dry component generally includes an acrylic polymer, such as polymethylmethacrylate (PMMA). The dry component can also contain a polymerization initiator such as benzoylperoxide, which initiates the free-radical polymerization process that occurs when the bone cement is formed. The liquid component, on the other hand, generally contains a liquid monomer such as methyl methacrylate (MMA). The liquid component can also contain an accelerator such as an amine (e.g., N,N-dimethyl-p-toluidine). A stabilizer, such as hydroquinone, can also be added to the liquid component to prevent premature polymerization of the liquid monomer. When the liquid component is mixed with the dry component, the dry component begins to dissolve or swell in the liquid monomer. The amine accelerator reacts with the initiator to form free radicals that begin to link monomer units to form polymer chains. In the next two to four minutes, the polymerization process proceeds changing the viscosity of the mixture from a syrup-like consistency (low viscosity) into a dough-like consistency (high viscosity). Ultimately, further polymerization and curing occur, causing the cement to harden and affix a prosthesis to a bone.

In certain aspects of the invention, bone cement 955 or another liquid attachment material such as injectable calciumhydroxyapatite can be injected into the marrow cavity through one or more openings 950 in the prosthesis. These openings in the prosthesis can extend from the articular surface to the undersurface of the prosthesis 960. After injection, the openings can be closed with a polymer, silicon, metal, metal alloy or bioresorbable plug.

In another embodiment, one or more components of the articular surface repair (e.g., the surface of the system that is pointing towards the underlying bone or bone marrow) can be porous or porous coated. A variety of different porous metal coatings have been proposed for enhancing fixation of a metallic prosthesis by bone tissue ingrowth. Thus, for example, U.S. Pat. No. 3,855,638 discloses a surgical prosthetic device, which may be used as a bone prosthesis, comprising a composite structure consisting of a solid metallic material substrate and a porous coating of the same solid metallic material adhered to and extending over at least a portion of the surface of the substrate. The porous coating consists of a plurality of small discrete particles of metallic material bonded together at their points of contact with each other to define a plurality of connected interstitial pores in the coating. The size and spacing of the particles, which can be distributed in a plurality of monolayers, can be such that the average interstitial pore size is not more than about 200 microns. Additionally, the pore size distribution can be substantially uniform from the substrate-coating interface to the surface of the coating. In another embodiment, the articular surface repair system can contain one or more polymeric materials that can be loaded with and release therapeutic agents including drugs or other pharmacological treatments that can be used for drug delivery. The polymeric materials can, for example, be placed inside areas of porous coating. The polymeric materials can be used to release therapeutic drugs, e.g. bone or cartilage growth stimulating drugs. This embodiment can be combined with other embodiments, wherein portions of the articular surface repair system can be bioresorbable. For example, the superficial layer of an articular surface repair system or portions of its superficial layer can be bioresorbable. As the superficial layer gets increasingly resorbed, local release of a cartilage growth-stimulating drug can facilitate ingrowth of cartilage cells and matrix formation.

In any of the methods or compositions described herein, the articular surface repair system can be pre-manufactured with a range of sizes, curvatures and thicknesses. Alternatively, the articular surface repair system can be custom-made for an individual patient.

2.8 Sizing

The articular repair system may be formed or selected so that it will achieve a near anatomic fit or match with the surrounding or adjacent cartilage or subchondral bone or menisci and other tissue. The shape of the repair system can be based on the analysis of an electronic image (e.g. MRI, CT, digital tomosynthesis, optical coherence tomography or the like). If the articular repair system is intended to replace an area of diseased cartilage or lost cartilage, the near anatomic fit can be achieved using a method that provides a virtual reconstruction of the shape of healthy cartilage in an electronic image.

In one embodiment of the invention, a near normal cartilage surface at the position of the cartilage defect may be reconstructed by interpolating the healthy cartilage surface across the cartilage defect or area of diseased cartilage. This can, for example, be achieved by describing the healthy cartilage by means of a parametric surface (e.g. a B-spline surface), for which the control points are placed such that the parametric surface follows the contour of the healthy cartilage and bridges the cartilage defect or area of diseased cartilage. The continuity properties of the parametric surface will provide a smooth integration of the part that bridges the cartilage defect or area of diseased cartilage with the contour of the surrounding healthy cartilage. The part of the parametric surface over the area of the cartilage defect or area of diseased cartilage can be used to determine the shape or part or the shape of the articular repair system to match with the surrounding cartilage.

In another embodiment, a near normal cartilage surface at the position of the cartilage defect or area of diseased cartilage may be reconstructed using morphological image processing. In a first step, the cartilage can be extracted from the electronic image using manual, semi-automated and/or automated segmentation techniques (e.g., manual tracing, region growing, live wire, model-based segmentation), resulting in a binary image. Defects in the cartilage appear as indentations that may be filled with a morphological closing operation performed in 2-D or 3-D with an appropriately selected structuring element. The closing operation is typically defined as a dilation followed by an erosion. A dilation operator sets the current pixel in the output image to 1 if at least one pixel of the structuring element lies inside a region in the source image. An erosion operator sets the current pixel in the output image to 1 if the whole structuring element lies inside a region in the source image. The filling of the cartilage defect or area of diseased cartilage creates a new surface over the area of the cartilage defect or area of diseased cartilage that can be used to determine the shape or part of the shape of the articular repair system to match with the surrounding cartilage or subchondral bone.

As described above, the articular repair system may be formed or selected from a library or database of systems of various sizes, curvatures and thicknesses so that it will achieve a near anatomic fit or match with the surrounding or adjacent cartilage and/or subchondral bone. These systems can be pre-made or made to order for an individual patient. In order to control the fit or match of the articular repair system with the surrounding or adjacent cartilage or subchondral bone or menisci and other tissues preoperatively, a software program may be used that projects the articular repair system over the anatomic position where it will be implanted. Suitable software may be commercially available and/or readily modified or designed by a skilled programmer.

In yet another embodiment, the articular surface repair system may be projected over the implantation site using one or more 3-D images. The cartilage and/or subchondral bone and other anatomic structures are extracted from a 3-D electronic image such as an MRI or a CT using manual, semi-automated and/or automated segmentation techniques. A 3-D representation of the cartilage and/or subchondral bone and other anatomic structures as well as the articular repair system is generated, for example using a polygon or NURBS surface or other parametric surface representation. For a description of various parametric surface representations see, for example Foley, J. D. et al., Computer Graphics: Principles and Practice in C; Addison-Wesley, 2.sup.nd edition, 1995). The 3-D representations of the cartilage and/or subchondral bone and other anatomic structures and the articular repair system can be merged into a common coordinate system. The articular repair system can then be placed at the desired implantation site. The representations of the cartilage, subchondral bone, menisci and other anatomic structures and the articular repair system are rendered into a 3-D image, for example application programming interfaces (APIs) OpenGL® (standard library of advanced 3-D graphics functions developed by SGI, Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 3-D image may be rendered showing the cartilage, subchondral bone, menisci or other anatomic objects, and the articular repair system from varying angles, e.g. by rotating or moving them interactively or non-interactively, in real-time or non-real-time. The software can be designed so that the articular repair system with the best fit relative to the cartilage and/or subchondral bone is automatically selected, for example using some of the techniques described above. Alternatively, the operator can select an articular repair system and project it or drag it onto the implantation site using suitable tools and techniques. The operator can move and rotate the articular repair systems in three dimensions relative to the implantation site and can perform a visual inspection of the fit between the articular repair system and the implantation site. The visual inspection can be computer assisted. The procedure can be repeated until a satisfactory fit has been achieved. The procedure can be entirely manual by the operator; it can, however, also be computer-assisted. For example, the software may select a first trial implant that the operator can test. The operator can evaluate the fit. The software can be designed and used to highlight areas of poor alignment between the implant and the surrounding cartilage or subchondral bone or menisci or other tissues. Based on this information, the software or the operator can select another implant and test its alignment. One of skill in the art will readily be able to select, modify and/or create suitable computer programs for the purposes described herein.

In another embodiment, the implantation site may be visualized using one or more cross-sectional 2-D images. Typically, a series of 2-D cross-sectional images will be used. The 2-D images can be generated with imaging tests such as CT, MRI, digital tomosynthesis, ultrasound, or optical coherence tomography using methods and tools known to those of skill in the art. The articular repair system can then be superimposed onto one or more of these 2-D images. The 2-D cross-sectional images can be reconstructed in other planes, e.g. from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2-D images in any desired orientation in real time or near real time; the operator can rotate the imaged tissue volume while doing this. The articular repair system can be displayed in cross-section utilizing different display planes, e.g. sagittal, coronal or axial, typically matching those of the 2-D images demonstrating the cartilage, subchondral bone, menisci or other tissue. Alternatively, a three-dimensional display can be used for the articular repair system. The 2-D electronic image and the 2-D or 3-D representation of the articular repair system can be merged into a common coordinate system. The cartilage repair system can then be placed at the desired implantation site. The series of 2-D cross-sections of the anatomic structures, the implantation site and the articular repair system may be displayed interactively (e.g. the operator can scroll through a series of slices) or non-interactively (e.g. as an animation that moves through the series of slices), in real-time or non-real-time.

The software can be designed so that the articular repair system with the best fit relative to the cartilage and/or subchondral bone is automatically selected, for example using one or more of the techniques described above. Alternatively, the operator can select an articular repair system and project it or drag it onto the implantation site displayed on the cross-sectional 2-D images. The operator can move and rotate the articular repair system relative to the implantation site and scroll through a cross-sectional 2-D display of the articular repair system and of the anatomic structures. The operator can perform a visual and/or computer-assisted inspection of the fit between the articular repair system and the implantation site. The procedure can be repeated until a satisfactory fit has been achieved. The procedure can be entirely manual by the operator; it can, however, also be computer-assisted. For example, the software may select a first trial implant that the operator can test (e.g., evaluate the fit). Software that highlights areas of poor alignment between the implant and the surrounding cartilage or subchondral bone or menisci or other tissues can also be designed and used. Based on this information, the software or the operator can select another implant and test its alignment.

3.0 Implantation

Following one or more manipulations (e.g., shaping, growth, development, etc), the cartilage replacement or regenerating material can then be implanted into the area of the defect. Implantation can be performed with the cartilage replacement or regenerating material still attached to the base material or removed from the base material. Any suitable methods and devices may be used for implantation, for example, devices as described in U.S. Pat. Nos. 6,375,658; 6,358,253; 6,328,765; and International Publication WO 01/19254.

Figure 10A:
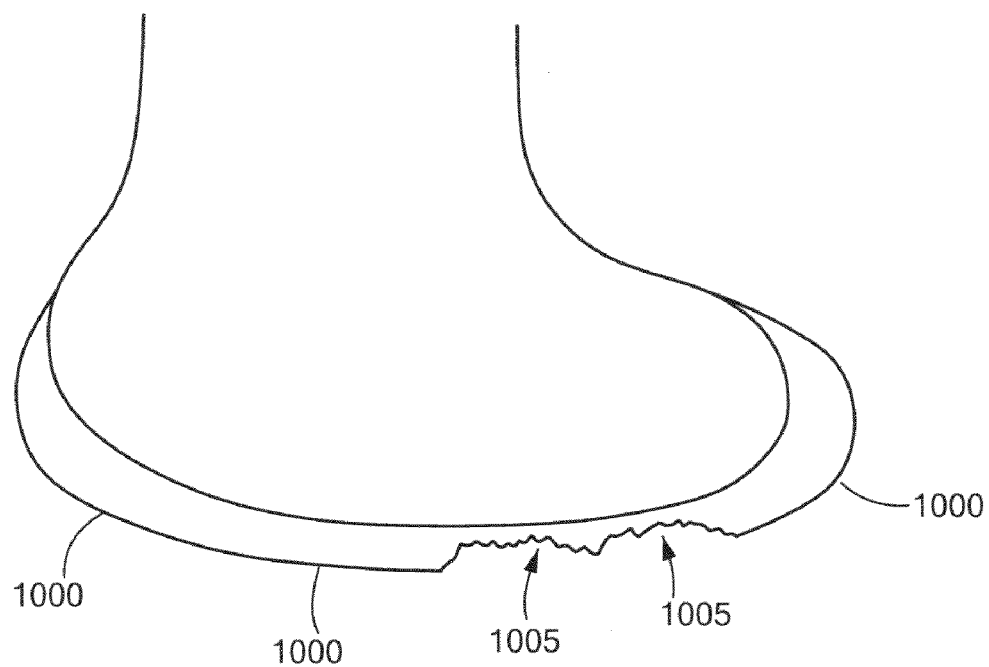
FIG. 10A to C, are schematics depicting other exemplary knee resurfacing devices and methods.
Figure 10B:
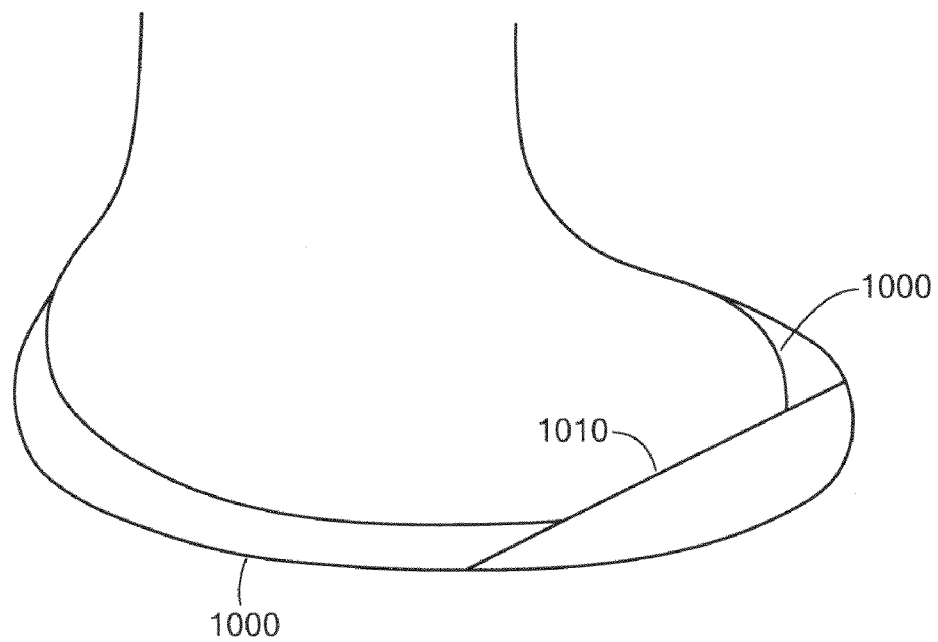
Figure 10C:
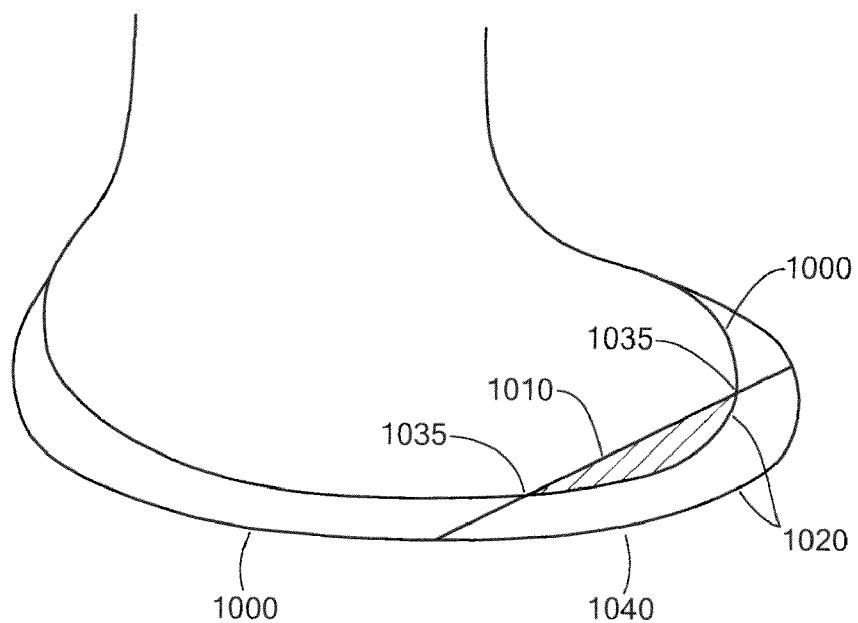
Figure 11A:
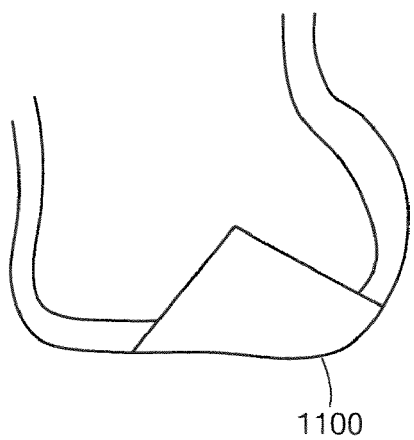
FIGS. 11A and B show exemplary single and multiple component devices.
Figure 11B:
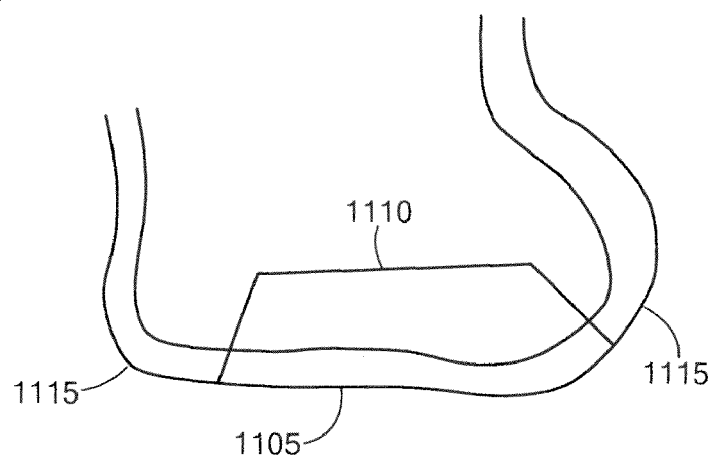
FIG. 11B depicts a multi-component articular surface repair system with a deep component 1110 that mirrors the shape of the subchondral bone and a superficial component 1105 closely matching the shape and curvature of the surrounding normal cartilage 1115. The deep component 1110 and the superficial component 1105 demonstrate varying curvatures and radii with convex and concave portions.

In selected cartilage defects, the implantation site can be prepared with a single cut across the articular surface (FIG. 10). In this case, single 1010 and multi-component 1020 prostheses can be utilized.

3.1 Surgical Tools

Further, surgical assistance can be provided by using a device applied to the outer surface of the articular cartilage or the bone in order to match the alignment of the articular repair system and the recipient site or the joint. The device can be round, circular, oval, ellipsoid, curved or irregular in shape. The shape can be selected or adjusted to match or enclose an area of diseased cartilage or an area slightly larger than the area of diseased cartilage. Alternatively, the device can be designed to be substantially larger than the area of diseased cartilage. Such devices are typically preferred when replacement of a majority or an entire articular surface is contemplated.

Mechanical devices can be used for surgical assistance (e.g., surgical tools), for example using gels, molds, plastics or metal. One or more electronic images can be obtained providing object coordinates that define the articular and/or bone surface and shape. These objects coordinates can be utilized to either shape the device, e.g. using a CAD/CAM technique, to be adapted to a patient's articular anatomy or, alternatively, to select a typically pre-made device that has a good fit with a patient's articular anatomy. The device can have a surface and shape that will match all or portions of the articular or bone surface and shape, e.g. similar to a "mirror image." The device can include apertures, slots and/or holes to accommodate surgical instruments such as drills and saws. Typically, a position will be chosen that will result in an anatomically desirable cut plane or drill hole orientation for subsequent placement of an articular repair system. Moreover, the device can be designed so that the depth of the drill can be controlled, e.g., the drill cannot go any deeper into the tissue than defined by the thickness of the device, and the size of the hole in block can be designed to essentially match the size of the implant. Information about other joints or axis and alignment information of a joint or extremity can be included when selecting the position of these slots or holes.

In certain embodiments, the surgical assistance device comprises an array of adjustable, closely spaced pins (e.g., plurality of individually moveable mechanical elements). One or more electronic images can be obtained providing object coordinates that define the articular and/or bone surface and shape. These objects coordinates can be entered or transferred into the device, for example manually or electronically, and the information can be used to create a surface and shape that will match all or portions of the articular and/or bone surface and shape by moving one or more of the elements, e.g. similar to a "mirror image." The device can include slots and holes to accommodate surgical instruments such as drills and saws. The position of these slots and holes can be adjusted by moving one or more of the mechanical elements. Typically, a position will be chosen that will result in an anatomically desirable cut plane or drill hole orientation for subsequent placement of an articular repair system. Information about other joints or axis and alignment information of a joint or extremity can be included when selecting the position of these slots or holes.

In another embodiment, a frame can be applied to the bone or the cartilage in areas other than the diseased bone or cartilage. The frame can include holders and guides for surgical instruments. The frame can be attached to one or preferably more previously defined anatomic reference points. Alternatively, the position of the frame can be cross-registered relative to one, preferably more anatomic landmarks, using an imaging test, for example one or more fluoroscopic images acquired intraoperatively. One or more electronic images can be obtained providing object coordinates that define the articular and/or bone surface and shape. These objects coordinates can be entered or transferred into the device, for example manually or electronically, and the information can be used to move one or more of the holders or guides for surgical instruments. Typically, a position will be chosen that will result in a surgically or anatomically desirable cut plane or drill hole orientation for subsequent placement of an articular repair system. Information about other joints or axis and alignment information of a joint or extremity can be included when selecting the position of these slots or holes.

For example, when a total knee arthroplasty is contemplated, the patient can undergo an imaging test that will demonstrate the articular anatomy of a knee joint, e.g. width of the femoral condyles, the tibial plateau etc. Additionally, other joints can be included in the imaging test thereby yielding information on femoral and tibial axes, deformities such as varus and valgus and other articular alignment. The imaging test can be an x-ray image, preferably in standing, load-bearing position, a CT scan or an MRI scan or combinations thereof. The articular surface and shape as well as alignment information generated with the imaging test can be used to shape the surgical assistance device or can be entered into the surgical assistance device and can be used to define the preferred location and orientation of saw guides or drill holes or guides for reaming devices. Intraoperatively, the surgical assistance device is applied to the femoral condyle(s) and subsequently the tibial plateau(s) by matching its surface with the articular surface or by attaching it to anatomic reference points on the bone or cartilage. The surgeon can then introduce a saw through the saw guides and prepare the joint for the implantation. By cutting the cartilage and bone along anatomically defined planes, a more reproducible placement of the implant can be achieved. This can ultimately result in improved postoperative results by optimizing biomechanical stresses applied to the implant and surrounding bone for the patient's anatomy.

Figure 15:
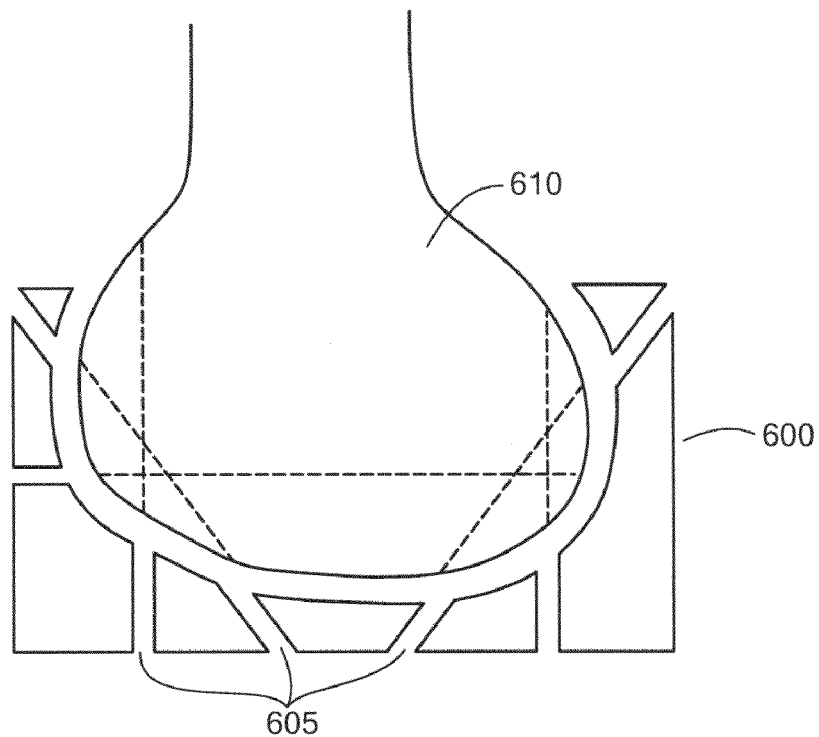
FIG. 15 depicts, in cross-section, an example of a surgical tool 600 containing apertures 605 through which a surgical drill or saw can fit and which guide the drill or saw to make cuts or holes in the bone 610. Dotted lines represent where the cuts corresponding to the apertures will be made in bone.
Figure 16:
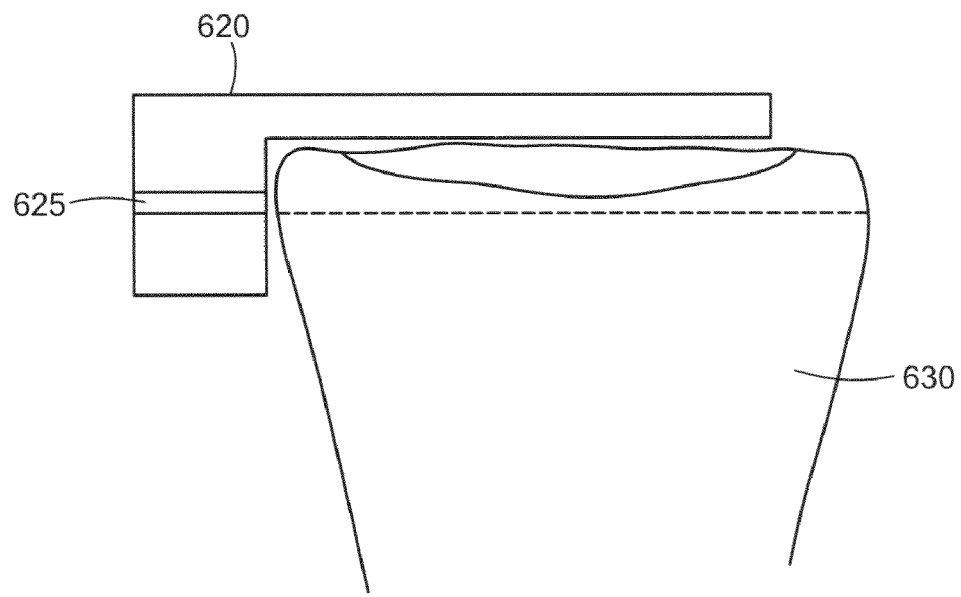
FIG. 16 depicts, in cross-section, another example of a surgical tool 620 containing an aperture 625 through which a surgical drill or saw can fit. The aperture guides the drill or saw to make the proper hole or cut in the underlying bone 630. Dotted lines represent where the cut corresponding to the aperture will be made in bone.
Figure 17A:
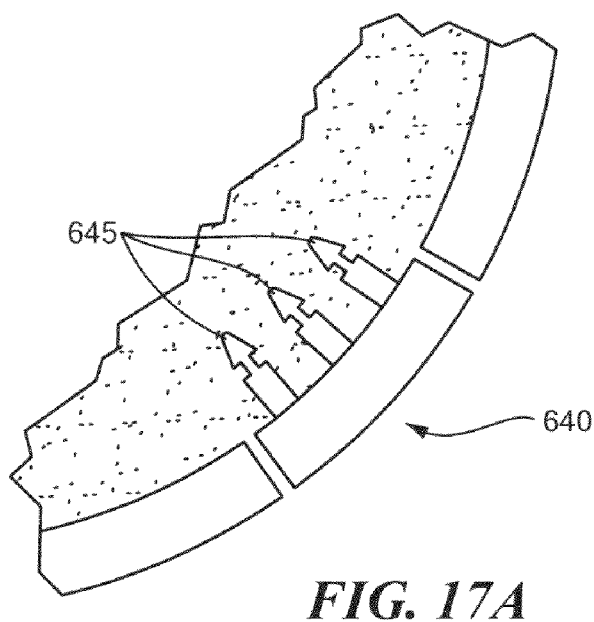
FIG. 17A-D depict, in cross-section, another example of an implant 640 with multiple anchoring pegs 645.
Figure 17B:
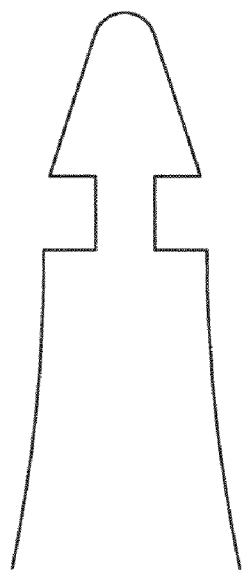
Figure 17C:
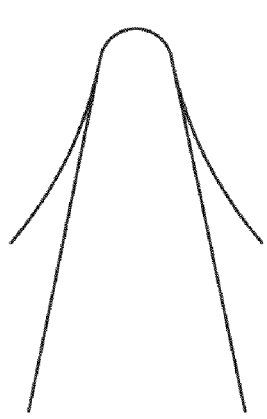
Figure 17D:
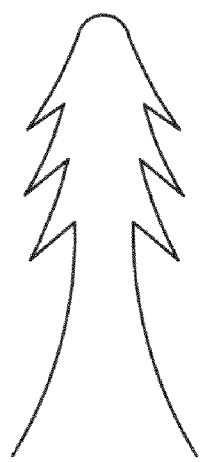
Figure 19B:
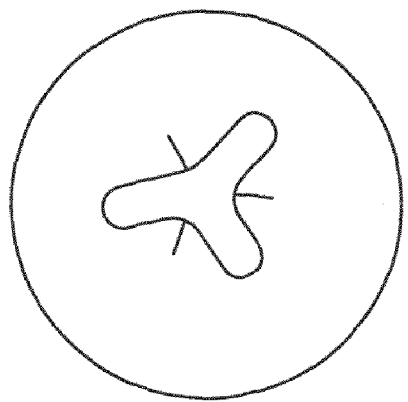
Figure 19C:
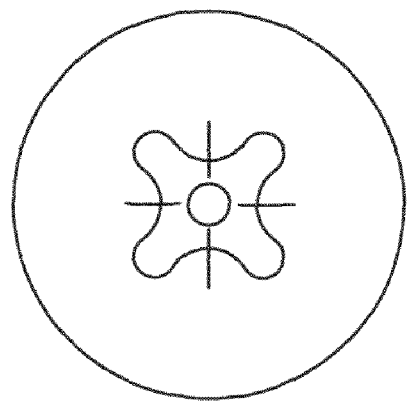
Figure 19D:
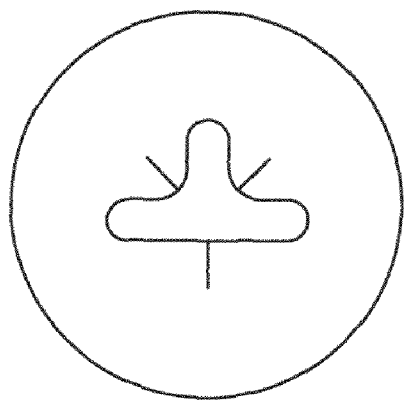
Figure 19E:
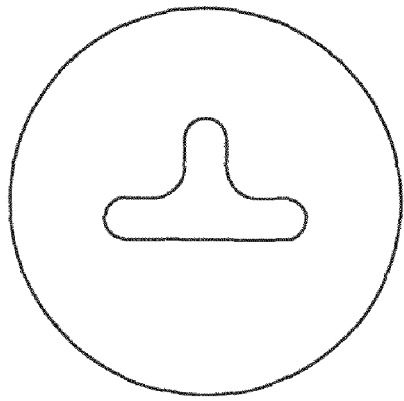

Thus, surgical tools described herein may also be designed and used to control drill alignment, depth and width, for example when preparing a site to receive an implant. (See, FIGS. 13, 15 and 16). For example, the tools described herein, which typically conform to the joint surface, may provide for improved drill alignment and more accurate placement of any implant. An anatomically correct tool can be constructed by a number of methods and may be made of any material, preferably a translucent material such as plastic, lucite, silastic, SLA or the like, and typically is a block-like shape prior to molding.

Furthermore, re-useable tools (e.g., molds) may be also be created and employed. Non-limiting examples of re-useable materials include putties and other deformable materials (e.g., an array of adjustable closely spaced pins that can be configured to match the topography of a joint surface). In these embodiments, the mold may be created directly from the joint during surgery or, alternatively, created from an image of the joint, for example, using one or more computer programs to determine object coordinates defining the surface contour of the joint and transferring (e.g., dialing-in) these coordinates to the tool. Subsequently, the tool can be aligned accurately over the joint and, accordingly, the drill and implant will be more accurately placed in and over the articular surface.

In both single-use and re-useable embodiments, the tool can be designed so that the depth of the block controls the depth of the drill, i.e., the drill cannot go any deeper into the tissue than the depth of block, and the size of the hole in block can be designed to essentially match the size of the implant. The tool can be used for general prosthesis implantation, including, but not limited to, the articular repair implants described herein and for reaming the marrow in the case of a total arthroplasty.

These surgical tools (devices) can also be used to remove an area of diseased cartilage and underlying bone or an area slightly larger than the diseased cartilage and underlying bone. In addition, the device can be used on a "donor," e.g., a cadaveric specimen to obtain implantable repair material. The device is typically positioned in the same general anatomic area in which the tissue was removed in the recipient. The shape of the device is then used to identify a donor site providing a seamless or near seamless match between the donor tissue sample and the recipient site. This is achieved by identifying the position of the device in which the articular surface in the donor, e.g. a cadaveric specimen has a seamless or near seamless contact with the inner surface when applied to the cartilage.

The device can be molded, machined or formed based on the size of the area of diseased cartilage and based on the curvature of the cartilage or the underlying subchondral bone or a combination of both. The device can then be applied to the donor, (e.g., a cadaveric specimen) and the donor tissue can be obtained with use of a blade or saw or other tissue cutting device. The device can then be applied to the recipient in the area of the diseased cartilage and the diseased cartilage and underlying bone can be removed with use of a blade or saw or other tissue cutting device whereby the size and shape of the removed tissue containing the diseased cartilage will closely resemble the size and shape of the donor tissue. The donor tissue can then be attached to the recipient site. For example, said attachment can be achieved with use of screws or pins (e.g., metallic, non-metallic or bioresorable) or other fixation means including but not limited to a tissue adhesive. Attachment can be through the cartilage surface or alternatively, through the marrow space.

The implant site can be prepared with use of a robotic device. The robotic device can use information from an electronic image for preparing the recipient site.

Identification and preparation of the implant site and insertion of the implant can be supported by an image-guided surgery system (surgical navigation system). In such a system, the position or orientation of a surgical instrument with respect to the patient's anatomy is tracked in real-time in one or more 2D or 3D images. These 2D or 3D images can images or can be calculated from images that were acquired preoperatively, such as MR or CT images. The position and orientation of the surgical instrument is determined from markers attached to the instrument. These markers can be located by a detector using, for example, optical, acoustical or electromagnetic signals.

Identification and preparation of the implant site and insertion of the implant can also be supported with use of a C-arm system. The C-arm system can afford imaging of the joint in one or, more preferred, multiple planes. The multiplanar imaging capability can aid in defining the shape of an articular surface. This information can be used to selected an implant with a good fit to the articular surface. Currently available C-arm systems also afford cross-sectional imaging capability, for example for identification and preparation of the implant site and insertion of the implant. C-arm imaging can be combined with administration of radiographic contrast.

In still other embodiments, the surgical devices described herein can include one or more materials that harden to form a mold of the articular surface. A wide-variety of materials that harden in situ have been described including polymers that can be triggered to undergo a phase change, for example polymers that are liquid or semi-liquid and harden to solids or gels upon exposure to air, application of ultraviolet light, visible light, exposure to blood, water or other ionic changes. (See, also, U.S. Pat. No. 6,443,988 and documents cited therein). Non-limiting examples of suitable curable and hardening materials include polyurethane materials (e.g., U.S. Pat. Nos. 6,443,988, 5,288,797, 4,098,626 and 4,594,380; and Lu et al. (2000) BioMaterials 21(15):1595-1605 describing porous poly(L-lactide acid foams); hydrophilic polymers as disclosed, for example, in U.S. Pat. No. 5,162,430; hydrogel materials such as those described in Wake et al. (1995) Cell Transplantation 4(3):275-279, Wiese et al. (2001) J. Biomedical Materials Research 54(2):179-188 and Marler et al. (2000) Plastic Reconstruct. Surgery 105(6):2049-2058; hyaluronic acid materials (e.g., Duranti et al. (1998) Dermatologic Surgery 24(12):1317-1325); expanding beads such as chitin beads (e.g., Yusof et al. (2001) J. Biomedical Materials Research 54(1):59-68); and/or materials used in dental applications (See, e.g., Brauer and Antonucci, "Dental Applications" pp. 257-258 in "Concise Encyclopedia of Polymer Science and Engineering" and U.S. Pat. No. 4,368,040). Any biocompatible material that is sufficiently flowable to permit it to be delivered to the joint and there undergo complete cure in situ under physiologically acceptable conditions can be used. The material may also be biodegradable.

The curable materials can be used in conjunction with a surgical tool as described herein. For example, the surgical tool may include one or more apertures therein adapted to receive injections and the curable materials can be injected through the apertures. Prior to solidifying in situ the materials will conform to the articular surface facing the surgical tool and, accordingly, will form a mirror image impression of the surface upon hardening thereby recreating a normal or near normal articular surface. In addition, curable materials or surgical tools can also be used in conjunction with any of the imaging tests and analysis described herein, for example by molding these materials or surgical tools based on an image of a joint.

4.0 Kits

Also described herein are kits comprising one or more of the methods, systems and/or compositions described herein. In particular, a kit may include one or more of the following: instructions (methods) of obtaining electronic images; systems or instructions for evaluating electronic images; one or more computer means capable of analyzing or processing the electronic images; and/or one or more surgical tools for implanting an articular repair system. The kits may include other materials, for example, instructions, reagents, containers and/or imaging aids (e.g., films, holders, digitizers, etc.).

The following examples are included to more fully illustrate the present invention. Additionally, these examples provide preferred embodiments of the invention and are not meant to limit the scope thereof.

Example 1

Design and Construction of a Three-Dimensional Articular Repair System

Figure 14:
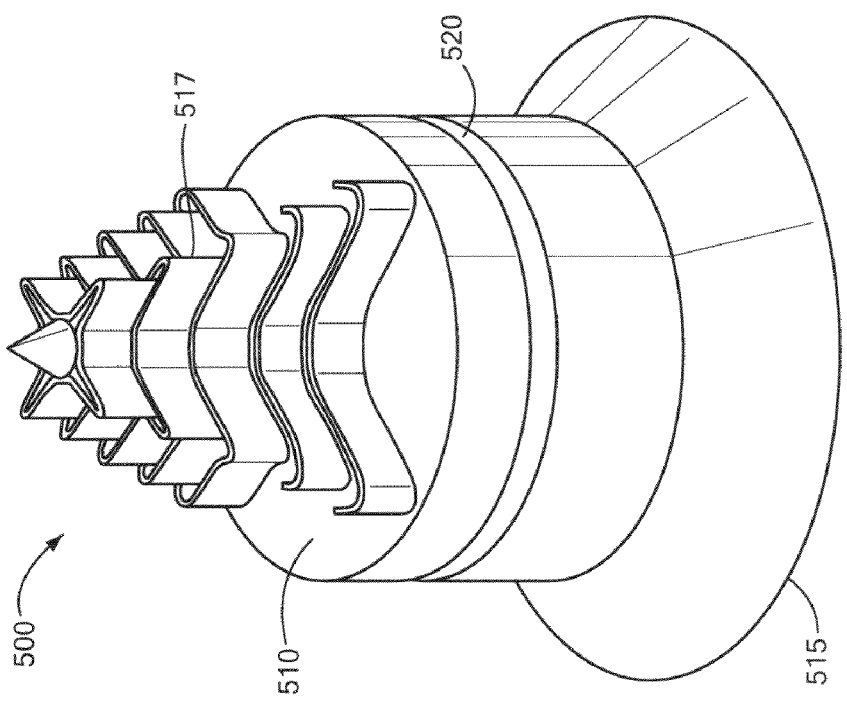
FIG. 14 shows an exemplary articular repair device 500 including a flat surface 510 to control depth and prevent toggle; an exterior surface 515 having the contour of normal cartilage; flanges 517 to prevent rotation and control toggle; a groove 520 to facilitate tissue in-growth.
Figure 13:
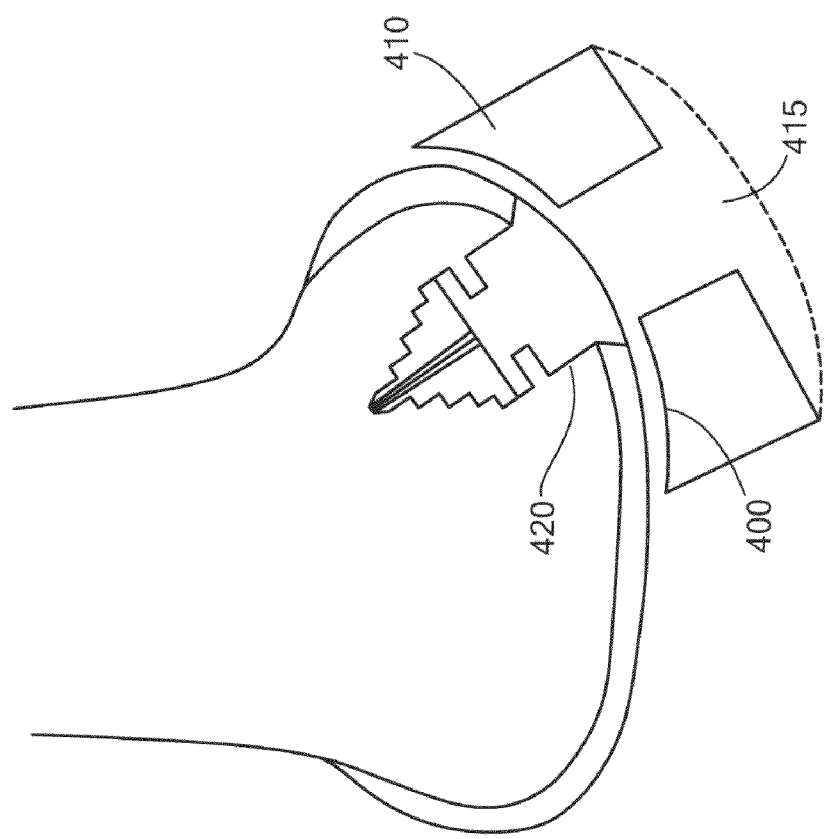
FIG. 13 shows an example of a surgical tool 410 having one surface 400 matching the geometry of an articular surface of the joint. Also shown is an aperture 415 in the tool 410 capable of controlling drill depth and width of the hole and allowing implantation of an insertion of implant 420 having a press-fit design.

Areas of cartilage are imaged as described herein to detect areas of cartilage loss and/or diseased cartilage. The margins and shape of the cartilage and subchondral bone adjacent to the diseased areas are determined. The thickness of the cartilage is determined. The size of the articular repair system is determined based on the above measurements. (FIGS. 12-14). In particular, the repair system is either selected (based on best fit) from a catalogue of existing, pre-made implants with a range of different sizes and curvatures or custom-designed using CAD/CAM technology. The library of existing shapes is typically on the order of about 30 sizes.

The implant is a chromium cobalt implant (see also FIGS. 12-14 and 17-19). The articular surface is polished and the external dimensions slightly greater than the area of diseased cartilage. The shape is adapted to achieve perfect or near perfect joint congruity utilizing shape information of surrounding cartilage and underlying subchondral bone. Other design features of the implant may include: a slanted (60- to 70-degree angle) interface to adjacent cartilage; a broad-based base component for depth control; a press fit design of base component; a porous coating of base component for ingrowth of bone and rigid stabilization; a dual peg design for large defects implant stabilization, also porous coated (FIG. 12A); a single stabilizer strut with tapered, four fin and step design for small, focal defects, also porous coated (FIG. 12B); and a design applicable to femoral resurfacing (convex external surface) and tibial resurfacing (concave external surface).

Example 2

Minimally Invasive, Arthroscopically Assisted Surgical Technique

A. Broad-Based Cartilage Defect

The articular repair systems are inserted using arthroscopic assistance. The device does not require the 15 to 30 cm incision utilized in unicompartmental and total knee arthroplasties. The procedure is performed under regional anesthesia, typically epidural anesthesia. The surgeon may apply a tourniquet on the upper thigh of the patient to restrict the blood flow to the knee during the procedure. The leg is prepped and draped in sterile technique. A stylette is used to create two small 2 mm ports at the anteromedial and the anterolateral aspect of the joint using classical arthroscopic technique. The arthroscope is inserted via the lateral port. The arthroscopic instruments are inserted via the medial port. The cartilage defect is visualized using the arthroscope. A cartilage defect locator device is placed inside the diseased cartilage. The probe has a U-shape, with the first arm touching the center of the area of diseased cartilage inside the joint and the second arm of the U remaining outside the joint. The second arm of the U indicates the position of the cartilage relative to the skin. The surgeon marks the position of the cartilage defect on the skin. A 3 cm incision is created over the defect. Tissue retractors are inserted and the defect is visualized.

A translucent Lucite block matching the 3D shape of the adjacent cartilage and the cartilage defect is placed over the cartilage defect (FIG. 13). For larger defects, the Lucite block includes a lateral slot for insertion of a saw. The saw is inserted and a straight cut is made across the articular surface, removing an area slightly larger than the diseased cartilage. The center of the Lucite block contains two drill holes with a 7.2 mm diameter. A 7.1 mm drill with drill guide controlling the depth of tissue penetration is inserted via the drill hole. Holes for the cylindrical pegs of the implant are created. The drill and the Lucite block are subsequently removed.

A plastic model/trial implant of the mini-repair system matching the outer dimensions of the implant is then inserted. The trial implant is utilized to confirm anatomic placement of the actual implant. If indicated, the surgeon can make smaller adjustments at this point to improve the match, e.g. slight expansion of the drill holes or adjustment of the cut plane.

The implant is then inserted with the pegs pointing into the drill holes. Anterior and posterior positions of the implant are color-coded; specifically the anterior peg is marked with a red color and a small letter "A", while the posterior peg has a green color and a small letter "P". Similarly, the medial aspect of the implant is color-coded yellow and marked with a small letter "M" and the lateral aspect of the implant is marked with a small letter "L". The Lucite block is then placed on the external surface of the implant and a plastic hammer is used to gently advance the pegs into the drill holes. The pegs are designed to achieve a press fit.

The same technique can be applied in the tibia. The implant has a concave articular surface matching the 3D shape of the tibial plateau. Immediate stabilization of the device can be achieved by combining it with bone cement if desired.

B. Small, Focal Cartilage Defect

After identification of the cartilage defect and marking of the skin surface using the proprietary U-shaped cartilage defect locator device as described herein, a 3 cm incision is placed and the tissue retractors are inserted. The cartilage defect is visualized.

A first Lucite block matching the 3D surface of the femoral condyle is placed over the cartilage defect. The central portion of the Lucite block contains a drill hole with an inner diameter of, for example, 1.5 cm, corresponding to the diameter of the base plate of the implant. A standard surgical drill with a drill guide for depth control is inserted through the Lucite block, and the recipient site is prepared for the base component of the implant. The drill and the Lucite block are then removed.

A second Lucite block of identical outer dimensions is then placed over the implant recipient site. The second Lucite block has a rounded, cylindrical extension matching the size of the first drill hole (and matching the shape of the base component of the implant), with a diameter 0.1 mm smaller than the first drill hole and 0.2 mm smaller than that of the base of the implant. The cylindrical extension is placed inside the first drill hole.

The second Lucite block contains a drill hole extending from the external surface of the block to the cylindrical extension. The inner diameter of the second drill hole matches the diameter of the distal portion of the fin-shaped stabilizer strut of the implant, e.g. 3 mm. A drill, e.g. with 3 mm diameter, with a drill guide for depth control is inserted into the second hole and the recipient site is prepared for the stabilizer strut with four fin and step design. The drill and the Lucite block are then removed.

A plastic model/trial implant matching the 3-D shape of the final implant with a diameter of the base component of 0.2 mm less than that of the final implant and a cylindrical rather than tapered strut stabilizer with a diameter of 0.1 mm less than the distal portion of the final implant is then placed inside the cartilage defect. The plastic model/trial implant is used to confirm alignment of the implant surface with the surrounding cartilage. The surgeon then performs final adjustments.

The implant is subsequently placed inside the recipient site. The anterior fin of the implant is marked with red color and labeled "A." The posterior fin is marked green with a label "P" and the medial fin is color coded yellow with a label "M." The Lucite block is then placed over the implant. A plastic hammer is utilized to advance the implant slowly into the recipient site. A press fit is achieved with help of the tapered and four fin design of the strut, as well as the slightly greater diameter (0.1 mm) of the base component relative to the drill hole. The Lucite block is removed. The tissue retractors are then removed. Standard surgical technique is used to close the 3 cm incision. The same procedure described above for the medial femoral condyle can also be applied to the lateral femoral condyle, the medial tibial plateau, the lateral tibial plateau and the patella. Immediate stabilization of the device can be achieved by combining it with bone cement if desired.

What is claimed is:

1. A method of manufacturing an articular implant for repairing articular cartilage of a joint, the articular implant having an inner surface for facing bone and an outer surface for facing a cavity of the joint, the method including:
    obtaining image data of the joint, the image data including shape information of an articular surface of the joint;
    deriving a desired shape of the articular implant based at least in part on the shape information; and
    designing and manufacturing the articular implant with the outer surface of the implant based, at least in part, on the desired shape, and wherein at least a portion of the inner surface includes a planar surface configured to abut a cut bone surface when the articular implant is implanted on the joint during a surgical procedure, and wherein the cut bone surface has a predetermined position or orientation relative to at least one of an anatomical and mechanical axis of the joint.

2. The method of claim 1, wherein the articular implant includes an attachment mechanism for fixing the articular implant to the joint.

3. The method of claim 1, wherein the designing and manufacturing step further includes selecting a pre-existing implant having a pre-existing shape and further manipulating one or more dimensions of the selected implant.

4. The method of claim 3, wherein the one or more dimensions comprises a size of the selected implant.

5. The method of claim 3, wherein the one or more dimensions comprises a thickness of the selected implant.

6. The method of claim 3, wherein the one or more dimensions comprises a curvature of the selected implant.

7. The method of claim 1, wherein the deriving step further includes deriving the shape of the subchondral bone from the shape information.

8. The method of claim 7, wherein the designing and manufacturing step includes designing and manufacturing the articular implant such that at least a portion of the inner surface of the implant achieves a near anatomic fit with a portion of the subchondral bone of the joint.

9. The method of claim 1, wherein the deriving step further includes deriving the shape of the articular cartilage from the shape information.

10. The method of claim 9, wherein the designing and manufacturing step includes designing and manufacturing the articular implant such that at least a portion of the outer surface of the implant achieves a near anatomic fit with surrounding natural cartilage of the joint.

11. The method of claim 9, wherein the designing and manufacturing step includes designing and manufacturing the articular implant such that at least a portion of the outer surface of the implant achieves a near anatomic fit with adjacent natural cartilage of the joint.

12. The method of claim 1, wherein the step of obtaining the image of the joint comprises obtaining the image from at least one member of the group comprising MRI, CT, ultrasound, laser, digital tomosynthesis, optical coherence tomography and optical imaging.

13. The method of claim 1, wherein the step of obtaining the image of the joint comprises obtaining the image from at least one member of the group comprising a knee, a femoral condyle, a tibial plateau, a patella, a femoral head, an acetabulum, a shoulder, a hip, a vertebrae, an elbow and an ankle.

14. The method of claim 1, wherein the designing and manufacturing step is performed utilizing Computer Aided Design or Computer Aided Manufacturing (CAD/CAM) techniques.

15. The method of claim 1, wherein the designing and manufacturing step is performed automatically.

16. The method of claim 1, wherein at least one of the obtaining, deriving or designing and manufacturing steps requires human intervention.

17. A method of manufacturing an articular implant for repairing articular cartilage of a joint, the articular implant having an inner surface for facing bone and an outer surface for facing a cavity of the joint, the method including:
   obtaining image data of the joint,
   deriving from the image data shape information of at least one of normal, diseased or damaged articular cartilage of the joint;
   deriving a desired shape of the articular implant based at least in part on the derived shape information; and
   designing and manufacturing the articular implant with the outer surface of the implant based, at least in part, on the desired shape, and wherein at least a portion of the inner surface includes a planar surface configured to abut a cut bone surface when the articular implant is implanted on the joint during a surgical procedure, and wherein the cut bone surface has a predetermined position or orientation relative to at least one of an anatomical and mechanical axis of the joint.

18. The method of claim 17, wherein the articular implant includes an attachment mechanism for fixing the articular implant to the joint.

19. The method of claim 17, wherein the designing and manufacturing step further includes selecting a pre-existing implant having a pre-existing shape and further manipulating one or more dimensions of the selected implant.

20. The method of claim 19, wherein the one or more dimensions comprises a size of the selected implant.

21. The method of claim 19, wherein the one or more dimensions comprises a thickness of the selected implant.

22. The method of claim 19, wherein the one or more dimensions comprises a curvature of the selected implant.

23. The method of claim 17, wherein the deriving step further includes deriving the shape of the subchondral bone from the shape information.

24. The method of claim 17, wherein the designing and manufacturing step is performed automatically.

25. The method of claim 17, wherein at least one of the obtaining, deriving or designing and manufacturing steps requires human intervention.

26. A method of manufacturing an articular implant for repairing articular cartilage of a joint, the articular implant having an inner surface for facing bone and an outer surface for facing a cavity of the joint, the method including:
   obtaining image data of the joint,
   deriving from the image data shape information of subchondral bone of the joint;
   deriving a desired shape of the articular implant based at least in part on the shape information; and
   designing and manufacturing the articular implant with the outer surface of the implant based, at least in part, on the desired shape, and wherein at least a portion of the inner surface includes a planar surface configured to abut a cut bone surface when the articular implant is implanted on the joint during a surgical procedure, and wherein the cut bone surface has a predetermined position or orientation relative to at least one of an anatomical and mechanical axis of the joint.

27. The method of claim 26, wherein the articular implant includes an attachment mechanism for fixing the articular implant to the joint.

28. The method of claim 26, wherein the designing and manufacturing step further includes selecting a pre-existing implant having a pre-existing shape and further manipulating one or more dimensions of the selected implant.

29. The method of claim 28, wherein the one or more dimensions comprises a size of the selected implant.

30. The method of claim 28, wherein the one or more dimensions comprises a thickness of the selected implant.

31. The method of claim 28, wherein the one or more dimensions comprises a curvature of the selected implant.

32. The method of claim 26, wherein the deriving step further includes deriving the shape of the articular cartilage from the shape information.

33. The method of claim 26, wherein the designing and manufacturing step is performed automatically.

34. The method of claim 26, wherein at least one of the obtaining, deriving or designing and manufacturing steps requires human intervention.

* * * * *